US009428577B2

(12) United States Patent
Arch et al.

(10) Patent No.: US 9,428,577 B2
(45) Date of Patent: Aug. 30, 2016

(54) PLATELET-DERIVED GROWTH FACTOR B SPECIFIC ANTIBODIES AND COMPOSITIONS AND USES THEREOF

(71) Applicant: Pfizer Inc., New York, NY (US)

(72) Inventors: Robert Arch, Saint Louis, MO (US); Gregory Carven, Maynard, MA (US); Jun Kuai, Lexington, MA (US); Lydia Mosyak, Newton, MA (US); Shinji Ogawa, Setagaya (JP); Dirk Ponsel, Germering (DE); Robert Rauchenberger, Farchant (DE)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/075,755

(22) Filed: Nov. 8, 2013

(65) Prior Publication Data

US 2014/0134176 A1 May 15, 2014

Related U.S. Application Data

(60) Provisional application No. 61/724,888, filed on Nov. 9, 2012.

(51) Int. Cl.
*A61K 39/395* (2006.01)
*C07K 16/22* (2006.01)

(52) U.S. Cl.
CPC ........... *C07K 16/22* (2013.01); *C07K 2317/21* (2013.01); *C07K 2317/34* (2013.01); *C07K 2317/55* (2013.01); *C07K 2317/56* (2013.01); *C07K 2317/76* (2013.01); *C07K 2317/92* (2013.01); *C07K 2317/94* (2013.01)

(58) Field of Classification Search
CPC ..................... A61K 39/3955; A61K 38/1858; C07K 16/22; C07K 14/49
See application file for complete search history.

(56) References Cited

FOREIGN PATENT DOCUMENTS

WO            01/05950         1/2001

OTHER PUBLICATIONS

Ogawa Shinji et al., "Anti-PDGF-B monoclonal antibody reduces liver fibrosis development", Hepatology Research, vol. 40, No. 11, pp. 1128-1141, Nov. 2010.
Trojanowska, "Role of PDGF in fibrotic diseases and systemic sclerosis", Rheumatology, vol. 47, supple 5, v2-v4, 2008.
Andrae et al. "Role of platelet-derived growth factors in physiology and medicine," Genes Dev. vol. 22, pp. 1276-1312, 2008.
Silver et al., "Platelet-derived growth factor synthesis in mesangial cells: induction by multiple peptide mitogens.," Proc. Natl. Acad. Sci. USA, vol. 86, pp. 1056-1060, 1989.
Floege et al., "Mitogenic effect of platelet-derived growth factor in human glomerular mesangial cells: modulation and/or suppression by inflammatory cytokines." Clin. Exp. Immunol. vol. 86, pp. 334-341, 1991.

Floege et al., "Infusion of platelet-derived growth factor or basic fibroblast growth factor induces selective glomerular mesangial cell proliferation and matrix accumulation in rats." J. Clin. Invest. vol. 92, pp. 2952-2962, 1993.
Isaka et al., "Glomerulosclerosis induced by in vivo transfection of transforming growth factor-beta or platelet-derived growth factor gene into the rat kidney." J. Clin. Invest., vol. 92, pp. 2597-2601, 1993.
Leveen et al., "Mice deficient for PDGF B show renal, cardiovascular, and hematological abnormalities." Genes Dev. vol. 8, pp. 1875-1887, 1994.
Soriano P., "Abnormal kidney development and hematological disorders in PDGF beta-receptor mutant mice." Genes Dev. vol. 8, pp. 1888-1896, 1994.
Floege et al., "Novel Approach to Specific Growth Factor Inhibition in Vivo: Antagonism of Platelet-Derived Growth Factor in Glomerulonephritis by Aptamers." Am. J. Pathol., vol. 154, pp. 169-179, 1999.
Gilbert et al., "PDGF signal transduction inhibition ameliorates experimental mesangial proliferative glomerulonephritis." Kidney International. 59:1324-1332, 2001.
Nakamura et al., "Electroporation-mediated PDGF receptor-IgG chimera gene transfer ameliorates experimental glomerulonephritis." Kidney International, vol. 59, pp. 2134-2145, 2001.
Ostendorf et al., "Specific Antagonism of PDGF Prevents Renal Scarring in Experimental Glomerulonephritis." J. Am. Soc. Nephrol., vol. 12, pp. 909-918, 2001.
Czochra et al., "Liver fibrosis induced by hepatic overexpression of PDGF-B in transgenic mice." J. Hepatology, vol. 45, pp. 419-28, 2006.
Ikura et al., "Expression of platelet-derived growth factor and its receptor in livers of patients with chronic liver disease.," J Gastroenterology, vol. 32, pp. 496-501, 1997.
Kinnman et al., "PDGF-Mediated Chemoattraction of Hepatic Stellate Cells by Bile Duct Segments in Cholestatic Liver Injury." Lab. Invest., vol. 80, pp. 697-707, 2000.
Grappone et al., "Expression of platelet-derived growth factor in newly formed cholangiocytes during experimental biliary fibrosis in rats." J. Hepatology, vol. 31, pp. 100-109, 1999.
Bonner, JC, "Regulation of PDGF and its receptors in fibrotic diseases." Cytokine Growth Factor Rev., vol. 15, pp. 255-273, 2004.
Kinnman et al., "Hepatic Stellate Cell Proliferation is an Early Platelet-Derived Growth Factor-Mediated Cellular Event in Rat Cholestatic Liver Injury." Lab. Invest., vol. 81, pp. 1709-1716, 2001.
Kinnman et al., "The Myofibroblastic Conversion of Peribiliary Fibrogenic Cells Distinct from Hepatic Stellate Cells is Stimulated by Platelet-Derived Growth Factor During Liver Fibrogenesis." Lab. Invest. 83:163-173, 2003.
Borkham et al., "Antisense strategy against PDGF B-chain proves effective in preventing experimental liver fibrogenesis." Biochem. Biophys. Res. Commun., vol. 321, pp. 413-423, 2004.
Borkham et al., "Dominant-negative soluble PDGF-b receptor inhibits hepatic stellate cell activation and attenuates liver fibrosis." Lab. Invest., vol. 84, pp. 766-777, 2004.

(Continued)

*Primary Examiner* — Marianne P Allen

(57) ABSTRACT

The present invention provides antibodies, or antigen-binding fragment thereof, which specifically bind to PDGF-B. The invention further provides a method of obtaining such antibodies and nucleic acids encoding the same. The invention further relates to compositions and therapeutic methods for use of these antibodies for the treatment and/or prevention of PDGF-B mediated diseases, disorders or conditions.

7 Claims, 29 Drawing Sheets

(56) References Cited

OTHER PUBLICATIONS

Neef et al., "Oral imatinib treatment reduces early fibrogenesis but does not prevent progression in the long term." J. Hepatology, vol. 44, pp. 167-175, 2006.

Arunklakshana & Schild, "Some Quantitative Uses of Drug Antagonists." Brit. J. Pharmacol., vol. 65, pp. 48-58, 1959.

Heldin and Westermark, "Mechanism of Action and in vivo Role of Platelet-Derived Growth Factor." Physiological Revs. 79(4):1238-1316, 1999.

Laimer et al., "PDGFR blockade is a rational and effective therapy for NPM-ALK-driven lymphomas." Nature Med. 18 (11):1699-1704, 2012.

Knappik et al., "Fully synthetic human combinatorial antibody libraries (HuCAL) based on modular consensus frameworks and CDRs randomized with trinucleotides." J Mol Biol, 296; 57-86, 2000.

Shim et al., "Structures of a platelet-derived growth factor/ propeptide complex and a platelet-derived growth factor/receptor complex." Proc. Natl. Acad. Sci. USA 107:11307-11312, 2010.

Ostendorf et al., "The PDGF family in renal fibrosis." Pediatric Nephrol. 27:1041-1050, 2012.

Boor et al., "PDGF-D inhibition by CR002 ameliorates tubulointerstitial fibrosis following experimental glomerulonephritis." Nephrol Dial Transplant 22:1323-1331, 2007.

Yadav et al., "Factors affecting the viscosity in high concentration solutions of different monoclonal antibodies." J. Pharm. Sci., 99(12):4812-4829, 2010.

Chaudhri et al., "The Role of Amino Acid Sequence in the Self-Association of Therapeutic Monoclonal Antibodies: Insights from Coarse-Grained Modeling." J. Phys. Chem. B, 117(5):1269-1279, 2013.

Yadav et al., "The Influence of Charge Distribution on Self-Association and Viscosity Behavior of Monoclonal Antibody Solutions." Mol. Pharmaceutics 9(4):791-802), 2012.

FIGURE 1

1A  Heavy chain germlining

| FW %ID | ID | FW1 | CDR1 | FW2 | CDR2 | FW3 | SEQ ID NO: |
|---|---|---|---|---|---|---|---|
| | MCR-B457 Heavy Chain | EVQLVESGGGLVQPGGSLRLSCAASGFTFS | SYAMS | WVRQAPGKGLEWVS | MIS_DDGSIKYYADSVKG | RFTISRDNSKNTLYLQMNSLRAEDTAVYYCAR | 2 |
| 98.6 | lcl\|IMGT IGHV3-23~01 | .............................L | ..... | .............. | A..gSG...T....... | ............................K... | 25 |
| 98.6 | lcl\|IMGT IGHV3-23~02 | .............................L | ..... | .............. | A..gSG...T..G.... | ............................K... | 26 |
| 98.6 | lcl\|IMGT IGHV3-23~03 | .............................L | ..... | .............. | V.Y.SG....ST..... | ............................K... | 27 |
| 98.6 | lcl\|IMGT IGHV3-23~05 | .............................L | ..... | .............. | A..Y.SS...ST..... | ............................K... | 28 |

FIGURE 1 (continued)

1B
Light chain germlining

| FW %ID | ID | FW1 | CDR1 | FW2 | CDR2 | FW3 | SEQ ID NO: |
|---|---|---|---|---|---|---|---|
| | MOR-8457 Light Chain | SYELTQPPSVSVAPGQTARISC | SGDSLGSYFVH | WYQQKPGQAPVLVIY | DDSNRPS | GIPERFSGSNSGNTATLTISGTQAEDEADYYC | 1 |
| 92.7 | lcl|IMGT.I GLV3-1~01 | ......S......S.T. | ...K..DKYAC | .............S. | Q...K. | ..............................M..... | 29 |
| 91.3 | lcl|IMGT.I GLV3-25~03 | ......S..........T. | ...A..PKQYAY | ................ | K...E. | ..........S..T.V..........V...... | 30 |
| 91.3 | lcl|IMGT.I GLV3-9~01 | ...L.....L.......T. | G.NMT..KN. | ................ | R..... | ..............................RA..G..... | 31 |
| 89.8 | lcl|IMGT.I GLV3-25~01 | ...M..........S....T. | ...A..PKQYAY | ................ | K...E. | ..........S..T.V..........V...... | 32 |

FIGURE 1 (Continued)

1C  MOR8457-VL

SYELTQPPSVSVAPGQTARISCSGDSLGSYFVHWYQQKPG
QAPVLVIYDDSNRPSGIPERFSGSNSGNTATLTISGTQAED
EADYYCSAFTHNSDVFGGGTKLTVL (SEQ ID NO:1)

1D  MOR8457-VH

EVQLVESGGGLVQPGGSLRLSCAASGFTSSYAMSWVRQ
APGKGLEWVSYISDDGSLKYYADSVKGRFTISRDNSKNT
LYLQMNSLRAEDTAVYYCARHPYWYGGQLDLWGQGTL
VTVSS (SEQ ID NO:2)

1E  MOR8457-GL-VL

SYELTQPPSVSVSPGQTASITCSGDSLGSYFVHWYQQ
KPGQSPVLVIYDDSNRPSGIPERFSGSNSGNTATLTIS
GTQAMDEADYYCSAFTHNSDVFGGGTKLTVL (SEQ
ID NO:4)

FIGURE 1 (Continued)

1F MOR8457-GL-VH

EVQLLESGGGLVQPGGSLRLSCAASGFTFSSYAM SWVRQAPGKGLEWVSYISDDGSLKYYADSVKGR FTISRDNSKNTLYLQMNSLRAEDTAVYYCAKHP YWYGGQLDLWGQGTLVTVSS (SEQ ID NO:6)

1G MOR8457-GL-LC

SYELTQPPSVSVSPGQTASITCSGDSLGSYFVHWYQQ KPGQSPVLVIYDDSNRPSGIPERFSGSNSGNTATLTIS GTQAMDEADYYCSAFTHNSDVFGGGTKLTVLGQPK AAPSVTLFPPSSEELQANKATLVCLISDFYPGAVTVA WKADSSPVKAGVETTTPSKQSNNKYAASSYLSLTPE QWKSHRSYSCQVTHEGSTVEKTVAPTECS (SEQ ID NO:16)

FIGURE 1 (Continued)

1H  MOR8457-GL-hIgG1-3m-HC

EVQLLESGGGLVQPGGSLRLSCAASGFTFSSYAMSWV
RQAPGKGLEWVSYISDDGSLKYYADSVKGRFTISRDN
SKNTLYLQMNSLRAEDTAVYYCAKHPYWYGGQLDL
WGQGTLVTVSSASTKGPSVFPLAPSSKSTSGGTAALGC
LVKDYFPEPVTVSWNSGALTSGVHTFPAVLQSSGLYSL
SSVVTVPSSSLGTQTYICNVNHKPSNTKVDKKVEPKS
CDKTHTCPPCPAPEAAGAPSVFLFPPKPKDTLMISRT
PEVTCVVVDVSHEDPEVKFNWYVDGVEVHNAKTKP
REEQYNSTYRVVSVLTVLHQDWLNGKEYKCKVSNKA
LPAPIEKTISKAKGQPREPQVYTLPPSREEMTKNQVSL
TCLVKGFYPSDIAVEWESNGQPENNYKTTPPVLDSDG
SFFLYSKLTVDKSRWQQGNVFSCSVMHEALHNHYTQ
KSLSLSPG (SEQ ID NO:14)

FIGURE 1 (Continued)

1I MOR8457-15-VL
SYELTQPPSVSVSPGQTASITCSGDSLGSYFVHWYQQKPGQSPVLVIYDDSNRRPSGIPERFSGSNSGNTATLTISGTQAMDEADYYCSAFTHNSNVFGGGTKLTVL (SEQ ID No: 34)

1J MOR8457-15/16-VH
EVQLLQSGGGLVKPGGSLRLSCAASGFTFSSYAMSWVRQAPGKGLEWVSYISDDGSLKYYADSVKGRFTISRDNSKNTLYLQMNSLRAEDTAVYYCARHPYWYGGQLDLWGQGTLVTVSS (SEQ ID No: 44)

1K MOR8457-16-VL
SYELTQPPSVSVSPGQTASITCSGDSLGSYFVHWYQQKPGQSPVLVIYDDSKRPSGIPERFSGSNSGNTATLTISGTQAMDEADYYCSAFTHNSDVFGGGTKLTVL (SEQ ID No: 39)

FIGURE 1 (Continued)

1L MOR8457-15-LC

SYELTQPPSVSVSPGQTASITCSGDSLGSYFVHWYQ
QKPGQSPVLVIYDDSNRPSGIPERFSGSNSGNTATL
TISGTQAMDEADYYCSAFTHNSNVFGGGTKLTVLG
QPKAAPSVTLFPPSSEELQANKATLVCLISDFYPGA
VTVAWKADSSPVKAGVETTTPSKQSNNKYAASSYL
SLTPEQWKSHRSYSCQVTHEGSTVEKTVAPTECS
(SEQ ID No: 37)

FIGURE 1 (Continued)

| 1M | MOR8457-15/16-HC | EVQLLQSGGGLVKPGGSLRLSCAASGFTFSSYAMSWVRQAPGKGLEWVSYISDDGSLKYYADSVKGRFTISRDNSKNTLYLQMNSLRAEDTAVYYCARHPYWYGGQLDLWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAG<u>A</u>PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID No: 46) |

FIGURE 1 (Continued)

| | | |
|---|---|---|
| 1N | MOR8457-16-LC | SYELTQPPSVSVSPGQTASITCSGDSLGSYFVHWYQQK PGQSPVLVIYDDSKRPSGIPERFSGSNSGNTATLTISGT QAMDEADYYCSAFTHNSDVFGGGTKLTVLGQPKAAPS VTLFPPSSEELQANKATLVCLISDFYPGAVTVAWKADS SPVKAGVETTTPSKQSNNKYAASSYLSLTPEQWKSHR SYSCQVTHEGSTVEKTVAPTECS(SEQ ID No: 42) |

MOR8457-IKR-hIgG1-3m did not bind human PDGF-BB when it was bound to hPDGFRβ-hIgG1.

MOR8457 blocked human PDGF-BB binding to PDGFRβ-hIgG1 in solution.

MOR-8457 Binding Epitope on PDGF-BB

FIGURE 8
MOR8457 potently inhibited PDGF-BB induced human mesangial cell proliferation.
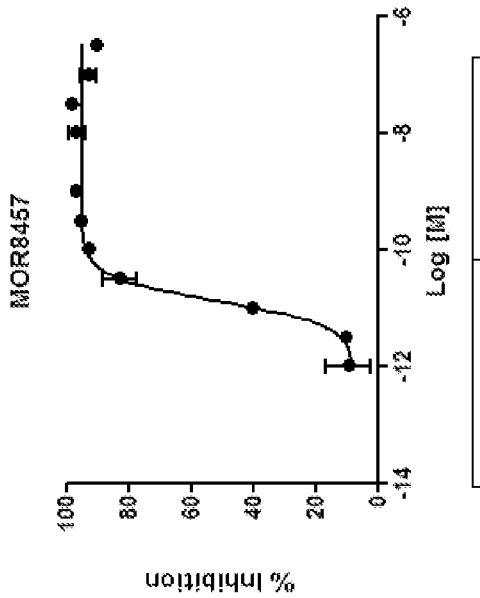
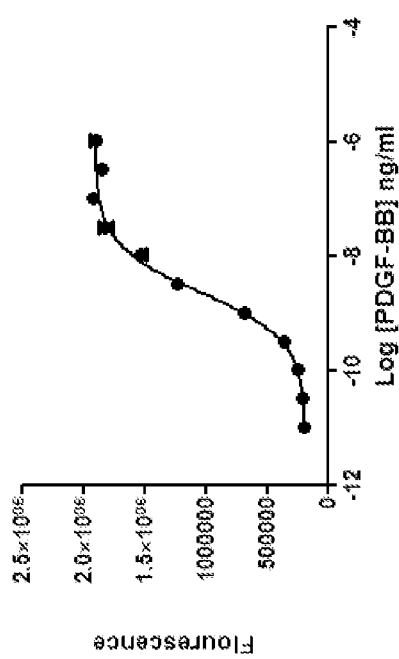

Effect of MOR8457-mIgG1 or isotype control on mesangial cell proliferation on anti-Thy1.1 nephritis kidney tissue samples day 9 post OX-7 induction

SEQUENCE LISTING

<160> NUMBER OF SEQ ID NOS: 47

<210> SEQ ID NO 1

<211> LENGTH: 106
<212> TYPE: PRT
<213> ORGANISM: Artificial Sequence
<220> FEATURE:
<223> OTHER INFORMATION: MOR8457 light chain V domain

<400> SEQUENCE: 1

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Ser Tyr Phe Val
            20                  25                  30

His Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Val Leu
            100                 105

<210> SEQ ID NO 2
<211> LENGTH: 120
<212> TYPE: PRT
<213> ORGANISM: Artificial Sequence
<220> FEATURE:
<223> OTHER INFORMATION: MOR8457 heavy chain V domain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Tyr Trp Tyr Gly Gly Gln Leu Asp Leu Trp Gly Gln
            100                 105                 110

Gly Thr Leu Val Thr Val Ser Ser
        115                 120

<210> SEQ ID NO 3
<211> LENGTH: 319
<212> TYPE: DNA
<213> ORGANISM: Artificial Sequence
<220> FEATURE:
<223> OTHER INFORMATION: MOR8457 light chain V domain germlined

<400> SEQUENCE: 3
agctacgagc tgacccagcc ccccagcgtg agcgtgtccc ccggccagac cgccagcatc      60
acctgcagcg gcgacagcct gggcagctac ttcgtacact ggtaccagca gaagcccggc     120
cagtcccccg tgctggtgat ctacgacgac agcaacagac ccagcggcat ccccgagaga     180

```
ttcagcggca gcaacagcgg caacaccgcc accctgacca tcagcggcac ccaggccatg    240
gacgaggccg actactactg cagcgccttc acccacaaca gcgacgtgtt cggcggcggc    300
accaagctga ccgtgctag                                                 319
```

<210> SEQ ID NO 4
<211> LENGTH: 106
<212> TYPE: PRT
<213> ORGANISM: Artificial Sequence
<220> FEATURE:
<223> OTHER INFORMATION: MOR8457 light chain V domain germlined

<400> SEQUENCE: 4

```
Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Val Leu
            100                 105
```

<210> SEQ ID NO 5
<211> LENGTH: 360
<212> TYPE: DNA
<213> ORGANISM: Artificial Sequence
<220> FEATURE:
<223> OTHER INFORMATION: MOR8457 heavy chain V domain germlined

<400> SEQUENCE: 5

```
gaggtgcagc tgctggagag cggcggcggc ctggtgcagc ccggcggcag cctgagactg    60
agctgcgccg ccagcggctt caccttcagc agctacgcca tgagctgggt gagacaggcc    120
cccggcaagg gcctggagtg ggtgagctac atcagcgacg acggcagcct gaagtactac    180
gccgacagcg tgaagggcag attcaccatc agcagagaca cagcaagaa cacccctgtac    240 ctgcagatga acagcctgag agccgaggac accgccgtgt actactgcgc aaacaccccc    300
tactggtacg cggccagct ggacctgtgg ggccagggca ccctggtgac cgtgtcctca    360
```

<210> SEQ ID NO 6
<211> LENGTH: 120
<212> TYPE: PRT
<213> ORGANISM: Artificial Sequence
<220> FEATURE:
<223> OTHER INFORMATION: MOR8457 heavy chain V domain germlined

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Pro Tyr Trp Tyr Gly Gly Gln Leu Asp Leu Trp Gly Gln
            100                 105                 110

Gly Thr Leu Val Thr Val Ser Ser
        115                 120

<210> SEQ ID NO 7
<211> LENGTH: 10
<212> TYPE: PRT
<213> ORGANISM: Artificial Sequence
<220> FEATURE:
<223> OTHER INFORMATION: MOR8457 CDR-H1

<400> SEQUENCE: 7

Gly Phe Thr Phe Ser Ser Tyr Ala Met Ser
 1               5                  10

<210> SEQ ID NO 8
<211> LENGTH: 17
<212> TYPE: PRT
<213> ORGANISM: Artificial Sequence
<220> FEATURE:
<223> OTHER INFORMATION: MOR8457 CDR-H2

<400> SEQUENCE: 8

Tyr Ile Ser Asp Asp Gly Ser Leu Lys Tyr Tyr Ala Asp Ser Val Lys
 1               5                  10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: MOR8457 CDR-H3

<400> SEQUENCE: 9

His Pro Tyr Trp Tyr Gly Gly Gln Leu Asp Leu
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: MOR8457 CDR-L1

<400> SEQUENCE: 10

Ser Gly Asp Ser Leu Gly Ser Tyr Phe Val His
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: MOR8457 CDR-L2

<400> SEQUENCE: 11

Asp Asp Ser Asn Arg Pro Ser
```

<210> SEQ ID NO 12
<211> LENGTH: 9
<212> TYPE: PRT
<213> ORGANISM: Artificial Sequence
<220> FEATURE:
<223> OTHER INFORMATION: MOR8457 CDR-L3

<400> SEQUENCE: 12

Ser Ala Phe Thr His Asn Ser Asp Val
1               5

<210> SEQ ID NO 13
<211> LENGTH: 1347
<212> TYPE: DNA
<213> ORGANISM: Artificial Sequence
<220> FEATURE:
<223> OTHER INFORMATION: MOR8457 full length heavy chain germlined with
      triple effector null mutant IgG1 constant domain

<400> SEQUENCE: 13

| | | |
|---|---|---|
| gaggtgcagc tgctggagag cggcggcggc ctggtgcagc ccggcggcag cctgagactg | 60 |
| agctgcgccg ccagcggctt caccttcagc agctacgcca tgagctgggt gagacaggcc | 120 |
| cccggcaagg gcctggagtg ggtgagctac atcagcgacg acggcagcct gaagtactac | 180 |
| gccgacagcg tgaagggcag attcaccatc agcagagaca cagcaagaa caccctgtac | 240 |
| ctgcagatga acagcctgag agccgaggac accgccgtgt actactgcgc caaacacccc | 300 |
| tactggtacg gcggccagct ggacctgtgg ggccagggca ccctggtgac cgtgtcctca | 360 |
| gcgtcgacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaagc cgctgggca | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag gcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc ccccgga | 1347 |

<210> SEQ ID NO 14
<211> LENGTH: 449
<212> TYPE: PRT
<213> ORGANISM: Artificial Sequence
<220> FEATURE:
<223> OTHER INFORMATION: MOR8457 full length heavy chain germlined with triple effector null mutant IgG1 constant domain

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Tyr Trp Tyr Gly Gly Gln Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 15
<211> LENGTH: 636
<212> TYPE: DNA
<213> ORGANISM: Artificial Sequence
<220> FEATURE:
<223> OTHER INFORMATION: germlined MOR8457 full length light chain

<400> SEQUENCE: 15
agctacgagc tgacccagcc ccccagcgtg agcgtgtccc ccggccagac cgccagcatc      60
acctgcagcg gcgacagcct gggcagctac ttcgtacact ggtaccagca gaagcccggc     120
cagtcccccg tgctggtgat ctacgacgac agcaacagac ccagcggcat ccccgagaga     180
ttcagcggca gcaacagcgg caacaccgcc accctgacca tcagcggcac ccaggccatg     240
gacgaggccg actactactg cagcgccttc acccacaaca gcgacgtgtt cggcggcggc     300
accaagctga ccgtgctagg tcagcccaag gctgccccct cggtcactct gttcccgccc     360
tcctctgagg agcttcaagc caacaaggcc acactggtgt gtctcataag tgacttctac     420
ccgggagccg tgacagtggc ctggaaggca gatagcagcc ccgtcaaggc gggagtggag     480
accaccacac cctccaaaca aagcaacaac aagtacgcgg ccagcagcta tctgagcctg     540
acgcctgagc agtggaagtc cacagaagc tacagctgcc aggtcacgca tgaagggagc     600
accgtggaga agacagtggc ccctacagaa tgttca                              636

<210> SEQ ID NO 16
<211> LENGTH: 212
<212> TYPE: PRT
<213> ORGANISM: Artificial Sequence
<220> FEATURE:
<223> OTHER INFORMATION: MOR8457 full length light chain germlined

<400> SEQUENCE: 16

Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140
```

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 17
<211> LENGTH: 212
<212> TYPE: PRT
<213> ORGANISM: Artificial Sequence
<220> FEATURE:
<223> OTHER INFORMATION: MOR8457- IKR full length light chain

<400> SEQUENCE: 17

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Ser Tyr Phe Val
            20                  25                  30

His Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Ile Lys Arg Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 18
<211> LENGTH: 449
<212> TYPE: PRT
<213> ORGANISM: Artificial Sequence
<220> FEATURE:
<223> OTHER INFORMATION: MOR8457-hIgG1 full length heavy chain with
      triple effector null mutant IgG1 constant domain

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Tyr Trp Tyr Gly Gly Gln Leu Asp Leu Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                    420                 425                 430
Glu Ala Leu His Asn His Tyr Thr Gln Lys Ser Leu Ser Leu Ser Pro
            435                 440                 445
Gly

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 20
<211> LENGTH: 323
<212> TYPE: PRT
<213> ORGANISM: Mus musculus

<400> SEQUENCE: 20

Ala Lys Thr Thr Pro Pro Ser Val Tyr Pro Leu Ala Pro Gly Ser Ala
1               5                   10                  15

Ala Gln Thr Asn Ser Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Pro Ser Ser Thr Trp Pro Ser Glu Thr Val Thr
65                  70                  75                  80

Cys Asn Val Ala His Pro Ala Ser Ser Thr Lys Val Asp Lys Lys Ile
                85                  90                  95

Val Pro Arg Asp Cys Gly Cys Lys Pro Cys Ile Cys Thr Val Pro Glu
            100                 105                 110

Val Ser Ser Val Phe Ile Phe Pro Pro Lys Pro Lys Asp Val Leu Thr
        115                 120                 125

Ile Thr Leu Thr Pro Lys Val Thr Cys Val Val Val Asp Ile Ser Lys
    130                 135                 140

Asp Asp Pro Glu Val Gln Phe Ser Trp Phe Val Asp Asp Val Glu Val
145                 150                 155                 160

His Thr Ala Gln Thr Gln Pro Arg Glu Glu Gln Phe Asn Ser Thr Phe
                165                 170                 175

Arg Ser Val Ser Glu Leu Pro Ile Met His Gln Asp Trp Leu Asn Gly
            180                 185                 190

Lys Glu Phe Lys Cys Arg Val Asn Ser Ala Ala Phe Pro Ala Pro Ile
        195                 200                 205

Glu Lys Thr Ile Ser Lys Thr Lys Gly Arg Pro Lys Ala Pro Gln Val
    210                 215                 220

Tyr Thr Ile Pro Pro Pro Lys Glu Gln Met Ala Lys Asp Lys Val Ser
225                 230                 235                 240

Leu Thr Cys Met Ile Thr Asp Phe Phe Pro Glu Asp Ile Thr Val Glu
                245                 250                 255

Trp Gln Trp Asn Gly Gln Pro Ala Glu Asn Tyr Lys Asn Thr Gln Pro
            260                 265                 270

Ile Met Asp Thr Asp Gly Ser Tyr Phe Val Tyr Ser Lys Leu Asn Val
        275                 280                 285

Gln Lys Ser Asn Trp Glu Ala Gly Asn Thr Phe Thr Cys Ser Val Leu
    290                 295                 300

His Glu Gly Leu His Asn His His Thr Glu Lys Ser Leu Ser His Ser
305                 310                 315                 320

Pro Gly Lys

<210> SEQ ID NO 21
<211> LENGTH: 329
<212> TYPE: PRT
<213> ORGANISM: Artificial Sequence
<220> FEATURE:
<223> OTHER INFORMATION: human IgG1 triple mutant (3m) effector null
      mutant constant region

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 22
<211> LENGTH: 326
<212> TYPE: PRT
<213> ORGANISM: Homo sapiens

<400> SEQUENCE: 22

Ala Ser Phe Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Trp Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Cys Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 106
<212> TYPE: PRT
<213> ORGANISM: Homo sapiens

<400> SEQUENCE: 23

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
 65                  70                  75                  80
```

```
Ser His Arg Ser Tyr Ser Cys Gln Val Thr His Glu Gly Ser Thr Val
            85                  90                  95

Glu Lys Thr Val Ala Pro Thr Glu Cys Ser
            100                 105

<210> SEQ ID NO 24
<211> LENGTH: 109
<212> TYPE: PRT
<213> ORGANISM: Mus musculus

<400> SEQUENCE: 24

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Phe Thr Lys Val Asp Gly Thr
            35                  40                  45

Pro Val Thr Gln Gly Met Glu Thr Thr Gln Pro Ser Lys Gln Ser Asn
        50                  55                  60

Asn Lys Tyr Met Ala Ser Ser Tyr Leu Thr Leu Thr Ala Arg Ala Trp
65                  70                  75                  80

Glu Arg His Ser Ser Tyr Ser Cys Gln Val Thr His Glu Gly His Thr
            85                  90                  95

Val Glu Phe Thr Lys Ser Leu Ser Arg Ala Asp Cys Ser
            100                 105

<210> SEQ ID NO 25
<211> LENGTH: 98
<212> TYPE: PRT
<213> ORGANISM: Artificial Sequence
<220> FEATURE:
<223> OTHER INFORMATION: IGHV3-23*01

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 26
<211> LENGTH: 98
<212> TYPE: PRT
<213> ORGANISM: Artificial Sequence
<220> FEATURE:
<223> OTHER INFORMATION: IGHV3-23*02

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Gly Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 27
<211> LENGTH: 98
<212> TYPE: PRT
<213> ORGANISM: Artificial Sequence
<220> FEATURE:
<223> OTHER INFORMATION: IGHV3-23*03

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Val Ile Tyr Ser Gly Gly Ser Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 28
<211> LENGTH: 98
<212> TYPE: PRT
<213> ORGANISM: Artificial Sequence
<220> FEATURE:
<223> OTHER INFORMATION: IGHV3-23*05

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Tyr Ser Ser Gly Ser Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 29
<211> LENGTH: 87
```

```
<212> TYPE: PRT
<213> ORGANISM: Artificial Sequence
<220> FEATURE:
<223> OTHER INFORMATION: IGLV3-1*01

<400> SEQUENCE: 29

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys
                85

<210> SEQ ID NO 30
<211> LENGTH: 87
<212> TYPE: PRT
<213> ORGANISM: Artificial Sequence
<220> FEATURE:
<223> OTHER INFORMATION: IGLV3-25*03

<400> SEQUENCE: 30

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys
                85

<210> SEQ ID NO 31
<211> LENGTH: 87
<212> TYPE: PRT
<213> ORGANISM: Artificial Sequence
<220> FEATURE:
<223> OTHER INFORMATION: IGLV3-9*01

<400> SEQUENCE: 31

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys
```

<210> SEQ ID NO 32
<211> LENGTH: 87
<212> TYPE: PRT
<213> ORGANISM: Artificial Sequence
<220> FEATURE:
<223> OTHER INFORMATION: IGLV3-25*01

<400> SEQUENCE: 32

```
Ser Tyr Glu Leu Met Gln Pro Pro Ser Val Ser Val Ser Pro Gly Gln
1               5                   10                  15
Thr Ala Arg Ile Thr Cys Ser Gly Asp Ala Leu Pro Lys Gln Tyr Ala
            20                  25                  30
Tyr Trp Tyr Gln Gln Lys Pro Gly Gln Ala Pro Val Leu Val Ile Tyr
        35                  40                  45
Lys Asp Ser Glu Arg Pro Ser Gly Ile Pro Glu Arg Phe Ser Gly Ser
    50                  55                  60
Ser Ser Gly Thr Thr Val Thr Leu Thr Ile Ser Gly Val Gln Ala Glu
65                  70                  75                  80
Asp Glu Ala Asp Tyr Tyr Cys
                85
```

<210> SEQ ID NO 33
<211> LENGTH: 241
<212> TYPE: PRT
<213> ORGANISM: Homo sapiens

<400> SEQUENCE: 33

```
Met Asn Arg Cys Trp Ala Leu Phe Leu Ser Leu Cys Cys Tyr Leu Arg
1               5                   10                  15
Leu Val Ser Ala Glu Gly Asp Pro Ile Pro Glu Glu Leu Tyr Glu Met
            20                  25                  30
Leu Ser Asp His Ser Ile Arg Ser Phe Asp Asp Leu Gln Arg Leu Leu
        35                  40                  45
His Gly Asp Pro Gly Glu Glu Asp Gly Ala Glu Leu Asp Leu Asn Met
    50                  55                  60
Thr Arg Ser His Ser Gly Gly Glu Leu Glu Ser Leu Ala Arg Gly Arg
65                  70                  75                  80
Arg Ser Leu Gly Ser Leu Thr Ile Ala Glu Pro Ala Met Ile Ala Glu
                85                  90                  95
Cys Lys Thr Arg Thr Glu Val Phe Glu Ile Ser Arg Arg Leu Ile Asp
            100                 105                 110
Arg Thr Asn Ala Asn Phe Leu Val Trp Pro Pro Cys Val Glu Val Gln
        115                 120                 125
Arg Cys Ser Gly Cys Cys Asn Asn Arg Asn Val Gln Cys Arg Pro Thr
    130                 135                 140
Gln Val Gln Leu Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
                165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
        195                 200                 205
Thr Ile Arg Thr Val Arg Val Arg Arg Pro Pro Lys Gly Lys His Arg
    210                 215                 220
```

Lys Phe Lys His Thr His Asp Lys Thr Ala Leu Lys Glu Thr Leu Gly
225                 230                 235                 240

Ala

<210> SEQ ID NO 34
<211> LENGTH: 106
<212> TYPE: PRT
<213> ORGANISM: Artificial Sequence
<220> FEATURE:
<223> OTHER INFORMATION: MOR8457-15 light chain engineered V domain

<400> SEQUENCE: 34

Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asn Val
                85                  90                  95

Phe Gly Gly Gly Thr Lys Leu Thr Val Leu
            100                 105

<210> SEQ ID NO 35
<211> LENGTH: 318
<212> TYPE: DNA
<213> ORGANISM: Artificial Sequence
<220> FEATURE:
<223> OTHER INFORMATION: MOR8457-15 light chain engineered V domain

<400> SEQUENCE: 35
agctacgagc tgacccagcc ccccagcgtg agcgtgtccc ccggccagac cgccagcatc      60
acctgcagcg gcgacagcct gggcagctac ttcgtacact ggtaccagca gaagcccggc     120
cagtcccccg tgctggtgat ctacgacgac agcaacagac ccagcggcat ccccgagaga     180
ttcagcggca gcaacagcgg caacaccgcc accctgacca tcagcggcac ccaggccatg     240
gacgaggccg actactactg cagcgccttc acccacaaca gcaacgtgtt cggcggcggc     300
accaagctga ccgtgcta                                                   318

<210> SEQ ID NO 36
<211> LENGTH: 9
<212> TYPE: PRT
<213> ORGANISM: Artificial Sequence
<220> FEATURE:
<223> OTHER INFORMATION: MOR8457-15 CDR-L3

<400> SEQUENCE: 36

Ser Ala Phe Thr His Asn Ser Asn Val
1               5

<210> SEQ ID NO 37
<211> LENGTH: 212
<212> TYPE: PRT
<213> ORGANISM: Artificial Sequence
<220> FEATURE:
<223> OTHER INFORMATION: MOR8457-15 light chain with engineered V domain

<400> SEQUENCE: 37

```
Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asn Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
        210
```

<210> SEQ ID NO 38
<211> LENGTH: 636
<212> TYPE: DNA
<213> ORGANISM: Artificial Sequence
<220> FEATURE:
<223> OTHER INFORMATION: MOR8457-15 light chain with engineered V domain

<400> SEQUENCE: 38

```
agctacgagc tgacccagcc ccccagcgtg agcgtgtccc ccggccagac cgccagcatc    60
acctgcagcg gcgacagcct gggcagctac ttcgtacact ggtaccagca gaagcccggc   120
cagtcccccg tgctggtgat ctacgacgac agcaacagac cagcggcat ccccgagaga   180
ttcagcggca gcaacagcgg caacaccgcc accctgacca tcagcggcac ccaggccatg   240
gacgaggccg actactactg cagcgccttc acccacaaca gcaacgtgtt cggcggcggc   300
accaagctga ccgtgctagg tcagcccaag gctgccccct cggtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgcgg ccagcagcta tctgagcctg   540
acgcctgagc agtggaagtc ccacagaagc tacagctgcc aggtcacgca tgaagggagc   600
accgtggaga agacagtggc ccctacagaa tgttca                            636
```

<210> SEQ ID NO 39

<211> LENGTH: 106
<212> TYPE: PRT
<213> ORGANISM: Artificial Sequence
<220> FEATURE:
<223> OTHER INFORMATION: MOR8457-16 light chain V domain

<400> SEQUENCE: 39

Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
        35                  40                  45

Asp Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Val Leu
            100                 105

<210> SEQ ID NO 40
<211> LENGTH: 318
<212> TYPE: DNA
<213> ORGANISM: Artificial Sequence
<220> FEATURE:
<223> OTHER INFORMATION: MOR8457-16 light chain V domain

<400> SEQUENCE: 40
agctacgagc tgacccagcc ccccagcgtg agcgtgtccc ccggccagac cgccagcatc      60
acctgcagcg gcgacagcct gggcagctac ttcgtacact ggtaccagca gaagcccggc     120
cagtcccccg tgctggtgat ctacgacgac agcaagagac ccagcggcat ccccgagaga     180
ttcagcggca gcaacagcgg caacaccgcc accctgacca tcagcggcac ccaggccatg     240
gacgaggccg actactactg cagcgccttc acccacaaca gcgacgtgtt cggcggcggc     300
accaagctga ccgtgcta                                                   318

<210> SEQ ID NO 41
<211> LENGTH: 7
<212> TYPE: PRT
<213> ORGANISM: Artificial Sequence
<220> FEATURE:
<223> OTHER INFORMATION: MOR8457-16 CDR-L2

<400> SEQUENCE: 41

Asp Asp Ser Lys Arg Pro Ser
1               5

<210> SEQ ID NO 42
<211> LENGTH: 212
<212> TYPE: PRT
<213> ORGANISM: Artificial Sequence
<220> FEATURE:
<223> OTHER INFORMATION: MOR8457-16 light chain with engineered V domain

<400> SEQUENCE: 42

Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Phe Val
            20                  25                  30

His Trp Tyr Gln Gln Lys Pro Gly Gln Ser Pro Val Leu Val Ile Tyr
                35                  40                  45

Asp Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Ala Phe Thr His Asn Ser Asp Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
            210

<210> SEQ ID NO 43
<211> LENGTH: 636
<212> TYPE: DNA
<213> ORGANISM: Artificial Sequence
<220> FEATURE:
<223> OTHER INFORMATION: MOR8457-16 light chain with engineered V domain

<400> SEQUENCE: 43
agctacgagc tgacccagcc ccccagcgtg agcgtgtccc ccggccagac cgccagcatc        60
acctgcagcg gcgacagcct gggcagctac ttcgtacact ggtaccagca gaagcccggc       120
cagtcccccg tgctggtgat ctacgacgac agcaagagac ccagcggcat ccccgagaga       180
ttcagcggca gcaacagcgg caacaccgcc accctgacca tcagcggcac ccaggccatg       240
gacgaggccg actactactg cagcgccttc acccacaaca gcgacgtgtt cggcggcggc       300
accaagctga ccgtgctagg tcagcccaag gctgcccct cggtcactct gttcccgccc        360
tcctctgagg agcttcaagc caacaaggcc acactggtgt gtctcataag tgacttctac       420
ccgggagccg tgacagtggc ctggaaggca gatagcagcc ccgtcaaggc gggagtggag       480
accaccacac cctccaaaca aagcaacaac aagtacgcgg ccagcagcta tctgagcctg       540
acgcctgagc agtggaagtc ccacagaagc tacagctgcc aggtcacgca tgaagggagc       600
accgtggaga agacagtggc ccctacagaa tgttca                                 636

<210> SEQ ID NO 44
<211> LENGTH: 120
<212> TYPE: PRT
<213> ORGANISM: Artificial Sequence
<220> FEATURE:
<223> OTHER INFORMATION: MOR8457-15/16 heavy chain engineered V domain

<400> SEQUENCE: 44

Glu Val Gln Leu Leu Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Tyr Trp Tyr Gly Gly Gln Leu Asp Leu Trp Gly Gln
            100                 105                 110

Gly Thr Leu Val Thr Val Ser Ser
            115                 120

<210> SEQ ID NO 45
<211> LENGTH: 362
<212> TYPE: DNA
<213> ORGANISM: Artificial Sequence
<220> FEATURE:
<223> OTHER INFORMATION: MOR8457-15/16 heavy chain engineered V domain

<400> SEQUENCE: 45
gaggtgcagc tgctgcagag cggcggcggc ctggtgaagc ccggcggcag cctgagactg      60
agctgcgccg ccagcggctt caccttcagc agctacgcca tgagctgggt gagacaggcc     120
cccggcaagg gcctggagtg ggtgagctac atcagcgacg acggcagcct gaagtactac     180
gccgacagcg tgaagggcag attcaccatc agcagagaca cagcaagaa cacccctgtac     240 ctgcagatga acagcctgag agccgaggac accgccgtgt actactgcgc cagacacccc     300
tactggtacg gcggccagct ggacctgtgg ggccagggca ccctggtgac cgtgtcctca     360
gc                                                                     362

<210> SEQ ID NO 46
<211> LENGTH: 449
<212> TYPE: PRT
<213> ORGANISM: Artificial Sequence
<220> FEATURE:
<223> OTHER INFORMATION: MOR8457-15/16 hIgG1 full length heavy chain
      with engineered V domain and triple effector null mutant IgG1
      constant domain

<400> SEQUENCE: 46

Glu Val Gln Leu Leu Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Asp Asp Gly Ser Leu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Tyr Trp Tyr Gly Gly Gln Leu Asp Leu Trp Gly Gln

```
                    100                 105                 110
    Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
    145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Ala Ala Gly Ala
    225                 230                 235                 240

Pro Ser Val Phe Leu Phe Pro Pro Lys Pro Lys Asp Thr Leu Met Ile
                    245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
    305                 310                 315                 320

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
    385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 47
<211> LENGTH: 1347
<212> TYPE: DNA
<213> ORGANISM: Artificial Sequence
<220> FEATURE:
<223> OTHER INFORMATION: MOR8457-15/16 hIgG1 full length heavy chain
      with engineered V domain and triple effector null mutant IgG1
      constant domain

<400> SEQUENCE: 47
```

```
gaggtgcagc tgctgcagag cggcggcggc ctggtgaagc ccggcggcag cctgagactg      60
agctgcgccg ccagcggctt caccttcagc agctacgcca tgagctgggt gagacaggcc     120
cccggcaagg gcctggagtg ggtgagctac atcagcgacg acggcagcct gaagtactac     180
gccgacagcg tgaagggcag attcaccatc agcagagaca acagcaagaa caccctgtac     240
ctgcagatga acagcctgag agccgaggac accgccgtgt actactgcgc cagacacccc     300
tactggtacg gcggccagct ggacctgtgg ggcagggca ccctggtgac cgtgtcctca      360
gcgtcgacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaagc cgctggggca     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc ccccgga                                        1347
```

PLATELET-DERIVED GROWTH FACTOR B SPECIFIC ANTIBODIES AND COMPOSITIONS AND USES THEREOF This application claims the benefit of U.S. Provisional Patent Application No. 61/724,888, filed on Nov. 9, 2012, and PCT/IB2013/059718, filed on Oct. 28, 2013, the entire contents of which are hereby incorporated by reference.

SEQUENCE LISTING

This application contains a Sequence Listing submitted as an electronic text file named "PC071978_SEQLISTING_ST25.txt", having a size in bytes of 62,395, and created on Nov. 8, 2013. The information contained in this electronic file is hereby incorporated by reference in its entirety.

FIELD OF THE INVENTION

The present invention relates to antibodies, e.g., full length antibodies and antigen binding fragments thereof that specifically bind platelet-derived growth factor B (PDGF-B). The invention further relates to compositions comprising antibodies to PDGF-B, and methods of using the antibodies as a medicament. The PDGF-B antibodies are useful for treating and preventing diseases and disorders mediated by PDGF-B binding to PDGFRβ (both PDGFRββ and PDGFRαβ homo- and heterodimeric receptors, respectively).

BACKGROUND OF THE INVENTION

Many chronic diseases are characterized by persistent and unremitting inflammation, injury, tissue remodeling and fibrosis. For instance, in the cohort of progressive renal diseases, which includes diabetic nephropathy, IgA nephropathy and proliferative lupus nephritis, these are histologically characterized by mesangial cell expansion and glomerular as well as tubulointerstitial fibrosis. In this respect, ligands of the platelet-derived growth factor (PDGF) receptor-β are probably the best characterized mediators to date.

PDGFs are the primary mitogens for the cells of the mesenchymal and neuroectodermal origin. The PDGF family is composed of four different polypeptide chains, PDGF-A, B, C and D, which have been shown to form 5 distinct proteins by homo and heterodimerization, PDGF-AA, -AB, -BB, -CC and -DD. PDGFs exert their biological activities by activating two structurally related tyrosine kinase receptors, PDGF-Rα and β, which form homo- and heterodimers (e.g., PDGFRαα, PDGFRαβ, PDGFRββ). PDGF-A activates PDGFRαα, while PDGF-B can activate all three receptor dimers, i.e., PDGF-Rαα, PDGF-Rαβ, PDGF-Rββ. PDGF-AB and PDGF-C activate PDGF-Rαα and PDGF-Rαβ, whereas PDGF-D preferentially activates PDGF-Rββ as reviewed by Trojanowska (2008, Rheumatology 47:v2-v4).

PDGFs have been implicated in a wide variety of human diseases, including, but not limited to, atherosclerosis, restenosis, pulmonary hypertension, retinal vascular disease, organ fibrosis (e.g., cardiac, lung, renal and kidney), rheumatoid arthritis, osteoarthritis, tumorigenesis, and systemic sclerosis (SSc; scleroderma) (see, e.g., Trojanowska, 2008, Rheumatology 47:v2-v4; Andrae et al. 2008 Genes Dev. 22:1276-1312).

More specifically, all four PDGF isoforms, as well as both receptor chains, are expressed in the kidney and increased expression of PDGF in glomerular and/or interstitial locations has been documented in a large variety of renal diseases.

In addition, increased expression of PDGF receptors occurs in experimental and human renal diseases. Both PDGF-B and PDGF-D appear to be especially important in human renal diseases. Mesangial cells produce PDGF-B in vitro, and various growth factors induce mesangial proliferation via induction of autocrine or paracrine PDGF-B-chain excretion (Silver et al., 1989, Proc. Natl. Acad. Sci. USA 86:1056-1060; Floege et al., 1991, Clin. Exp. Immunol. 86:334-341). Overexpression of PDGF-B-chain induces mesangial proliferation and matrix expansion (Floege et al., 1993, J. Clin. Invest. 92:2952-2962; Isaka et al., 1993, J. Clin. Invest. 92:2597-2601) and PDGF-B-chain or β-receptor knock-out mice fail to develop a mesangium (Leveen et al., 1994, Genes Dev. 8:1875-1887; Soriano P., 1994, Genes Dev. 8:1888-1896).

Specific inhibition of PDGF-B using antibodies, aptamers, soluble PDGF receptors or PDGF β-receptor tyrosine kinase blockers reduces mesangioproliferative changes, prevents long-term renal scarring and improves renal function in a number of different pre-clinical models (Floege et al., 1999, Am. J. Pathol. 154:169-179; Gilbert et al., 2001, Kidney Int. 59:1324-1332; Nakamura et al., 2001, Kidney Int. 59:2134-2145; Ostendorf et al., 2001, J. Am. Soc. Nephrol. 12:909-918).

Similarly, liver fibrosis is commonly observed after chronic liver injury. The major event in hepatic fibrogenesis is the proliferation of, and collagen production by hepatic stellate cells and myofibroblasts. As is the case for glomerulonephritides, PDGF is strongly mitogenic and causes hepatic stellate cell and myofibroblast chemotaxis (Czochra et al., 2006, J. Hepatol. 45:419-28). In human cirrhotic liver, PDGF-BB and PDGFRβ protein expression is markedly enhanced in comparison with normal liver (Ikura et al., 1997, J. Gastroenterol. 32:496-501). In a cholestatic liver injury model induced by bile duct ligation (BDL) in rats, PDGF-B mRNA expression and PDGF-BB protein production has been observed to be increased in the bile duct segment, biliary epithelial cells, infiltrating macrophages and hepatic stellate cells (Kinnman et al., 2000, Lab. Invest. 80: 697-707; Grappone et al., 1999, J. Hepatol. 31:100-109; Bonner, J C, 2004, Cytokine Growth Factor Rev. 15: 255-273). More recently, antibody inhibition of PDGF-B/PDGF-Rβ receptor binding reduced development of liver fibrosis (Ogawa et al., 2010, Hepatol. Res. 40:1128-1141) demonstrating the role of PDGF-B signaling in liver fibrosis.

PDGF-BB-induced signaling via PDGFRβ strongly promotes hepatic stellate cell proliferation, migration and phenotypic change into myofibroblasts, followed by collagen deposition and fibrogenesis (Kinnman et al., 2001, Lab. Invest. 81:1709-1716; Kinnman et al., 2003, Lab. Invest. 83:163-173). Inhibition of the effects of PDGF-B by antisense, blocking mAbs, dominant-negative soluble PDGFRβ or imatinib (STI571, Gleevec®, Glivec®), an inhibitor of tyrosine kinases including both PDGFRs α and β, reduced hepatic hydroxyproline content as well as mRNA expressions of PDGF-B, PDGFRβ, and collagen type 1 in a BDL induced liver fibrosis model in rats (Ogawa et al., 2010, Hepatol. Res. 40:1128-1141; Kinnman et al., 2000, Lab. Invest. 80: 697-707; Kinnman et al., 2001, Lab. Invest. 81:1709-1716; Kinnman et al., 2003, Lab. Invest. 83: 163-173; Borkham et al., 2004, Biochem. Biophys. Res. Commun. 321:413-423; Borkham et al., 2004, Lab. Invest. 84:766-777; Neef et al., 2006, J. Hepatol. 44:167-175).

Taken together the data observed in pre-clinical fibrosis models, especially renal and liver models, underscores the important potential therapeutic effect mediated by inhibiting PDGF-B/PDGFRβ binding and/or signaling to limit undesirable extracellular matrix deposition and to retain organ function.

In sum, fibrotic diseases and disorders mediated by PDGF-AB and/or PDGF-BB signaling via the interaction of these ligands comprising PDGF-B with the PDGFRβ exact a heavy toll on human mortality and morbidity. Therefore, there is a long-felt need for novel potential therapeutics to treat or ameliorate these diseases/disorders, and the present invention meets this need.

SUMMARY OF THE INVENTION

The invention includes an isolated antibody, or antigen-binding fragment thereof, that specifically binds PDGF-B and comprises a heavy chain variable region ($V_H$) comprising a $V_H$ complementarity determining region one (CDR-H1), CDR-H2, and CDR-H3 of the VH amino acid sequence of SEQ ID NO: 6; and a light chain variable region ($V_L$) comprising a VL CDR1 (CDR-L1), CDR-L2, and CDR-L3 of the VL amino acid sequence of SEQ ID NO:4.

In one aspect, the antibody comprises a $V_H$ comprising a CDR-H2, and CDR-H3 of the $V_H$ amino acid sequence of SEQ ID NO: 6; and a $V_L$ comprising a CDR-L1, CDR-L2, and CDR-L3 of the $V_L$ amino acid sequence of SEQ ID NO:4.

In another aspect, the antibody comprises a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:12.

In yet another aspect, the antibody comprises a $V_H$ comprising the CDR-H2 amino acid sequence of SEQ ID NO:8, and the CDR-H3 amino acid sequence of SEQ ID NO: 9, and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:12.

In yet a further aspect, the antibody comprises a $V_H$ comprising a CDR-H1, CDR-H2, and CDR-H3 of the $V_H$ amino acid sequence encoded by the polynucleotide insert of the vector deposited as MOR8457-GL-VH (ATCC accession number PTA-13303), and a light chain variable region ($V_L$) comprising a CDR-L1, CDR-L2, and CDR-L3 of the $V_L$ amino acid sequence encoded by the polynucleotide insert of the vector deposited as MOR8457-GL-VL (ATCC accession number PTA-13302).

In one aspect, the antibody comprises a $V_H$ comprising a CDR-H2 and CDR-H3 of a $V_H$ amino acid sequence encoded by the polynucleotide insert of the vector deposited as MOR8457-GL-VH (ATCC accession number PTA-13303), and a $V_L$ comprising a CDR-L1, CDR-L2, and CDR-L3 of the VL amino acid sequence encoded by the polynucleotide insert of the vector deposited as MOR8457-GL-VL (ATCC accession number PTA-13302).

In another aspect, the antibody comprises a $V_H$ comprising the amino acid sequence of SEQ ID NO: 2 and a $V_L$ comprising the amino acid sequence of SEQ ID NO:1.

In another aspect, the antibody comprises a $V_H$ comprising the amino acid sequence of SEQ ID NO: 6 and a $V_L$ comprising the amino acid sequence of SEQ ID NO:4.

In yet another aspect, the antibody comprises a $V_H$ comprising the amino acid sequence of SEQ ID NO: 6 and a $V_L$ comprising the amino acid sequence of SEQ ID NO:1.

In a further aspect, the antibody comprises a $V_H$ comprising the amino acid sequence of SEQ ID NO: 2 and a $V_L$ comprising the amino acid sequence of SEQ ID NO:4.

In yet another aspect, the antibody comprises a heavy chain comprising the sequence of SEQ ID NO:14 and a light chain comprising the amino acid sequence of SEQ ID NO:16.

In one aspect, the antibody comprises a $V_H$ comprising a CDR-H1, CDR-H2 and CDR-H3 encoded by the nucleic acid sequence of SEQ ID NO:5, and a $V_L$ CDR-L1, CDR-L2 and CDR-L3 encoded by the nucleic acid sequence of SEQ ID NO:3.

In another aspect, the antibody comprises a $V_H$ comprising a CDR-H2 and CDR-H3 encoded by the nucleic acid sequence of SEQ ID NO:5, and a $V_L$ CDR-L1, CDR-L2 and CDR-L3 encoded by the nucleic acid sequence of SEQ ID NO:3.

In yet another aspect, the antibody comprises a $V_H$ encoded by the nucleic acid sequence of SEQ ID NO:5, and a $V_L$ encoded by the nucleic acid sequence of SEQ ID NO:3.

In a further aspect, the antibody comprises a heavy chain encoded by the nucleic acid sequence of SEQ ID NO:13, and a light chain encoded by the nucleic acid sequence of SEQ ID NO:15.

In another aspect, the antibody comprises a $V_H$ comprising a CDR-H1, CDR-H2, and CDR-H3 of the $V_H$ amino acid sequence of SEQ ID NO:44, and a $V_L$ comprising a CDR-L1, CDR-L2, and CDR-L3 of the VL amino acid sequence of SEQ ID NO:39.

In a further aspect, the antibody comprises a $V_H$ comprising a CDR-H2 and CDR-H3 of the $V_H$ amino acid sequence of SEQ ID NO:44, and a $V_L$ comprising a CDR-L1, CDR-L2, and CDR-L3 of the VL amino acid sequence of SEQ ID NO:39.

In yet another aspect, the antibody comprises $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:41, and the CDR-L3 amino acid sequence of SEQ ID NO:12.

In another aspect, the antibody comprising $V_H$ comprising the CDR-H2 amino acid sequence of SEQ ID NO:8 and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:41, and the CDR-L3 amino acid sequence of SEQ ID NO:12.

In one aspect, the antibody comprises a $V_H$ comprising the amino acid sequence of SEQ ID NO:44; and a $V_L$ comprising the amino acid sequence of SEQ ID NO:39.

In yet another aspect, the antibody comprises a heavy chain comprising the sequence of SEQ ID NO:46, and a light chain comprising the amino acid sequence of SEQ ID NO:42.

In one aspect, the antibody comprises a $V_H$ comprising a CDR-H1, CDR-H2, and CDR-H3 of the $V_H$ amino acid sequence of SEQ ID NO:44; and a $V_L$ comprising a CDR-L1, CDR-L2, and CDR-L3 of the VL amino acid sequence of SEQ ID NO:34.

In a further aspect, the antibody comprises a $V_H$ comprising a CDR-H2 and CDR-H3 of the $V_H$ amino acid sequence of SEQ ID NO:44; and a $V_L$ comprising a CDR-L1, CDR-L2, and CDR-L3 of the VL amino acid sequence of SEQ ID NO:34.

In another aspect, the antibody comprises a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:36.

In a further aspect, the antibody comprises a $V_H$ comprising the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:36.

In yet another aspect, the antibody comprises a $V_H$ comprising the amino acid sequence of SEQ ID NO:44; and a $V_L$ comprising the amino acid sequence of SEQ ID NO:34.

In a further aspect, the antibody comprises a heavy chain comprising the sequence of SEQ ID NO:46, and a light chain comprising the amino acid sequence of SEQ ID NO:37.

The invention includes an isolated nucleic acid encoding an antibody, or antigen-binding fragment thereof, wherein the antibody comprises a heavy chain variable region ($V_H$) comprising a $V_H$ complementarity determining region one (CDR-H1), CDR-H2, and CDR-H3 of the VH amino acid sequence of SEQ ID NO: 6; and a light chain variable region ($V_L$) comprising a VL CDR1 (CDR-L1), CDR-L2, and CDR-L3 of the VL amino acid sequence of SEQ ID NO:4.

In one aspect, the nucleic acid encodes an antibody comprising a $V_H$ comprising a CDR-H2, and CDR-H3 of the $V_H$ amino acid sequence of SEQ ID NO: 6; and a $V_L$ comprising a CDR-L1, CDR-L2, and CDR-L3 of the $V_L$ amino acid sequence of SEQ ID NO:4.

In another aspect, the nucleic acid encodes an antibody comprising a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:12.

In yet another aspect, the nucleic acid encodes an antibody comprising a $V_H$ comprising the CDR-H2 amino acid sequence of SEQ ID NO:8, and the CDR-H3 amino acid sequence of SEQ ID NO: 9, and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:12.

In yet a further aspect, the nucleic acid encodes an antibody comprising a $V_H$ comprising a CDR-H1, CDR-H2, and CDR-H3 of the $V_H$ amino acid sequence encoded by the polynucleotide insert of the vector deposited as MOR8457-GL-VH (ATCC accession number PTA-13303), and a light chain variable region ($V_L$) comprising a CDR-L1, CDR-L2, and CDR-L3 of the $V_L$ amino acid sequence encoded by the polynucleotide insert of the vector deposited as MOR8457-GL-VL (ATCC accession number PTA-13302).

In one aspect, the nucleic acid encodes an antibody comprising a $V_H$ comprising a CDR-H2 and CDR-H3 of a $V_H$ amino acid sequence encoded by the polynucleotide insert of the vector deposited as MOR8457-GL-VH (ATCC accession number PTA-13303), and a $V_L$ comprising a CDR-L1, CDR-L2, and CDR-L3 of the VL amino acid sequence encoded by the polynucleotide insert of the vector deposited as MOR8457-GL-VL (ATCC accession number PTA-13302).

In another aspect, the nucleic acid encodes an antibody comprising a $V_H$ comprising the amino acid sequence of SEQ ID NO: 2 and a $V_L$ comprising the amino acid sequence of SEQ ID NO:1.

In another aspect, the nucleic acid encodes an antibody comprising a $V_H$ comprising the amino acid sequence of SEQ ID NO: 6 and a $V_L$ comprising the amino acid sequence of SEQ ID NO:4.

In yet another aspect, the nucleic acid encodes an antibody comprising a $V_H$ comprising the amino acid sequence of SEQ ID NO: 6 and a $V_L$ comprising the amino acid sequence of SEQ ID NO:1.

In a further aspect, the nucleic acid encodes an antibody comprising a $V_H$ comprising the amino acid sequence of SEQ ID NO: 2 and a $V_L$ comprising the amino acid sequence of SEQ ID NO:4.

In yet another aspect, the nucleic acid encodes an antibody comprising a heavy chain comprising the sequence of SEQ ID NO:14 and a light chain comprising the amino acid sequence of SEQ ID NO:16.

In another aspect, the nucleic acid encodes an antibody comprising a $V_H$ comprising a CDR-H1, CDR-H2, and CDR-H3 of the $V_H$ amino acid sequence of SEQ ID NO:44, and a $V_L$ comprising a CDR-L1, CDR-L2, and CDR-L3 of the VL amino acid sequence of SEQ ID NO:39.

In a further aspect, the nucleic acid encodes an antibody comprising a $V_H$ comprising a CDR-H2 and CDR-H3 of the $V_H$ amino acid sequence of SEQ ID NO:44, and a $V_L$ comprising a CDR-L1, CDR-L2, and CDR-L3 of the VL amino acid sequence of SEQ ID NO:39.

In yet another aspect, the nucleic acid encodes an antibody comprising a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:41, and the CDR-L3 amino acid sequence of SEQ ID NO:12.

In another aspect, the nucleic acid encodes an antibody comprising a $V_H$ comprising the CDR-H2 amino acid sequence of SEQ ID NO:8 and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:41, and the CDR-L3 amino acid sequence of SEQ ID NO:12.

In one aspect, the nucleic acid encodes an antibody comprising a $V_H$ comprising the amino acid sequence of SEQ ID NO:44; and a $V_L$ comprising the amino acid sequence of SEQ ID NO:39.

In yet another aspect, the nucleic acid encodes an antibody comprising a heavy chain comprising the sequence of SEQ ID NO:46, and a light chain comprising the amino acid sequence of SEQ ID NO:42.

In one aspect, the nucleic acid encodes an antibody comprising a $V_H$ comprising a CDR-H1, CDR-H2, and CDR-H3 of the $V_H$ amino acid sequence of SEQ ID NO:44; and a $V_L$ comprising a CDR-L1, CDR-L2, and CDR-L3 of the VL amino acid sequence of SEQ ID NO:34.

In a further aspect, the nucleic acid encodes an antibody comprising a $V_H$ comprising a CDR-H2 and CDR-H3 of the $V_H$ amino acid sequence of SEQ ID NO:44; and a $V_L$ comprising a CDR-L1, CDR-L2, and CDR-L3 of the VL amino acid sequence of SEQ ID NO:34.

In another aspect, the nucleic acid encodes an antibody comprising a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:36.

In a further aspect, the nucleic acid encodes an antibody comprising a $V_H$ comprising the CDR-H2 amino acid sequence of SEQ ID NO:8 and the CDR-H3 amino acid sequence of SEQ ID NO: 9; and a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:36.

In yet another aspect, the nucleic acid encodes an antibody comprising a $V_H$ comprising the amino acid sequence of SEQ ID NO:44; and a $V_L$ comprising the amino acid sequence of SEQ ID NO:34.

In a further aspect, the antibody comprises a heavy chain comprising the sequence of SEQ ID NO:46, and a light chain comprising the amino acid sequence of SEQ ID NO:37.

In one aspect, the nucleic acid encodes an antibody comprising a $V_H$ comprising a CDR-H1, CDR-H2 and CDR-H3 encoded by the nucleic acid sequence of SEQ ID NO:5, and a $V_L$ CDR-L1, CDR-L2 and CDR-L3 encoded by the nucleic acid sequence of SEQ ID NO:3.

In another aspect, the nucleic acid encodes an antibody comprising a $V_H$ comprising a CDR-H2 and CDR-H3 encoded by the nucleic acid sequence of SEQ ID NO:5, and a $V_L$ CDR-L1, CDR-L2 and CDR-L3 encoded by the nucleic acid sequence of SEQ ID NO:3.

In yet another aspect, the nucleic acid encodes an antibody comprising a $V_H$ encoded by the nucleic acid sequence of SEQ ID NO:5, and a $V_L$ encoded by the nucleic acid sequence of SEQ ID NO:3.

In a further aspect, the nucleic acid encodes an antibody comprising a heavy chain encoded by the nucleic acid sequence of SEQ ID NO:13, and a light chain encoded by the nucleic acid sequence of SEQ ID NO:15.

The invention includes an isolated nucleic acid encoding an antibody, or antigen-binding fragment thereof, that specifically binds PDGF-B, wherein the nucleic acid comprises the nucleic acid sequence of SEQ ID NO:3.

In one aspect, the nucleic acid comprises the nucleic acid sequence of SEQ ID NO:5.

In another aspect, the nucleic acid comprises the nucleic acid sequence of SEQ ID NO:13.

In yet another aspect, the nucleic acid comprises the nucleic acid sequence of SEQ ID NO:15.

In a further aspect, the nucleic acid comprises the nucleic acid sequence of SEQ ID NO:3 and the nucleic acid sequence of SEQ ID NO:5.

In another aspect, the nucleic acid comprises the nucleic acid sequence of SEQ ID NO:13 and the nucleic acid sequence of SEQ ID NO:15.

In yet another aspect, the nucleic acid comprises the nucleic acid sequence of the insert of the vector deposited as MOR8457-GL-VH having ATCC accession number PTA-13303.

In another aspect, the nucleic acid comprises the nucleic acid sequence of the insert of the vector deposited as MOR8457-GL-VL having ATCC accession number PTA-13302.

In one aspect, the nucleic acid encodes an antibody comprising a $V_H$ comprising a CDR-H1, CDR-H2 and CDR-H3 encoded by the nucleic acid sequence of SEQ ID NO:45, and a $V_L$ CDR-L1, CDR-L2 and CDR-L3 encoded by the nucleic acid sequence of SEQ ID NO:35.

In another aspect, the nucleic acid encodes an antibody comprising a $V_H$ comprising a CDR-H2 and CDR-H3 encoded by the nucleic acid sequence of SEQ ID NO:45, and a $V_L$ CDR-L1, CDR-L2 and CDR-L3 encoded by the nucleic acid sequence of SEQ ID NO:35.

In yet another aspect, the nucleic acid encodes an antibody comprising a $V_H$ encoded by the nucleic acid sequence of SEQ ID NO:45, and a $V_L$ encoded by the nucleic acid sequence of SEQ ID NO:35.

In a further aspect, the nucleic acid encodes an antibody comprising a heavy chain encoded by the nucleic acid sequence of SEQ ID NO:47, and a light chain encoded by the nucleic acid sequence of SEQ ID NO:38.

In one aspect, the nucleic acid encodes an antibody comprising a $V_H$ comprising a CDR-H1, CDR-H2 and CDR-H3 encoded by the nucleic acid sequence of SEQ ID NO:45, and a $V_L$ CDR-L1, CDR-L2 and CDR-L3 encoded by the nucleic acid sequence of SEQ ID NO:40.

In another aspect, the nucleic acid encodes an antibody comprising a $V_H$ comprising a CDR-H2 and CDR-H3 encoded by the nucleic acid sequence of SEQ ID NO:45, and a $V_L$ CDR-L1, CDR-L2 and CDR-L3 encoded by the nucleic acid sequence of SEQ ID NO:40.

In yet another aspect, the nucleic acid encodes an antibody comprising a $V_H$ encoded by the nucleic acid sequence of SEQ ID NO:45, and a $V_L$ encoded by the nucleic acid sequence of SEQ ID NO:40.

In a further aspect, the nucleic acid encodes an antibody comprising a heavy chain encoded by the nucleic acid sequence of SEQ ID NO:47, and a light chain encoded by the nucleic acid sequence of SEQ ID NO:43.

In a further aspect, the nucleic acid comprises the nucleic acid sequence of SEQ ID NO:35.

In another aspect, the nucleic acid comprises the nucleic acid sequence of SEQ ID NO:40.

In one aspect, the nucleic acid comprises the nucleic acid sequence of SEQ ID NO:45;

In another aspect, the nucleic acid comprises the nucleic acid sequence of SEQ ID NO:38.

In yet another aspect, the nucleic acid comprises the nucleic acid sequence of SEQ ID NO:43.

In a further aspect, the nucleic acid comprises the nucleic acid sequence of SEQ ID NO:47.

In another aspect, the nucleic acid comprises the nucleic acid sequence of SEQ ID NO:35 and SEQ ID NO:45.

In one aspect, the nucleic acid comprises the nucleic acid sequence of SEQ ID NO:40 and SEQ ID NO:45.

In a further aspect, the nucleic acid comprises the nucleic acid sequence of SEQ ID NO:38 and SEQ ID NO:47.

In yet another aspect, the nucleic acid comprises the nucleic acid sequence of SEQ ID NO:43 and SEQ ID NO:47.

In one aspect, the invention includes a host cell comprising the nucleic acid.

In one aspect, the invention includes a vector comprising the nucleic acid.

In another aspect, the invention includes a host cell comprising the vector.

In yet another aspect, the host cell is a bacterial cell or a mammalian cell.

The invention includes a method of producing the antibody, or antigen-binding fragment thereof, that specifically binds PDGF-B, said method comprising culturing the host cell under conditions wherein the antibody is expressed, and further comprising isolating the antibody.

The invention includes an isolated antibody, or antigen-binding fragment thereof, of claim 1, wherein the $V_L$ comprises the amino acid sequence of SEQ ID NO:4 and further comprises at least one amino acid substitution in an amino acid not within a CDR.

In another aspect, the antibody comprises a $V_H$ comprising the amino acid sequence of SEQ ID NO:6 and further comprises at least one amino acid substitution in an amino acid not within a CDR.

In yet another aspect, the antibody comprises a $V_L$ comprising the amino acid sequence of SEQ ID NO:4 and further comprises at least one amino acid substitution in an amino acid not within a CDR, and a $V_H$ comprising the amino acid sequence of SEQ ID NO:6 and further comprises at least one amino acid substitution in an amino acid not within a CDR.

The invention includes an isolated antibody, or antigen-binding fragment thereof, that specifically binds PDGF-B, wherein the antibody binds the same epitope as an antibody disclosed herein, or overlaps with the binding site on PDGFRββ for PDGF-B as an antibody disclosed herein, and wherein said antibody is not AbyD3263.

The invention includes an isolated antibody, or antigen-binding fragment thereof, that specifically binds PDGF-B, wherein the antibody cross-competes with PDGFRββ for binding to PDGF-B and further wherein the antibody binds PDGF-B with a $K_D$ ranging from 2 pM to 100 pM.

In one aspect, the antibody binds at least one epitope on PDGF-BB wherein the epitope is selected from group consisting of:

an epitope comprising residues Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86, with respect to the amino acid sequence of SEQ ID NO:33; and an epitope comprising residues Trp 40, Asn 54, Glu 71, Arg 73, Ile 75, Glu 76, Ile 77, Arg 79, Lys 80, Lys 81, Pro 82, Ile 83, Phe 84, Lys 85 and Lys 86, with respect to the amino acid sequence SEQ ID NO:33.

In another aspect, the antibody comprises a paratope, wherein the paratope comprises at least one amino acid selected from the group consisting of: amino acid residues G28, S29, Y30, F31, D49, D50, F90, T91, H92, N93, S94 based on Kabat numbering with respect to the sequence of SEQ ID NO:1 and amino acid residues Y50, L57, Y59, Y60, D62, W102, Y103, G104, G105 based on Kabat numbering with respect to the sequence of SEQ ID NO:2.

In another aspect, the paratope can further comprise the amino acid residue N65 based on Kabat numbering with respect to the sequence of SEQ ID NO:1 and/or residue W47 based on Kabat numbering with respect to the sequence of SEQ ID NO:2.

The invention includes an isolated antibody, or antigen-binding fragment thereof, wherein the antibody specifically binds PDGF-B with a $K_D$ ranging from about 2 pM to 69 pM, cross-competes with PDGFRβ for binding to PDGF-B, and inhibits an activity mediated by PDGF-B binding to PDGFβ.

In one aspect, the activity mediated by PDGF-B binding to PDGFβ is at least one selected from the group consisting of phosphorylation of said PDGFβ, induction of cell proliferation, induction of cell migration, and increase deposition of extracellular matrix.

The invention includes an isolated antibody, or antigen-binding fragment thereof, that specifically binds human PDGF-BB with a $K_D$ of about 13 pM, wherein the antibody:

(a) cross-competes with PDGFββ for binding to PDGF-BB;

(b) binds to at least one epitope selected from the group consisting of (i) an epitope comprising residues Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86, with respect to the amino acid sequence of SEQ ID NO:33; and (ii) an epitope comprising residues Trp 40, Asn 54, Glu 71, Arg 73, Ile 75, Glu 76, Ile 77, Arg 79, Lys 80, Lys 81, Pro 82, Ile 83, Phe 84, Lys 85 and Lys 86, with respect to the amino acid sequence SEQ ID NO:33;

wherein said epitopes are approximately 190 Å apart on PDGF-BB;

(c) comprises a paratope comprising amino acid residues G28, S29, Y30, F31, D49, D50, F90, T91, H92, N93, S94 based on Kabat numbering with respect to the sequence of SEQ ID NO:1 and amino acid residues Y50, L57, Y59, Y60, D62, W102, Y103, G104, G105 based on Kabat numbering with respect to the sequence of SEQ ID NO:2; and (d) wherein the amino acid residues of said paratope contact, within 4 Å, the amino acid residues of one said epitope as follows:

(i) for the light chain variable domain Trp 47 contacts Lys 82 of PDGF-B, Leu 57 contacts Ile 77 of PDGF-B, Tyr 59 contacts Ile 77, Arg 79, Lys 80, Lys 81, and Pro 82 of PDGF-B; Trp 102 contacts Leu 8, Val 39, Trp 40, Asn 54, Arg 56, Ile 75, and Phe 84 of PDGF-B, Tyr 103 contacts Trp 40, Arg 73, Ile 75, and Phe 84 of PDGF-B, Gly 104 contacts Arg 73 and Phe 84 of PDGF-B, and Gly 105 contacts Phe 84 of PDGF-B, wherein the numbering of the light chain variable domain amino acids is based on Kabat numbering with respect to SEQ ID NO:1; and (ii) for the heavy chain variable domain Gly 28 contacts Lys 86 of PDGF-B, Ser 29 contacts Lys 85 and Lys 86 of PDGF-B, Tyr 30 contacts Ile 83, Phe 84, Lys 85 and Lys 86 of PDGF-B, Phe 31 contacts Gln 71, Arg 73, Phe 84 and Lys 86 of PDGF-B, Asp 49 contacts Arg 73 of PDGF-B, Asp 50 contacts Lys 86 of PDGF-B, Asn 65 contacts Lys 86 of PDGF-B, Phe 90 contacts Pro 82, Ile 83, and Phe 84 of PDGF-B, Thr 91 contacts Lys 81 and Ile 83 of PDGF-B, His 92 contacts Lys 81 and Ile 83 of PDGF-B, Asn 93 contacts Lys 81 of PDGF-B, and Ser 94 contacts Lys 81 of PDGF-B, wherein numbering of the heavy chain variable domain amino acids is based on Kabat numbering with respect to SEQ ID NO:2;

and further wherein amino acid residue numbering of PDGF-B contact residues is with respect to the amino acid sequence of SEQ ID NO:33.

The invention includes a pharmaceutical composition comprising an antibody, or antigen-binding fragment thereof, of the invention, and a pharmaceutically acceptable carrier or excipient.

The invention includes a method for reducing deposition of extracellular matrix in a subject in need thereof. The method comprises administering to the subject an effective amount of the pharmaceutical composition, thereby inhibiting excessive deposition of extracellular matrix in the subject.

The invention further includes the use of an antibody, or antigen binding fragment thereof, or a pharmaceutical composition of the invention in the manufacture of a medicament for use in reducing deposition of extracellular matrix in a subject in need thereof.

The invention further provides an antibody, or antigen binding fragment thereof, or a pharmaceutical composition of the invention for use in reducing deposition of extracellular matrix in a subject in need thereof.

The invention includes method for preventing or treating a disease, disorder or condition mediated by PDGF-B binding to PDGFRβ. The method comprises administering to a subject in need thereof an effective amount of the pharmaceutical composition.

The invention further provides the use of an antibody, or antigen binding fragment thereof, or a pharmaceutical composition of the invention in the manufacture of a medicament for preventing or treating a disease, disorder or condition mediated by PDGF-B binding to PDGFRβ.

The invention further provides an antibody, or antigen binding fragment thereof, or a pharmaceutical composition of the invention for preventing or treating a disease, disorder or condition mediated by PDGF-B binding to PDGFRβ.

In one aspect, the disease, disorder or condition is at least one selected from the group consisting of: atherosclerosis, restenosis, pulmonary hypertension, retinal vascular disease, cardiac fibrosis, lung fibrosis, liver fibrosis, kidney fibrosis, systemic sclerosis, rheumatoid arthritis, osteoarthritis, and tumorigenesis.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s) which are presently preferred. It should be understood, however, that the invention is not limited to the precise arrangements and instrumentalities shown.

In the drawings:

FIG. 1, comprising panels A through N, depicts the sequence alignment of the MOR-8457 heavy chain variable region (FIG. 1A) and light chain variable region (FIG. 1B) with the closest four respective germline V regions in the IMGT database. Identical residues are shown as (.), and the frameworks and CDR1 and CDR2 are indicated. FIG. 1C sets out the amino acid sequence of MOR8457-VL without germlining (SEQ ID NO:1), and the CDRs are underlined. FIG. 1D sets out the amino acid sequence of MOR8457-VH without germlining (SEQ ID NO:2), and the CDRs are underlined. FIG. 1E sets out the amino acid sequence of MOR8457-GL-VL after germlining (SEQ ID NO:4), and the CDRs are underlined. FIG. 1F sets out the amino acid sequence of MOR8457-GL-VH after germlining (SEQ ID NO:6), and the CDRs are underlined. FIG. 1G sets out the amino acid sequence of MOR8457-GL-LC (SEQ ID NO:16) full length light chain wherein the VL region has been germlined. FIG. 1H sets out the amino acid sequence of MOR8457-GL-hIgG1-3m-HC (SEQ ID NO:14) full length heavy chain comprising a germlined VH region and human IgG1 comprising an effector null triple mutation (3m) wherein the wild type sequence "LLGL" has been mutated to "AAGA". The sites of the leucine to alanine substitutions are underlined. FIG. 1I sets out the amino acid sequence of the light chain variable domain of the engineered variant MOR8457-15-VL (SEQ ID NO:34), with the CDRs underlined. FIG. 1J sets out the amino acid sequence of the heavy chain variable domain of the engineered variants MOR8457-15-VH and MOR8457-16-VH (SEQ ID NO:44), with the CDRs underlined Both engineered variants MOR8457-15 and MOR8457-16 share the same heavy chain sequence. FIG. 1K sets out the amino acid sequence of the light chain variable domain of the engineered variant MOR8457-16-VL (SEQ ID NO:39), with the CDRs underlined. FIG. 1L sets out the amino acid sequence of MOR8457-15 (SEQ ID NO:37) full length light chain wherein the VL region has been engineered for improved biophysical properties. FIG. 1M sets out the amino acid sequence of the full length heavy chain of MOR8457-15-HC and MOR8457-16-HC (SEQ ID NO:46) comprising an engineered VH region and human IgG1 comprising an effector null triple mutation (3m) wherein the VH region has been engineered for improved biophysical properties and the constant region wild type sequence "LLGL" has been mutated to "AAGA". The sites of the leucine to alanine substitutions are underlined. FIG. 1N sets out the amino acid sequence of MOR8457-16-LC (SEQ ID NO:42) full length light chain wherein the VL region has been engineered for improved biophysical properties.

FIG. 5A shows a diagram illustrating the Biacore set up of the competition assay in solution. MOR8457-mIgG1 was serially diluted in PBS then mixed with 1 mM of human PDGF-BB and incubated for 20 hours at 2-8° C. to reach equilibrium as indicated by the [brackets]. Each MOR8457-mIgG1 and PDGF-BB dilution mixture was then injected over the surface of PDGFRβ-hIgG1 captured by anti-human IgG1 on a CM5 chip. FIG. 5B depicts a graph showing a concentration response curve demonstrating that MOR8457 inhibited binding of PDGF-BB to PDGFRβ-hIgG1. Data shown are from one representative experiment of two independent experiments.

FIG. 8, comprising panels A and B, depicts two graphs showing that MOR8457 potently inhibited PDGF-BB induced human mesangial cell proliferation. FIG. 8A depicts a graph showing a concentration response curve of PDGF-BB induced human mesangial cell proliferation in the absence of MOR8457. Primary human mesangial cells were cultured and seeded in 96-well plates. Cells were growth-arrested for 24 hours with serum-free MCM media. After 24 hours, the cells were stimulated with serially diluted PDGF-BB for 4 hours at 37° C. DNA synthesis was determined during the last 16 hours using a BrdU incorporation assay. PDGF-BB potently induced the mesangial cell proliferation with $EC_{50}$ of 2.3 ng/mL. FIG. 8B depicts a graph showing a representative inhibition curve of MOR8457 in the same assay shown in FIG. 8A. That is, MOR8457-IKR-IgG1-3m was half-log diluted from 100 nM down to 0.1 nM then mixed with 2.5 ng/ml of PDGF-BB in serum-free MCM media for 30 minutes before the mixture was added to the cells. The proliferation assay was performed as described in FIG. 8A. The average $IC_{50}$ determined from three independent experiments was 13.4±2.8 µM and maximum inhibition was 87.9±5.7%.

FIG. 9A depicts a graph showing the concentration response curve of PDGF-BB in the absence and presence of 0.01, 0.1, 1 and 10 nM of MOR8457-IKR-IgG1-3m. Antibodies were mixed with PDGF-BB and incubated for 2.5 hours at 25° C. before the mixture was added to the cells. The cell proliferation assay was performed as described in FIG. 8. FIG. 9A shows that the curves shifted to the right with the increased concentration of MOR8457-IKR-IgG1-3m and the extent of the inhibition was surmountable at high concentration of PDGF-BB, suggesting the inhibition is competitive. FIG. 9B depicts a graph showing a Schild regression analysis. Schild analysis was performed as described (Arunklakshana & Schild, 1959, Br. J. Pharmacol. 65:48-58). The $EC_{50}$ of PDGF-BB measured in the absence and presence of antibodies was used to calculate the dose ratio (DR). A series of log(DR-1) values for a series of log [B] antibody concentrations was plotted on the graph. The $pA_2$ deduced from the graph was about 20 pM, which is consistent with the binding affinity as measured by Biacore (i.e., about 13 pM). These data show that MOR8457 is a potent and competitive inhibitor in the functional assay.

DETAILED DESCRIPTION OF THE INVENTION

Figure 2:
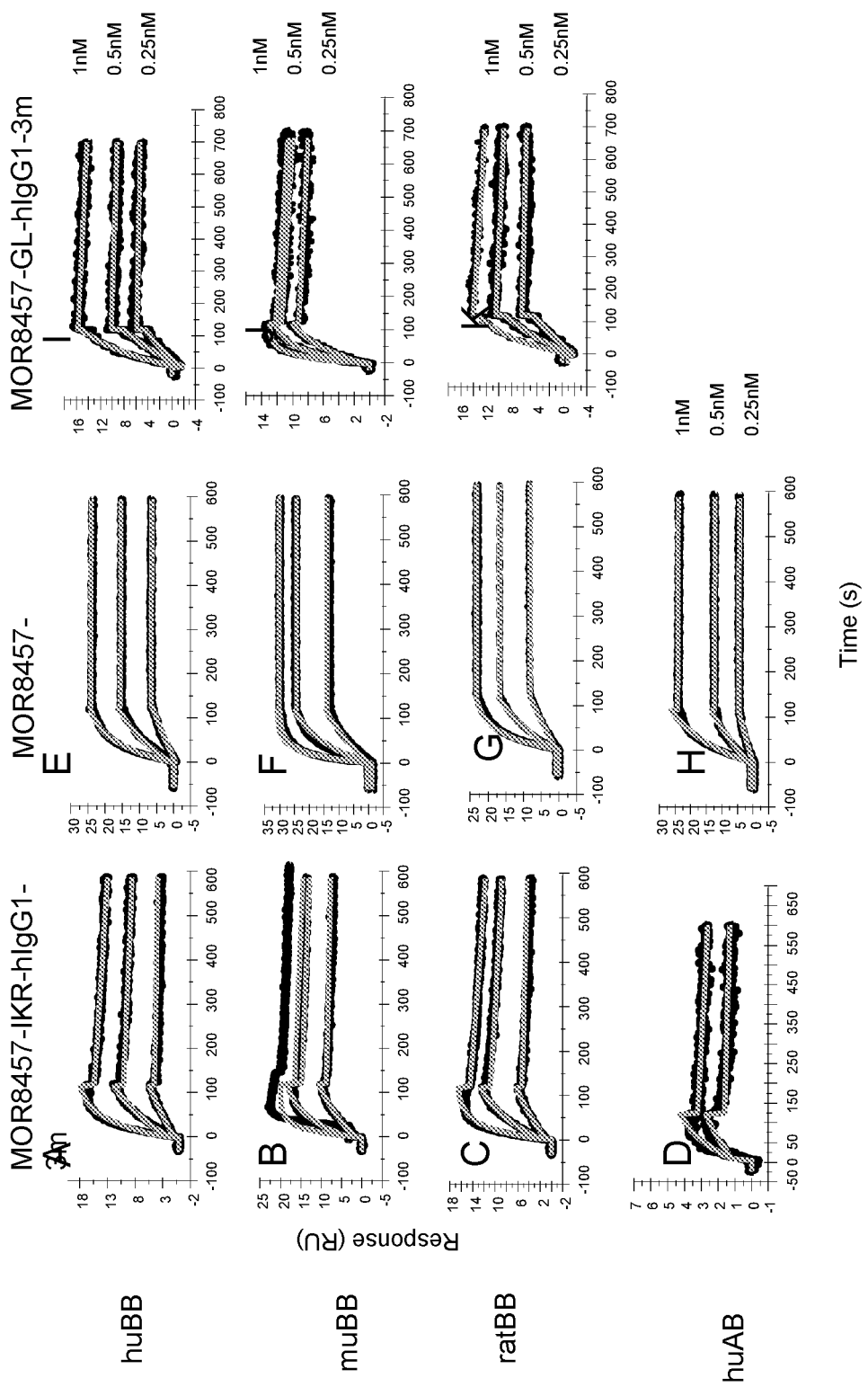
FIG. 2, comprising panels A through K, depicts Biacore sensorgrams showing the binding kinetics of MOR8457 antibodies to different PDGFs. Anti-human (A-D, I-K) or anti-mouse (E-H) IgG antibodies were immobilized in flow cells of CM5 sensor chips. 1 µg/mL of MOR8457-IKR-hIgG1-3m (A-D), MOR8457-mIgG1 (E-H) or MOR8457-GL-hIgG1-3m (I-K) was injected independently over the respective anti-human or anti-mouse surface for 10 seconds resulting in a stable anti-PDGF surface between 50-100 RU. Different concentration of PDGF proteins, 0.25, 0.5, and 1 nM, was then injected over the antibody surface for 2 minutes at a flow rate of 100 µl/min for binding. The complex was allowed to dissociate for 10 minutes. The surface was regenerated with a 30 second injection of 10 mM magnesium chloride leaving the surface ready for another round of anti-PDGF antibody capture and PDGF binding kinetics. Each of these three antibodies bound tightly to human (A, E, I), mouse (B, F, J) and rat (C, G, K) PDGF-BB. MOR8457-IKR-hIgG1-3m (D) and MOR8457-mIgG1 (H) bound to human PDGF-AB. Each sensorgram shown is one representative of three independent experiments.

Disclosed herein are antibodies that specifically bind to PDGF-B and inhibit its binding to PDGFRβ. Methods of making PDGF-B antibodies, compositions comprising these antibodies, and methods of using these antibodies are provided. PDGF-B antibodies can be used in the prevention and/or treatment of diseases, disorders or conditions caused by and/or associated with PDGF-B binding to PDGFRβ. Such diseases, disorders or conditions include, but are not limited to, atherosclerosis, balloon injury-induced restenosis, pulmonary hypertension, organ fibrosis (e.g., cardiac, lung, renal and kidney), systemic sclerosis, rheumatoid arthritis, osteoarthritis, and tumorigenesis.

General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, N.Y. (1998); Coligan et al., Short Protocols in Protein Science, John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

DEFINITIONS

The following terms, unless otherwise indicated, shall be understood to have the following meanings: the term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', $F(ab')_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more fragments of an antibody that retain the ability to specifically bind to an antigen (e.g., a PDGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123).

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

"Contact residue" as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including fragments or mimics of the molecule used in an immunization process for raising the Ab or in library screening for selecting the Ab. Thus, for antibodies of the invention binding to PDGF-B, full-length PDGF-B from mammalian species (e.g., human, mouse and rat PDGF-B), including both monomers and dimers thereof, as well as truncated and other variants of PDGF-B, are referred to as an antigen.

Generally, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody, or antigen-binding fragment thereof" (Ab), and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to PDGF-B, e.g., the antibodies compete for binding to the antigen.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

The term "antagonist antibody" refers to an antibody that binds to a target and prevents or reduces the biological effect of that target. In some embodiments, the term can denote an antibody that prevents the target, e.g., PDGF-B, to which it is bound from performing a biological function, e.g., binding to its cognate receptors—, PDGFR-αα, PDGFRαβ, and PDGFRββ.

As used herein, an "PDGF-B antagonist antibody" refers to an antibody that is able to inhibit PDGF-B biological activity, or the activity of a homo- or heterodimer comprising PDGF-B (e.g., PDGF-AB and PDGF-BB) and/or downstream event(s) mediated by PDGF-B, including, but not limited to, binding to its cognate tyrosine kinase receptors and mediating signaling thereby and thereby causing, among other things, cell proliferation, migration, and/or extracellular matrix deposition. PDGF-B antagonist antibodies encompass antibodies that block, antagonize, suppress or reduce (to any degree, including significantly) PDGF-B biological activity, including downstream events mediated by PDGF-B, such as, PDGF receptor binding and downstream signaling, induction of cell proliferation and cell migration. For purposes of the present invention, it will be explicitly understood that the term "PDGF-B antagonist antibody" (interchangeably termed "antagonist PDGF-B antibody", "antagonist anti-PDGF-B antibody", "anti-PDGF-B antagonist antibody", "antagonist PDGF-BB antibody", "antagonist anti-PDGF-BB antibody", "anti-PDGF-BB antagonist antibody", "antagonist PDGF-AB antibody", "antagonist anti-PDGF-AB antibody", or "anti-PDGF-AB antagonist antibody") encompasses all the previously identified terms, titles, and functional states and characteristics whereby the PDGF-B itself, a PDGF-B biological activity (including but not limited to its ability to bind a receptor, and induce cell proliferation), or the consequences of the biological activity, are substantially nullified, decreased, or neutralized in any meaningful degree. In some embodiments, a PDGF-B antibody binds PDGF-B and prevents its binding to PDGFRβ. In some embodiments, the antagonist ability is characterized and/or described via a cell growth assay. In some embodiments, the antagonist ability is described in terms of an $IC_{50}$ or $EC_{50}$ value. Examples of PDGF-B antibodies are provided herein.

As used herein, the term "PDGFRβ" encompasses a receptor comprising at least one PDGFRβ polypeptide chain. That is, PDGFRβ, as used herein, includes a single PDGFRβ polypeptide chain, as well as a PDGFRββ homodimer and a PDGFRαβ heterodimer.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, an antibody "interacts with" PDGF-B when the equilibrium dissociation constant is equal to or less than 100 pM, preferably less than about 69 pM, more preferably less than about 50 pM, most preferably less than about 30 pM, more preferably less than about 20 pM, yet more preferably less than about 15 pM, even more preferably less than about 10 pM, even more preferably less than about 4 pM, and more preferably less than about 2 pM, as measured by the methods disclosed herein in Examples 6 and 8. In one embodiment, the antibody interacts with PDGF-B when the $K_D$ ranges from about 69 pM to about 2 pM. In one embodiment, the antibody interacts with PDGF-B with a $K_D$ of about 10 pM.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PDGF-B epitope is an antibody that binds this epitope with greater affinity, avidity, more readily, and/or with greater duration than it binds to other PDGF-B epitopes or non-PDGF-B epitopes. It is also understood by reading this definition that, for example, an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-human tumor antigen antibody that binds a tumor antigen) in a sample, but does not substantially recognize or bind other molecules in the sample, specifically binds to that cognate ligand or binding partner. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (ForteBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) is ≤1 pM, preferably ≤100 nM, more preferably ≤10 nM, even more preferably, ≤100 pM, yet more preferably, ≤10 pM, and even more preferably, ≤1 pM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation, e.g., by the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition binding affinities associated with different molecular interactions, e.g. comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: improved survival rate (reduced mortality), reduction in inflammatory response to the disease, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating" means a lessening or improvement of one or more symptoms as compared to not administering a PDGF-B antibody. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a PDGF-B mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In some embodiments, the individual is considered to be at risk for a disease, disorder or condition mediated by or associated with PDGF-B binding to its receptor and signaling mediated thereby.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Reference to "about" a value or parameter herein includes (and describes) embodiments that are directed to that value or parameter per se. For example, description referring to "about X" includes description of "X." Numeric ranges are inclusive of the numbers defining the range.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

PDGF-B Antibodies

The present invention relates to antibodies that bind to monomeric and/or dimeric PDGF-B. The antibodies preferably specifically bind to PDGF-B, i.e., they bind to PDGF-B but they do not detectably bind, or bind at a lower affinity, to other molecules. In particular, the invention relates to antibodies that bind to PDGF-B and that modulate its activity. For example, an antibody of the invention may have the ability to decrease or inhibit binding of PDGF-B to a cognate PDGFRβ receptor (PDGFRαβ, PDGFRββ, and PDGFRβ-IgG1) and thereby to reduce or inhibit receptor signaling. The invention also relates to compositions comprising such antibodies as well as uses for such antibodies, including therapeutic and pharmaceutical uses.

By the term "PDGF-B" is meant any naturally occurring form of PDGF-B, whether monomeric or dimeric, which may be derived from any suitable organism. The term encompasses any dimer comprising PDGF-B, i.e., PDGF-AB and PDGF-BB. As used herein, "PDGF-B" refers to a mammalian PDGF-B, such as human, rat or mouse, as well as non-human primate, bovine, ovine, or porcine PDGF-B. Preferably, the PDGF-B is human. The term "PDGF-B" also encompasses fragments, variants, isoforms, and other homologs of such PDGF-B molecules. Variant PDGF-B molecules will generally be characterized by having the same type of activity as naturally occurring PDGF-B, such as the ability to bind PDGFRβ, the ability to induce phosphorylation of the receptor, the ability to mediate signaling by such receptor, the ability to induce cell migration or proliferation, and the ability to induce or increase deposition of extracellular matrix.

The antibody of the invention specifically binds PDGF-B (i.e., PDGF-B, PDGF-AB and PDGF-BB) and inhibits its interaction with PDGFRβ, e.g., PDGFRββ and PDGFRαβ, thereby inhibiting PDGF-B activity. By the terms "PDGF-B mediated activity," "PDGF-B mediated effect," "PDGF-B activity," "PDGF-B biological activity" or "PDGF-B function," as used interchangeably herein, is meant any activity mediated by PDGF-B interaction with a cognate receptor including, but not limited to, PDGF-B binding to PDGFRβ, phosphorylation of PDGFRβ, increase in cell migration, increase in cell proliferation, increase in extracellular matrix deposition, and any other activity of PDGF-B either known in the art or to be elucidated in the future.

Thus, the methods of the invention use the antibody of the invention that blocks, suppresses or reduces (including significantly reduces) PDGF-B activity, including downstream events mediated by PDGF-B. A PDGF-B antibody of the invention should exhibit any one or more of the following characteristics: (a) specifically bind to PDGF-B; (b) block PDGF-B interaction with a cell surface receptor and downstream signaling events; (c) block phosphorylation of the PDGFRβ; (d) block PDGF-B mediated induction of cell proliferation; (e) block induction of cell migration; and (f) block or reduce PDGF-B mediated deposition of extracellular matrix.

For purposes of this invention, the antibody preferably reacts with PDGF-B in a manner that blocks PDGF-B interaction with a cell surface receptor, e.g., PDGFRαβ and PDGFRββ.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the PDGF-B antibody is a monoclonal antibody. In some embodiments, the antibody is a human or humanized antibody.

The PDGF-B antibodies of the invention may be made by any method known in the art. General techniques for production of human and mouse antibodies are known in the art and/or are described herein.

PDGF-B antibodies can be identified or characterized using methods known in the art, whereby reduction, amelioration, or neutralization of PDGF-B activity is detected and/or measured. In some embodiments, a PDGF-B antibody is identified by incubating a candidate agent (e.g., PDGFRββ or PDGFRβ-IgG1) with PDGF-B and monitoring binding and/or attendant reduction or inhibition of a biological activity of PDGF-B. The binding assay may be performed with, e.g., purified PDGF-B polypeptide(s), or with cells naturally expressing various receptors, or transfected to express, PDGF-B receptors. In one embodiment, the binding assay is a competitive binding assay, where the ability of a candidate antibody to compete with a known PDGF-B antibody for PDGF-B binding is evaluated. The assay may be performed in various formats, including the ELISA format. In some embodiments, a PDGF-B antibody is identified by incubating a candidate antibody with PDGF-B and monitoring binding. In some embodiments, a PDGF-B is identified by incubating a candidate antibody (e.g. a human anti-PDGF-B antibody) with PDGF-B and monitoring the binding of a second PDGF-B antibody (e.g., a PDGF-B antibody comprising a non-human constant region) to PDGF-B to assess whether one antibody competes for binding of PDGF-B with the second antibody.

Following initial identification, the activity of a candidate PDGF-B antibody can be further confirmed and refined by bioassays, known to test the targeted biological activities. In some embodiments, an in vitro cell assay is used to further characterize a candidate PDGF-B antibody. For example, a candidate antibody is incubated with PDGF-B and a second PDGF-B antibody or soluble PDGFRβ comprising the ectodomain of the receptor (e.g., PDGFRβ-IgG1) is added, and the binding of PDGF-B by the second antibody or soluble receptor is monitored. Alternatively, bioassays can be used to screen candidates directly. Some of the methods for identifying and characterizing PDGF-B antibody are described in detail in the Examples.

The PDGF-B antibodies of the invention exhibit one or more of the following characteristics: (a) specifically bind to PDGF-B; (b) block PDGF-B interaction with a cell surface receptor and downstream signaling events; (c) block PDGF-B mediated induction of cell proliferation or migration; and (d) block or reduce PDGF-B mediated deposition of extracellular matrix. Preferably, PDGF-B antibodies of the invention have two or more of these features. More preferably, the antibodies have three or more of the features. More preferably, the antibodies have all four characteristics.

PDGF-B antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which PDGF-B antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with PDGF-B antibody. In another example, the epitope to which the PDGF-B antibody binds can be determined in a systematic screening by using overlapping peptides derived from the PDGF-B sequence and determining binding by the antibody. According to the gene fragment expression assays, the open reading frame encoding PDGF-B can be fragmented either randomly or by specific genetic constructions and the reactivity of the expressed fragments of PDGF-B with the antibody to be tested is determined. The gene fragments may, for example, be produced by PCR and then transcribed and translated into protein in vitro, in the presence of radioactive amino acids. The binding of the antibody to the radioactively labeled PDGF-B fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant PDGF-B in which various residues of the PDGF-B polypeptide have been replaced with alanine. By assessing binding of the antibody to the mutant PDGF-B, the importance of the particular PDGF-B residues to antibody binding can be assessed.

Yet another method which can be used to characterize a PDGF-B antibody is to use competition assays with other antibodies known to bind to the same antigen, i.e., various fragments on PDGF-B, to determine if the PDGF-B antibody binds to the same epitope as other antibodies. Competition assays are well known to those of skill in the art.

Further, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, Hydroged deuterium exchange Mass Spectrometry (HX-MS) and various competition binding methods. As each method relies on a unique principle, the description of an epitope is intimately linked to the method by which it has been determined. Thus, the epitope for a given antibody/antigen pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g. distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag (e.g. alanine scanning).

In the context of an X-ray derived crystal structure defined by spatial coordinates of a complex between an Ab, e.g., a Fab fragment, and its Ag, the term epitope is herein, unless otherwise specified or contradicted by context, specifically defined as PDGF-B residues characterized by having a heavy atom (i.e. a non-hydrogen atom) within a distance of 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The definition of the term "paratope" is derived from the above definition of "epitope" by reversing the perspective. Thus, the term "paratope" refers to the area or region on the antibody to which an antigen specifically binds, i.e., to which it makes physical contact to the antigen (PDGF-B).

In the context of an X-ray derived crystal structure defined by spatial coordinates of a complex between an antibody, e.g., a Fab fragment or two Fab fragments, and its antigen, the term paratope is herein, unless otherwise specified or contradicted by context, specifically defined as antigen residues characterized by having a heavy atom (i.e., a non-hydrogen atom) within a distance of 4 Å from a heavy atom in PDGF-B.

The epitope and paratope for a given antibody/antigen pair may be identified by routine methods. For example, the general location of an epitope may be determined by assessing the ability of an antibody to bind to different fragments or variant PDGF-B polypeptides as more fully described previously elsewhere herein. The specific amino acids within PDGF-B that make contact with an antibody (epitope) and the specific amino acids in an antibody that make contact with PDGF-B (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

As disclosed herein, such a crystal structure analysis was carried out for the interaction between the MOR8457 antibody, and PDGF-BB dimer. This analysis is described in more detail in the examples.

The paratope of an antibody according to the current invention may be defined as follows: the light chain variable domain of said antibody comprises residues G28, S29, Y30, F31, D49, D50, F90, T91, H92, N93, S94 based on Kabat numbering with respect to the sequence of SEQ ID NO:1, and the heavy chain variable domain of said antibody comprises residues Y50, L57, Y59, Y60, D62, W102, Y103, G104, G105 based on Kabat numbering with respect to the sequence of SEQ ID NO:2.

The paratope of an antibody of the invention can further comprise residue N65 of the light chain variable domain with respect to the sequence of SEQ ID NO:1, and residue W47 of the heavy chain variable domain with respect to the sequence of SEQ ID NO:2.

The light chain variable domain of the antibody according to the current invention may thus comprise amino acid residues:
G, in the position corresponding to position 28,
S, in the position corresponding to position 29,
Y, in the position corresponding to position 30,
F, in the position corresponding to position 31,
D, in the position corresponding to position 49,
D, in the position corresponding to position 50,
N, in the position corresponding to position 65,
F, in the position corresponding to position 90,
T, in the position corresponding to position 91,
H, in the position corresponding to position 92,
N, in the position corresponding to position 93, and
S, in the position corresponding to position 94
of the sequence of SEQ ID NO: 1; and the heavy chain variable domain of said antibody may comprise amino acid residues:
Y, in the position corresponding to position 50,
L, in the position corresponding to position 57,
Y, in the position corresponding to position 59,
Y, in the position corresponding to position 60,
D, in the position corresponding to position 62,
W, in the position corresponding to position 102,
Y, in the position corresponding to position 103,
G, in the position corresponding to position 104, and
G, in the position corresponding to position 105,
of the sequence of SEQ ID NO:2.

The light chain of an antibody according to the current invention may further comprise an N in the position corresponding to position 65 of the sequence of SEQ ID NO:1; and the heavy chain variable domain may further comprise an W, in the position corresponding to position 47 of SEQ ID NO:2.

For MOR8457, the epitope was found to be composed of amino acids Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86 with respect to the sequence of PDGF-B as set forth in SEQ ID NO:33.

Thus, in one embodiment, the epitope bound by the antibody of the invention encompasses at least one amino acid residue, more preferably, at least two amino acid residues, even more preferably, at least three amino acid residues, yet more preferably, at least four amino acid residues, more preferably, at least five amino acid residues, yet more preferably, at least six amino acid residues, even more preferably, at least seven amino acid residues, yet more preferably, at least eight amino acid residues, more preferably, at least nine amino acid residues, even more preferably, at least ten amino acid residues, more preferably, at least eleven amino acid residues, even more preferably, at least twelve amino acid residues, yet more preferably, at least thirteen amino acid residues, more preferably, at least fourteen amino acid residues, yet more preferably, at least fifteen amino acid residues, even more preferably, at least sixteen amino acid residues, and even more preferably, all seventeen amino acid residues selected from the amino acid residues consisting of Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86 with respect to the sequence of PDGF-B as set forth in SEQ ID NO:33. In another embodiment, the antibody comprises a paratope encompassing the light chain variable domain residues G28, S29, Y30, F31, D49, D50, F90, T91, H92, N93, S94 based on Kabat numbering with respect to the sequence of SEQ ID NO:1, and the heavy chain variable domain residues Y50, L57, Y59, Y60, D62, W102, Y103, G104, G105 based on Kabat numbering with respect to the sequence of SEQ ID NO:2, wherein the antibody binds an epitope on PDGF-B comprising the following amino acid residues of PDGF-B (epitope) Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86 numbered with respect to the sequence of PDGF-B as set forth in SEQ ID NO:33.

In another embodiment, the antibody of the invention comprises a paratope wherein the amino acid residues of the paratope contact (less than or equal to 4 Å) the corresponding amino acid residues of PDGF-B (epitope) as shown on Table 4 of Example 7. That is, for the heavy chain variable domain of the antibody, Trp 47 contacts Lys 82 of PDGF-B, Leu 57 contacts Ile 77 of PDGF-B, Tyr 59 contacts Ile 77, Arg 79, Lys 80, Lys 81, and Pro 82 of PDGF-B; Trp 102 contacts Leu 8, Val 39, Trp 40, Asn 54, Arg 56, Ile 75, and Phe 84 of PDGF-B, Tyr 103 contacts Trp 40, Arg 73, Ile 75, and Phe 84 of PDGF-B, Gly 104 contacts Arg 73 and Phe 84 of PDGF-B, and Gly 105 contacts Phe 84 of PDGF-B, and for the heavy chain variable domain of the antibody, Gly 28 contacts Lys 86 of PDGF-B, Ser 29 contacts Lys 85 and Lys 86 of PDGF-B, Tyr 30 contacts Ile 83, Phe 84, Lys 85 and Lys 86 of PDGF-B, Phe 31 contacts Gln 71, Arg 73, Phe 84 and Lys 86 of PDGF-B, Asp 49 contacts Arg 73 of PDGF-B, Asp 50 contacts Lys 86 of PDGF-B, Asn 65 contacts Lys 86 of PDGF-B, Phe 90 contacts Pro 82, Ile 83, and Phe 84 of PDGF-B, Thr 91 contacts Lys 81 and Ile 83 of PDGF-B, His 92 contacts Lys 81 and Ile 83 of PDGF-B, Asn 93 contacts Lys 81 of PDGF-B, and Ser 94 contacts Lys 81 of PDGF-B, wherein residue numbering of PDGF-B contact residues is set forth with respect to the sequence of SEQ ID NO:33.

The antibody of the invention can bind either of two epitopes formed by the homodimerization of two PDGF-B polypeptide chains. Thus, the invention encompasses an antibody that binds one epitope of PDGF-BB where the epitope is selected from epitope 1 comprising amino acids Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86 with respect to the sequence of PDGF-B as set forth in SEQ ID NO:33 and epitope 2 comprising amino acids Trp 40, Asn 54, Glu 71, Arg 73, Ile 75, Glue 76, Ile 77, Arg 79, Lys 80, Lys 81, Pro 82, Ile 83, Phe 84, Lys 85 and Lys 86 with respect to the sequence of PDGF-B as set forth in SEQ ID NO:33.

The antibody of the invention encompasses antibodies that cannot bind both epitopes simultaneously. Thus, in one embodiment the antibody encompasses an antibody that can bind both epitope 1 and epitope 2, but not at the same time since these epitopes are located approximately 190 Å apart from each other on the PDGF-BB homodimer molecule.

An antibody according to the current invention may bind to the same epitope or domain of PDGF-B as the antibodies of the invention that are specifically disclosed herein. For example, other yet unidentified antibodies of the invention may be identified by comparing their binding to PDGF-B with that of the monoclonal antibody MOR8457, and germlined variants thereof; or by comparing the function of yet unidentified antibodies with that of MOR8457. Analyses and assays that may be used for the purpose of such identification include assays assessing the completion for binding of PDGF-B between the antibody of interest and PDGFRβ and between various anti-PDGF-B antibodies such as the assays described in Example 6, analysis of the crystal structure of the antibody with PDGF-B such as the analysis described in Example 7, assays described in Example 8 for inhibition of human mensangial cell proliferation, and the in vivo model described in Example 9 to assess the effect of the antibody in a rat model of nephritis.

In one embodiment, an antibody of the invention may bind to the same epitope or region as the MOR8457 antibodies described herein. The binding of these antibodies to PDGF-B is described in more detail elsewhere herein. An antibody of the invention may be an antibody that binds to the same epitope in PDGF-B as the MOR5457 antibodies. This may include it being in contact with the particular amino acids of PDGF-B as described above. For example, an antibody of the invention may bind to PDGF-B in such a way that it is in contact with amino acids Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86 with respect to the sequence of PDGF-B as set forth in SEQ ID NO:33, or with amino acids Trp 40, Asn 54, Glu 71, Arg 73, Ile 75, Glu 76, Ile 77, Arg 79, Lys 80, Lys 81, Pro 82, Ile 83, Phe 84, Lys 85 and Lys 86 with respect to the sequence of PDGF-B as set forth in SEQ ID NO:33.

An antibody of the invention may be capable of binding an epitope comprising one or more residues selected from the group consisting of Leu 38, Val, 39 and Trp 40, Asn 54, Arg 56, Glu 71, Arg 73, Ile 75, Glue 76, Ile 77, Arg 79, Lys 80, Lys 81, Pro 82, Ile 83, Phe 84, Lys 85 and Lys 86 with respect to the sequence of SEQ ID NO:33.

An antibody of the invention may be capable of binding an epitope comprising residues Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86, or an epitope comprising residues Trp 40, Asn 54, Glu 71, Arg 73, Ile 75, Glu 76, Ile 77, Arg 79, Lys 80, Lys 81, Pro 82, Ile 83, Phe 84, Lys 85 and Lys 86, all with respect to the sequence of PDGF-B as set forth in SEQ ID NO:33.

An antibody of the invention may have the ability to compete with another antibody of the invention for binding to PDGF-B as described herein. For example, an antibody of the invention may cross-compete with MOR8457 antibodies described herein for binding to PDGF-B, or to a suitable fragment or variant of PDGF-B that is bound by the MOR8457 antibodies. Such cross-competing antibodies can be identified based on their ability to cross-compete with a known antibody of the invention in standard binding assays. For example, SPR e.g. by using a Biacore™ system, ELISA assays or flow cytometry may be used to demonstrate cross-competition. Such cross-competition may suggest that the two antibodies bind to identical, overlapping or similar epitopes.

The antibody of the invention encompasses antibodies capable of binding PDGF-B with a higher affinity than AbyD3263 described in Ogawa et al., 2010, Hepatol. Res. 40:1128-1141.

An antibody of the invention may therefore be identified by a method that comprises a binding assay which assesses whether or not a test antibody is able to compete with a known antibody of the invention for a binding site on the target molecule. Methods for carrying out competitive binding assays are disclosed herein and/or are well known in the art. For example they may involve binding a known antibody of the invention to a target molecule using conditions under which the antibody can bind to the target molecule. The antibody/target complex may then be exposed to a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test antibody can compete with an antibody of the invention for binding to the target and thus that the test antibody binds to the same epitope or region on the PDGF-B protein as the known antibody of the invention. A test antibody that is identified as competing with a known antibody of the invention in such a method is also a potential antibody according to the present invention. The fact that the test antibody can bind PDGF-B in the same region as a known antibody of the invention and can compete with the known antibody of the invention suggests that the test antibody may act as a ligand at the same binding site as the known antibody and that the test antibody may therefore mimic the action of the known antibody. This can be confirmed by assessing the activity of PDGF-B in the presence of the test compound as described herein.

The known antibody of the invention may be an antibody as described herein, such as MOR8457, or any variant or fragment thereof as described herein that retains the ability to bind to -PDGF-B, such as germlined antibodies, one of which is herein disclosed comprising a germlined VH (MOR8457-GL-VH; SEQ ID NO:6) and a germlined VL (MOR8457-LG-VL; SEQ ID NO:4), or variants such as MOR8457-15, comprising a modified VH (MOR8457-15-VH; SEQ ID NO:44) and modified VL (MOR8457-15-VL; SEQ ID NO:34), and MOR8457-16, comprising the same modified VH as MOR8457-15 (also identified as MOR8457-16-VH or MORE8457-15/16-VH); SEQ ID NO:44) and a modified VL (MOR8457-16-VL; SEQ ID NO:39). An antibody of the invention may bind to the same epitope as MOR8457 antibody as described herein or any variant or fragment thereof as described herein that retains the ability to bind to PDGF-B.

An antibody of the invention may bind an epitope that is identical to, overlaps, or is similar to the MOR8457 epitope that is further described in the examples. For example, an antibody of the invention may bind to five or more, six or more, seven or more, eight or more or ten or twelve, or fourteen, or sixteen or more of the amino acid residues set out above for binding of MOR8457. For example, when contacted with a polypeptide of SEQ ID NO:33, an antibody of the invention may bind to the polypeptide and make contact with amino acids Leu 38, Val, 39 and Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86, or with amino acids Trp 40, Asn 54, Glu 71, Arg 73, Ile 75, Glu 76, Ile 77, Arg 79, Lys 80, Lys 81, Pro 82, Ile 83, Phe 84, Lys 85 and Lys 86, or a subset of those amino acids, such as at least 2, at least 3, at least 4, at least 5, at least 6, at least 7, at least 8, at least 9, at least 10, at least 11, at least 12, at least 13, at least 14, at least 15, at least 16, or at least 17 of those amino acids.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. Preferably, the other molecule is not identical to the target molecule. Preferably the target molecule is not a fragment of the target molecule.

The $K_D$ of an antibody of the current invention may be less than 69 pM, such as less than 50 pM, such as less than 30 pM, such as less than 25 pM, such as less than 15 pM, such as less than 13 pM, such as less than 12 pM, such as less than 10 pM, such as less than 4 pM, such as less than 2 pM, such as less than 2 pM, such as between 15 pM and 2 pM.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, i.e., PDGF-B. For example, where the target is PDGF-B, the other molecule used for comparison may be a protein that forms part of the PDGF-B/PDGFRβ signaling cascade. By ensuring that the antibody of the invention has specificity for PDGF-BB over another such molecule, unwanted in vivo cross-reactivity may be avoided.

The antibody of the invention may retain the ability to bind to some molecules that are related to the target molecule. For example, a full-length mature human PDGF-B may be used as the target, but the antibody may also be able to bind to, e.g. propeptide forms of human PDGF-B, fragments or truncated forms of human PDGF-B, PDGF-B that is bound to lipoprotein or to a cell or PDGF-B from other species, such as other mammalian PDGF-B.

Alternatively, the antibody of the invention may have specificity for a particular target molecule. For example, it may bind to one target molecule as described herein, but may not bind, or may bind with significantly reduced affinity to a different target molecule as described herein. For example, a full length mature human PDGF-B may be used as the target, but the antibody that binds to that target may be unable to bind to or may bind with lesser affinity to, e.g. other PDGFs (PDGF-A or PDGF-C, or PDGF-D) or PDGF-B from other species, such as other mammalian PDGF-B.

An antibody of the invention may bind to PDGF-B and in doing so may inhibit an activity of PDGF-B.

The term "binding affinity," is used herein as a measure of the strength of a non-covalent interaction between two molecules, e.g., an antibody, or an antigen-binding fragment thereof, and an antigen. The term "binding affinity" is used to describe monovalent (intrinsic activity).

Following the above definition binding affinities associated with different molecular interactions, e.g., comparison of the binding affinity of different antibodies for a given antigen, may be compared by comparison of the $K_D$ values for the individual antibody/antigen complexes.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind PDGF-B.

Typically, the $K_D$ for the antibody with respect to PDGF-B will be 2-fold, preferably 5-fold, more preferably 10-fold less than $K_D$ with respect to the other, non-PDGF-B molecule such as unrelated material or accompanying material in the environment. More preferably, the $K_D$ will be 50-fold less, such as 100-fold less, or 200-fold less; even more preferably 500-fold less, such as 1,000-fold less, or 10,000-fold less.

The value of the dissociation constant can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system.

A competitive binding assay can be conducted in which the binding of the antibody to the antigen is compared to the binding of the target by another ligand of that target, such as another antibody or a soluble receptor that otherwise binds the target (e.g., PDGFRβ—IgG1). The concentration at which 50% inhibition occurs is known as the $K_i$. Under ideal conditions, the $K_i$ is equivalent to $K_D$. The $K_{Ki}$ value will never be less than the $K_D$, so measurement of $K_i$ can conveniently be substituted to provide an upper limit for $K_D$.

An antibody of the invention may have a $K_D$ for PDGF-B of $1\times10^{-7}$M or less, $1\times10^{-8}$M or less, or $1\times10^{-9}$M or less, or $1\times10^{-19}$M or less, $1\times10^{-11}$M or less, or $1\times10^{-12}$M or less, or $1\times10^{-13}$M or less, $1\times10^{-14}$M or less, or $1\times10^{-15}$M or less.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold 200-fold, 500-fold, 1,000-fold or 10.000-fold or greater than its affinity for binding to another non-PDGF-B molecule.

In other embodiments, the binding affinity ($K_D$) of PDGF-B antibody to PDGF-B can be about 0.001 to about 250 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM. In some embodiments, the $K_D$ of a PDGF-B antibody ranges from about 70 pM to about 1 pM. In some embodiments, the $K_D$ of a PDGF-B antibody for human PDGF-B ranges from about 30 pM to about 2 pM. In some embodiments, the binding affinity of a PDGD-B antibody of the invention is about 69 pM, about 28 pM, about 25 pM, about 15 pM, about 13 pM, about 10 pM, about 4 pM, and about 2 pM.

In one embodiment, the antibody of the invention is not antibody AbyD3263 as described in Ogawa et al., 2010, Hepatology Res. 40:1128-1141.

In one embodiment, the antibody of the invention binds human PDGF-BB with a binding affinity ($K_D$) lower than the $K_D$ of AbyD3263, i.e., 13 nM.

The invention provides any of the following, or compositions (including pharmaceutical compositions) comprising, an antibody having a light chain sequence, or a portion thereof, and a heavy chain, or a portion thereof, derived from MOR8457.

Polypeptide or antibody "fragments" or "portions" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the MOR8457 antibody or a variant thereof. The antibody of the invention may be or may comprise an antigen binding portion of this antibody or a variant thereof. For example, the antibody of the invention may be a Fab fragment of this antibody or a variant thereof or may be a single chain antibody derived from this antibody or a variant thereof.

The amino acid sequences of the light (MOR8457-VL) and heavy (MOR8457-VH) chain variable domains of the MOR8457 antibody are provided in SEQ ID NOs: 1 and 2, respectively. The amino acid sequences for the VL and VH variable domains of the germlined MOR8457 antibody are given in SEQ ID NOs: 4 (MOR8457-GL-VL) and 6 (MOR8457-GL-VH), respectively. The amino acid sequence of the full-length germlined light chain (MOR8457-GL-LC) is provided in SEQ ID NO:16, and the amino acid sequence of the full-length germlined heavy chain further comprising an effector function triple mutation in the constant domain (MOR8457-GL-hIgG1-3m-HC) is provided in SEQ ID NO:14. In addition, amino acid sequences of variant antibodies MOR8457-15 and MOR8457-16 are provided. The amino acid sequences of the VL and VH of MOR8457-15 are given in SEQ ID NOs:34 (MOR8457-15-VL) and 44 (MOR8457-15-VH), respectively. The amino acid sequence of the full-length MOR8457-15 light chain (MOR8457-15-LC) is provided in SEQ ID NO:37, and the amino acid sequence of the full-length MOR8457-15 heavy chain further comprising an effector function triple mutation in the constant domain (MOR8457-15-HC) is provided in SEQ ID NO:46. The amino acid sequences of the VL and VH of MOR8457-16 are given in SEQ ID NOs:39 (MOR8457-16-VL) and 44 (MOR8457-16-VH), respectively. The amino acid sequence of the full-length MOR8457-16 light chain (MOR8457-16-LC) is provided in SEQ ID NO:42, and the amino acid sequence of the full-length MOR8457-16 heavy chain further comprising an effector function triple mutation in the constant domain (MOR8457-16-HC) is provided in SEQ ID NO:46. Thus, it is understood that MOR8457-15 and MOR8457-16 share the same VH amino acid sequence which is set forth in SEQ ID NO:44.

An antibody of the invention may comprise the VL amino acid sequence of SEQ ID No: 1 or SEQ ID NO:4, or a fragment or variant thereof. An antibody of the invention may comprise the VH amino acid sequence of SEQ ID No: 2 or SEQ ID NO:6, or a fragment or variant thereof. An antibody of the invention may comprise both (a) the VL amino acid sequence of SEQ ID No: 1, or a fragment or variant thereof and the VH amino acid sequence of SEQ ID No: 2 or a fragment or variant thereof, or (b) the VL amino acid sequence of SEQ ID No: 1, or a fragment or variant thereof, and amino acid sequence the VH of SEQ ID No: 6 or a fragment or variant thereof, or (c) the VL amino acid sequence of SEQ ID No: 4, or a fragment or variant thereof, and amino acid sequence the VH of SEQ ID No: 2 or a fragment or variant thereof, or (d) the VL amino acid sequence of SEQ ID No: 4, or a fragment or variant thereof, and amino acid sequence the VH of SEQ ID No: 6 or a fragment or variant thereof.

An antibody of the invention may also comprise the VL amino acid sequence of SEQ ID NO; 34 or SEQ ID NO:39, or a fragment or variant thereof. An antibody of the invention may comprise the VH amino acid sequence of SEQ ID NO: 44, or a fragment or variant thereof. An antibody of the invention may comprise both (a) the VL amino acid sequence of SEQ ID No: 34, or a fragment or variant thereof and the VH amino acid sequence of SEQ ID No: 44 or a fragment or variant thereof, or (b) the VL amino acid sequence of SEQ ID No: 39, or a fragment or variant thereof, and amino acid sequence the VH of SEQ ID No: 44 or a fragment or variant thereof.

In one aspect, the antibody comprises a VL comprising the sequence of SEQ ID NO:1, SEQ ID NO:4, SEQ ID NO:34, or SEQ ID NO:39. In another aspect, the antibody comprises a VH comprising the amino acid sequence of SEQ ID NO:2, SEQ ID NO:6, or SEQ ID NO:44. In another aspect, the antibody comprises a variant of sequence of SEQ ID NO:1, SEQ ID NO:2, SEQ ID NO:4, SEQ ID NO:6, SEQ ID NO:34, SEQ ID NO:39, and SEQ ID NO:44, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a $V_H$ chain amino acid sequence as set forth in SEQ ID NO:2, SEQ ID NO:6 or SEQ ID NO:44, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:2, SEQ ID NO:6, or SEQ ID NO:44. In a further aspect, said variant shares at least 65%, at least 75%, at least 85%, at least 90%, at least 95%, at least 96%, at least 97%, at least 98%, or at least 99% sequence identity with SEQ ID NO:2, SEQ ID NO:6, or SEQ ID NO:44, and wherein said antibody or antigen-binding portion specifically binds PDGF-B.

In a further aspect, the disclosure provides an isolated antibody or antigen-binding portion thereof that comprises a $V_L$ chain amino acid sequence as set forth in SEQ ID NO:1, SEQ ID NO:4, SEQ ID NO:34, or SEQ ID NO:39 or a variant thereof. In one aspect, said antibody variant comprises 1, 2, 3, 4, 5, 6, 7, 8, 9, 10, 11, 12, 13, 14, or conservative or non-conservative substitutions, and/or 1, 2, 3, 4, 5, 6, 7, 8, 9, 10, 11, 12, 13, 14, or 15 additions and/or deletions to SEQ ID NO:1, SEQ ID NO:4, SEQ ID NO:34, or SEQ ID NO:39. In a further aspect, said variant shares at least 65%, at least 75%, at least 85%, at least 90%, at least 95%, at least 96%, at least 97%, at least 98%, or at least 99% sequence identity with SEQ ID NO:1, SEQ ID NO:4, SEQ ID NO:34, or SEQ ID NO:39, and wherein said antibody or antigen-binding portion specifically binds PDGF-B.

An antibody of the invention may comprise a heavy chain comprising a VH comprising the amino acid sequence of SEQ ID NO:2, SEQ ID NO:6 or SEQ ID NO:44, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO:2, SEQ ID NO:6 or SEQ ID NO:44 and further comprising a human wild type IgG1 constant domain comprising the amino acid sequence of SEQ ID NO:19. In another aspect, the IgG1 constant domain comprises a triple mutation decreasing or abolishing Fc effector function (hIgG1-3m; SEQ ID NO:21). In one aspect, the antibody of the invention may comprise a heavy chain comprising a germlined VH comprising the sequence of SEQ ID NO:6 and further comprising a human IgG1-3m constant domain such that the full-length heavy chain amino acid sequence comprises SEQ ID NO:14 (MOR8457-GL-hIgG1-3m-HC). In another aspect, the antibody of the invention may comprise a heavy chain comprising the sequence of SEQ ID NO:44 and further comprising a human IgG1-3m constant domain such that the full-length heavy chain amino acid sequence comprises SEQ ID NO:46 (MOR8457-15-HC or MOR8457-16-HC).

In a further aspect, the disclosure provides an isolated antibody or antigen-binding portion thereof that comprises a full-length heavy chain comprising the amino acid sequence as set forth in SEQ ID NO:14, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:14. In a further aspect, said variant shares at least 65%, at least 75%, at least 85%, at least 90%, at least 95%, at least 96%, at least 97%, at least 98%, or at least 99% sequence identity with SEQ ID NO:14, and wherein said antibody or antigen-binding portion specifically binds PDGF-B.

An antibody of the invention may comprise a light chain comprising a VL comprising the amino acid sequence of SEQ ID NO:1, SEQ ID NO:4, SEQ ID NO:34, or SEQ ID NO:39, wherein the antibody further comprises a light chain constant domain. As more fully set forth elsewhere herein, the antibody light chain constant domain can be selected from a Cκ or Cλ constant region, preferably, a Cλ constant region.

In one aspect, the antibody may comprise a light chain comprising a VL selected from a VL comprising the amino acid sequence of SEQ ID NO:1, SEQ ID NO:4, SEQ ID NO:34, or SEQ ID NO:39 and further comprising a human wild type Cλ constant domain comprising the amino acid sequence of SEQ ID NO:23. In another aspect, the antibody may comprise an original VL sequence (SEQ ID NO:1) and further comprise a human Cλ constant domain comprising an inadvertent triple mutation substituting the sequence TVL with IKR (SEQ ID NO:17; MOR8457-IKR-LC). In one aspect, the antibody of the invention may comprise a light chain comprising a germlined VL comprising the sequence of SEQ ID NO:4 and further comprising a human wild type Cλ constant domain (SEQ ID NO:23) such that the full-length light chain amino acid sequence comprises SEQ ID NO:16 (MOR8457-GL-LC). In another aspect, the antibody of the invention may comprise a light chain comprising a variant VL comprising the sequence of SEQ ID NO:34 or SEQ ID NO:39, such that the full length light chain amino acid sequence comprises SEQ ID NO:37 (MOR8457-15-LC) or SEQ ID NO:42 (MOR8457-16-LC).

In a further aspect, the disclosure provides an isolated antibody or antigen-binding portion thereof that comprises a full-length light chain comprising the amino acid sequence as set forth in SEQ ID NO:16, SEQ ID NO:17, SEQ ID NO:37, or SEQ ID NO:42, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:16, SEQ ID NO:17, SEQ ID NO:37, or SEQ ID NO:42. In a further aspect, said variant shares at least 65%, at least 75%, at least 85%, at least 90%, at least 95%, at least 96%, at least 97%, at least 98%, or at least 99% sequence identity with SEQ ID NO:16, SEQ ID NO:17, SEQ ID NO:37, or SEQ ID NO:42, and wherein said antibody or antigen-binding portion specifically binds PDGF-B.

The invention encompasses an antibody, or antigen-binding fragment thereof, comprising the three CDRs of the heavy chain variable domain amino acid sequence encoded by the polynucleotide insert of the vector deposited with the ATCC on Nov. 6, 2012, as MOR8457-GL-VH (ATCC Acc. No. PTA-13303). In one aspect, the antibody, or antigen-binding fragment thereof, of the invention comprises the $V_H$ domain amino acid sequence encoded by the polynucleotide insert of the vector deposited with the ATCC as MOR8457-GL-VH (ATCC Acc. No. PTA-13303).

The invention encompasses an antibody, or antigen-binding fragment thereof, comprising two CDRs, CDR-H2 and CDR-H3, of the heavy chain variable domain amino acid sequence encoded by the polynucleotide insert of the vector deposited with the ATCC on Nov. 6, 2012, as MOR8457-GL-VH (ATCC Acc. No. PTA-13303). In one aspect, the antibody, or antigen-binding fragment thereof, of the invention comprises the $V_H$ domain amino acid sequence encoded by the polynucleotide insert of the vector deposited with the ATCC as MOR8457-GL-VH (ATCC Acc. No. PTA-13303), wherein CDR-H1 need not be present.

The invention encompasses an antibody, or antigen-binding fragment thereof, comprising the three CDRs of the light chain variable domain amino acid sequence encoded by the polynucleotide insert of the vector deposited with the ATCC on Nov. 6, 2012, as MOR8457-GL-VL (ATCC Acc. No. PTA-13302). In one aspect, the antibody, or antigen-binding fragment thereof, of the invention comprises the VL domain amino acid sequence encoded by the polynucleotide insert of the vector deposited with the ATCC as MOR8457-GL-VL (ATCC Acc. No. PTA-13302).

The invention encompasses an antibody, or antigen-binding fragment thereof, comprising the three CDRs of the light chain variable domain amino acid sequence encoded by the polynucleotide insert of the vector deposited with the ATCC on Nov. 6, 2012, as MOR8457-GL-VL (ATCC Acc. No. PTA-13302), and the three CDRs of the heavy chain variable domain amino acid sequence encoded by the polynucleotide insert of the vector deposited with the ATCC as MOR8457-GL-VH (ATCC Acc. No. PTA-13303).

The invention encompasses an antibody, or antigen-binding fragment thereof, comprising the three CDRs of the light chain variable domain amino acid sequence encoded by the polynucleotide insert of the vector deposited with the ATCC on Nov. 6, 2012, as MOR8457-GL-VL (ATCC Acc. No. PTA-13302), and two CDRs, CDR-H2 and CDR-H3, of the heavy chain variable domain amino acid sequence encoded by the polynucleotide insert of the vector deposited with the ATCC as MOR8457-GL-VH (ATCC Acc. No. PTA-13303).

The invention encompasses an antibody, or antigen-binding fragment thereof, comprising the light chain variable domain amino acid sequence encoded by the polynucleotide insert of the vector deposited with the ATCC on Nov. 6, 2012, as MOR8457-GL-VL (ATCC Acc. No. PTA-13302), and the heavy chain variable domain amino acid sequence encoded by the polynucleotide insert of the vector deposited with the ATCC as MOR8457-GL-VH (ATCC Acc. No. PTA-13303).

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

An antibody of the invention may comprise a fragment of one of the VL or VH amino acid sequences shown in FIG. 1. For example, an antibody of the invention may comprise a fragment of at least 7, at least 8, at least 9, at least 10, at least 12, at least 15, at least 18, at least 20 or at least 25 consecutive amino acids from SEQ ID NOS: 4, 6, 34, 40, or 44. Such a fragment will preferably retain one or more of the functions discussed above, such as the ability to bind to PDGF-B.

A suitable fragment or variant of any of these VH or VL sequences will retain the ability to bind to PDGF-B. It will preferably retain the ability to specifically bind to PDGF-B. It will preferably retain the ability to specifically bind to the same or similar epitope or region of the PDGF-B molecule as the antibody (MOR8457) from which it is derived. It will preferably retain one or more additional functions of the antibody from which it is derived, such as the ability to inhibit PDGF-B binding to its receptor, the activity or the ability to inhibit PDGFR signaling, the ability to inhibit PDGF-B induction of cell proliferation, among others.

A suitable fragment or variant VL sequence will preferably retain the amino acids at positions G28, S29, Y30, F31, D49, D50, F90, T91, H92, N93, S94 based on the amino acid sequence of SEQ ID NO:1 or SEQ ID NO:4. A suitable fragment or variant VH sequence will preferably retain the amino acids at positions Y50, L57, Y59, Y60, D62, W102, Y103, G104, G105 with respect to the sequence of SEQ ID NO:2 or SEQ ID NO:6. As identified in Tables 2 and 3, these are the residues in the MOR8457 light and heavy chain variable domain sequences that have a heavy atom within a distance of 4 Å from a heavy atom of PDGF-B when MOR8457 is bound to PDGF-BB.

An antibody of the invention may comprise a CDR region from the specific antibody identified herein such as a CDR region from within SEQ ID NO: 1, 2, 4, 6, 34, 39, or 44. Such an antibody will preferably retain the ability to bind to PDGF-B as described herein.

For example, as shown in FIG. 1, using the Kabat definition, the CDR sequences within the light chain of MOR8457 may be identified as amino acids SGDSLGSYFVH (MOR8457CDR-L1; SEQ ID NO:10), DDSNRPS (MOR8457CDR-L2; SEQ ID NO:11, or SAFTHNSDV (MOR8457CDR-L3; SEQ ID NO:12). In addition, the CDR sequences within the light chain of variant antibody MOR8457-15 may be identified as amino acids SGDSLGSYFVH (MOR8457CDR-L1; SEQ ID NO:10), DDSNRPS (MOR8457CDR-L2; SEQ ID NO:11, or SAFTHNSNV (MOR8457-15 CDR-L3; SEQ ID NO:36). Furthermore, the CDR sequences within the light chain of variant antibody MOR8457-16 may be identified as amino acids SGDSLGSYFVH (MOR8457 CDR-L1; SEQ ID NO:10), DDSKRPS (MOR8457-16 CDR-L2; SEQ ID NO:41, or SAFTHNSDV (MOR8457CDR-L3; SEQ ID NO:12). The CDR sequences within the heavy chain of MOR8457 may be identified as amino acids GFTFSSYAMS (MOR8457 CDR-H1; SEQ ID NO:7), YISDDGSLKYYADSVKG (MOR8457CDR-H2; SEQ ID NO:8) or HPYWYGGQLDL (MOR8457CDR-H3; SEQ ID NO:9). An antibody of the invention may comprise one or more of the CDR sequences shown in FIGS. 1C-F and 1I-K. For example, an antibody of the invention may comprise one, two or three of the amino acid sequences set forth in SEQ ID NO:7, 8 and 9. An antibody of the invention may alternatively or additionally comprise one, two or three of the amino acid sequences set forth in SEQ ID NO:10, 11, 12, 36, and 41. An antibody of the invention may comprise all six amino acid sequences set forth in SEQ ID NOs:7-12, or SEQ ID NOs; 7, 8, 9, 10, 12, 41, or SEQ ID NOs: 7, 8, 9, 10, 11, 36.

In one aspect, the disclosure provides an isolated antibody or antigen-binding portion thereof that comprises six CDRs comprising the sequences of SEQ ID NOs:7-12, SEQ ID NOs; 7, 8, 9, 10, 12, 41, or SEQ ID NOs: 7, 8, 9, 10, 11, 36, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs comprising the sequences of SEQ ID NOs:7-12, SEQ ID NOs; 7, 8, 9, 10, 12, 41, or SEQ ID NOs: 7, 8, 9, 10, 11, 36. In a further aspect, said variant shares at least 65%, at least 75%, at least 85%, at least 90%, at least 95%, at least 96%, at least 97%, at least 98%, or at least 99% sequence identity with the sequences of SEQ ID NOs:7-12, SEQ ID NOs; 7, 8, 9, 10, 12, 41, or SEQ ID NOs: 7, 8, 9, 10, 11, 36 and wherein said antibody or antigen-binding portion specifically binds PDGF-B.

An antibody of the invention may alternatively or additionally comprise five of the CDR sequences of MOR8457 or its variants. That is, the crystal structure data disclosed elsewhere herein (Example 7) demonstrate that CDR-H1 does not make contact with PDGF-B (i.e., none of the heavy atoms of the sequence of SEQ ID NO:7 is within 4 Å of the heavy atom of a residue of PDGF-B) suggesting MOR8457CDR-H1 may not contribute to binding to PDGF-B. Therefore, an antibody of the invention may comprise, for example, the following combinations of five CDR domains: CDR-H2 (SEQ ID NO:8), CDR-H3 (SEQ ID NO:9), CDR-L1 (SEQ ID NO:10), CDR-L2 (SEQ ID NO:11) and CDR-L3 (SEQ ID NO:12); or CDR-H2 (SEQ ID NO:8), CDR-H3 (SEQ ID NO:9), CDR-L1 (SEQ ID NO:10), CDR-L2 (SEQ ID NO:11) and CDR-L3 (SEQ ID NO:36); or CDR-H2 (SEQ ID NO:8), CDR-H3 (SEQ ID NO:9), CDR-L1 (SEQ ID NO:10), CDR-L2 (SEQ ID NO:41) and CDR-L3 (SEQ ID NO:12).

In one aspect, the disclosure provides an isolated antibody or antigen-binding portion thereof that comprises five CDRs comprising the sequences of SEQ ID NOs:8-12, SEQ ID NOS: 8, 9, 10, 11 and 36, SEQ ID NOS: 8, 9, 10, 41, and 12, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs comprising the sequences of SEQ ID NOs:8-12, 36, and 41. In a further aspect, said variant shares at least 65%, at least 75%, at least 85%, at least 90%, at least 95%, at least 96%, at least 97%, at least 98%, or at least 99% sequence identity with the sequences of SEQ ID NOs:8-12, and wherein said antibody or antigen-binding portion specifically binds PDGF-B.

An antibody of the invention may comprise a CDR sequence where the amino acid residues that are not contact residues may be substituted. That is, where the antibody comprises any of the following CDRs, the amino acid residues that are not underlined, may be substituted or deleted as they do not contact the epitopes (1 or 2) on PDGF-B:

(SEQ ID NO: 7)
MOR8457 CDR-H1 GFTFSSYAMS (SEQ ID NO: 8)
MOR8457 CDR-H2 YISDDGSLKYYADSVKG (SEQ ID NO: 9)
MOR8457 CDR-H3 HPYWYGGQLDL (SEQ ID NO: 10)
MOR8457 CDR-L1 SGDSLGSYFVH (SEQ ID NO: 11)
MOR8457 CDR-L2 DDSNRPS (SEQ ID NO: 12)
MOR8457 CDR-L3 SAFTHNSDV

The heavy chain of an antibody according to the invention may comprise a CDR-H1 amino acid sequence of GFTFSSYAMS (SEQ ID NO:7) wherein at least one of these amino acids may be substituted by a different amino acid. Preferably, all of these amino acids may be substituted.

The heavy chain of an antibody according to the invention may comprise a CDR-H2 amino acid sequence of YISDDGS LKYYADSVKG (SEQ ID NO:8) wherein at least one residue not underlined (where the underlined residues are Y50, L57, Y59, Y60, D62) may be substituted by a different amino acid.

The heavy chain of an antibody according to the invention may comprise a CDR-H3 amino acid sequence HPY WYGGQLDL (SEQ ID NO:9) wherein at least one residue not underlined (where the underlined residues are W102, Y103, G104, G105) may be substituted by a different amino acid.

The light chain of an antibody according to the invention may comprise a CDR-L1 amino acid sequence of SGDSLGS YFVH (SEQ ID NO:10) wherein at least one residue not underlined (where the underlined residues are G28, S29, Y30, F31) may be substituted by a different amino acid.

The light chain of an antibody according to the invention may comprise a CDR-L2 amino acid sequence of DDSNRPS (SEQ ID NO:11) wherein at least one of residue not underlined (wherein the underlined residues are D49, D50) may be substituted by a different amino acid.

The light chain of an antibody according to the invention may comprise a CDR-L3 amino acid sequence of SA FTHNSDV (SEQ ID NO:12) wherein at least one residue not underlined (wherein the underlined residues are F90, T91, H92, N93, S94) may be substituted by a different amino acid.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 3 under the heading of "conservative substitutions." If such substitutions result in a change in biological activity, then more substantial changes, denominated "exemplary substitutions" shown below, or as further described below in reference to amino acid classes, may be introduced and the products screened.

| Amino Acid Substitutions | | |
|---|---|---|
| Original Residue | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |

-continued

| Amino Acid Substitutions | | |
|---|---|---|
| Original Residue | Conservative Substitutions | Exemplary Substitutions |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:
(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The invention also provides methods of generating, selecting, and making PDGF-B antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992, Bio/Technol. 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the PDGF-B monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for PDGF-B, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a PDGF-B polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the PDGF-B antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for PDGF-B.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a PDGF-B antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody MOR8457, or germlined versions thereof. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the PDGF-B antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in FIG. 1 and the CDRs indicated in FIG. 1. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to PDGF-B. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for PDGF-B, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of a PDGF-B antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in Eur. J. Immunol., 1999, 29:2613-2624; PCT Application No. PCT/GB99/01441; and/or UK Patent Application No. 9809951.8. In such embodiments, the Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment, the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19).

In some embodiments, the antibody comprises a human heavy chain $IgG_2$ constant region comprising the following mutations: A330P331 to S330S331 (amino acid numbering with reference to the wild type $IgG_2$ sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The disclosure also provides an antibody constant domain that may be further modified. It is known that variants of the Fc region, e.g., amino acid substitutions, insertions, and/or additions and/or deletions, enhance or diminish effector function. See, e.g., Presta et al, 2002, Biochem. Soc. Trans. 30:487-490; Strohl, 2009, Curr. Opin. Biotechnol. 20(6):685-691; U.S. Pat. Nos. 5,624,821, 5,648,260, 5,885,573, 6,737,056, 7,317,091; PCT publication Nos. WO 99/58572, WO 00/42072, WO 04/029207, WO 2006/105338, WO 2008/022152, WO 2008/150494, WO 2010/033736; U.S. Patent Application Publication Nos. 2004/0132101, 2006/0024298, 2006/0121032, 2006/0235208, 2007/0148170; Armour et al., 1999, Eur. J. Immunol. 29(8):2613-2624 (reduced ADCC and CDC); Shields et al., 2001, J. Biol. Chem. 276(9):6591-6604 (reduced ADCC and CDC); Idusogie et al., 2000, J. Immunol. 164(8):4178-4184 (increased ADCC and CDC); Steurer et al., 1995, J. Immunol. 155(3):1165-1174 (reduced ADCC and CDC); Idusogie et al., 2001, J. Immunol. 166(4):2571-2575 (increased ADCC and CDC); Lazar et al., 2006, Proc. Natl. Acad. Sci. USA 103(11): 4005-4010 (increased ADCC); Ryan et al., 2007, Mol. Cancer. Ther., 6: 3009-3018 (increased ADCC); Richards et al., 2008, Mol. Cancer. Ther. 7(8):2517-2527.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of a PDGF-B antibody of the invention can be cleaved or otherwise removed. In various embodiments of the invention, the heavy and light chains of the antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 18), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to PDGF-B and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of a PDGF-B antibody of the invention linked to another polypeptide. In another embodiment, only the variable domains of the PDGF-B antibody are linked to the polypeptide. In another embodiment, the VH domain of a PDGF-B antibody is linked to a first polypeptide, while the VL domain of a PDGF-B antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 1 or 4 and/or at least 10 amino acids of the variable heavy chain region shown in SEQ ID NOs: 2 or 6. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, and 4 and 6. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

In other embodiments, other modified antibodies may be prepared using nucleic acid molecules encoding a PDGF-B antibody. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of PDGF-B. In some embodiments, the modified antibodies described above are prepared using one or more of the variable domains or CDR regions from a PDGF-B antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin).

For simplicity, reference will be made generally to antibodies with the understanding that these methods apply to any of the PDGF-B binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following PDGF-B antibodies and antigen-binding fragments thereof: MOR8457 VL (SEQ ID NO:1), MOR8457 VH (SEQ ID NO:2), MOR8457-GL-VL (SEQ ID NO:4), MOR8457-GL-VH (SEQ ID NO:6), MOR8457-GI-hIgG1-3m-HC (SEQ ID NO:14), MOR8457-GL-LC (SEQ ID NO:16), MOR8457-GL-IKR-LC (SEQ ID NO:17), MOR8457-hIgG1-3m-HC (SEQ ID NO:18), MOR8457-15-VL (SEQ ID NO:34), MOR8457-15-LC (SEQ ID NO:37), MOR8457-16-VL (SEQ ID NO:39), MOR8457-16-LC (SEQ ID NO:42), MOR8457-15-VH/ MOR8457-16-VH (SEQ ID NO:44), MOR8457-15-HC/ MOR8457-16-HC (SEQ ID NO:46), MOR8457 CDR-H1 (SEQ ID NO:7), MOR8457CDR-H2 (SEQ ID NO:8), MOR8457CDR-H3 (SEQ ID NO:9), MOR8457CDR-L1 (SEQ ID NO:10), MOR8457CDR-L2 (SEQ ID NO:11), MOR8457CDR-L3 (SEQ ID NO:12), MOR8457-15-CDR-L3 (SEQ ID NO:36), MOR8457-16-CDR-L2 (SEQ ID NO:41) or any fragment or part thereof having the ability to bind PDGF-B.

The invention provides polynucleotides, or compositions comprising the polynucleotides, encoding any of the following PDGF-B antibodies and antigen-binding fragments thereof or the invention, including: MOR8457 VL (SEQ ID NO:1), MOR8457 VH (SEQ ID NO:2), MOR8457-GL-VL (SEQ ID NO:4), MOR8457-GL-VH (SEQ ID NO:6), MOR8457-GI-hIgG1-3m-HC (SEQ ID NO:14), MOR8457-GL-LC (SEQ ID NO:16), MOR8457-GL-IKR-LC (SEQ ID NO:17), MOR8457-hIgG1-3m-HC (SEQ ID NO:18), MOR8457-15-VL (SEQ ID NO:34), MOR8457-15-LC (SEQ ID NO:37), MOR8457-16-VL (SEQ ID NO:39), MOR8457-16-LC (SEQ ID NO:42), MOR8457-15-VH/ MOR8457-16-VH (SEQ ID NO:44), MOR8457-15-HC/ MOR8457-16-HC (SEQ ID NO:46), MOR8457CDR-H1 (SEQ ID NO:7), MOR8457CDR-H2 (SEQ ID NO:8), MOR8457CDR-H3 (SEQ ID NO:9), MOR8457CDR-L1 (SEQ ID NO:10), MOR8457 CDR-L2 (SEQ ID NO:11), MOR8457CDR-L3 (SEQ ID NO:12), MOR8457-15-CDR-L3 (SEQ ID NO:36), MOR8457-16-CDR-L2 (SEQ ID NO:41) or any fragment or part thereof having the ability to bind PDGF-B, wherein the sequence of the polynucleotide encompasses the sequence of SEQ ID NO:3 (encoding MOR8457-GL-VL), SEQ ID NO:5 (encoding MOR8457-GL-VH), SEQ ID NO:13 (encoding MOR8457-GL-hIgG1-3m-HC), SEQ ID NO:15 (encoding MOR8457-GL-LC), SEQ ID NO:35 (encoding MOR8457-15-VL), SEQ ID NO:38 (encoding MOR8457-15-LC), SEQ ID NO:40 (encoding MOR8457-16-VL), SEQ ID NO:43 (encoding MOR8457-16-LC), SEQ ID NO:45 (encoding MOR8457-15-VH/MOR8457-16-VH), and SEQ ID NO:47 (encoding MOR8457-15-HC/MOR8457-16-HC).

In another aspect, the invention provides polynucleotides and variants thereof encoding a PDGF-B antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid disclosed herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as $E.\ coli$ or $B.\ subtillis$) and yeast (such as $S.\ cerevisae$, $S.\ pombe$; or $K.\ lactis$). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to PDGF-B is effected by an immunoassay or FACS. A cell overexpressing the antibody or protein of interest can be identified.

An expression vector can be used to direct expression of a PDGF-B antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266: 338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Therapeutic Methods

Therapeutic methods involve administering to a subject in need of treatment a therapeutically effective amount, or "effective amount", of a PDGF-B antibody, or antigen-binding portion, of the invention and are contemplated by the present disclosure. As used herein, a "therapeutically effective", or "effective", amount refers to an amount of an antibody or portion thereof that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents. One of ordinary skill in the art would be able to determine such amounts based on such factors as the subject's size, the severity of the subject's symptoms, and the particular composition or route of administration selected. The subject may be a human or non-human animal (e.g., rabbit, rat, mouse, monkey or other lower-order primate).

An antibody or antigen-binding portion of the invention might be co-administered with known medicaments, and in some instances the antibody might itself be modified. For example, an antibody could be conjugated to an immunotoxin or radioisotope to potentially further increase efficacy. Regarding co-administration with additional therapeutic agents, such agents can include a cytotoxic agent, a radiotoxic agent or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cis-platin bleomycin sulfate, carmustine, chlorambucil, and cyclophosphamide hydroxyurea which, by themselves, are only effective at levels which are toxic or subtoxic to a patient. Cisplatin can be intravenously administered as a 100 mg dose once every four weeks and adriamycin is intravenously administered as a 60 to 75 mg dose once every 21 days. Co administration of the PDGF-B antibodies, or antigen binding fragments thereof, of the present disclosure with a therapeutic agent provides two agents which operate via different mechanisms may provide a therapeutic and perhaps synergistic effect to human disease. Such co-administration can solve problems due to development of resistance to drugs or, in the treatment of tumorigenesis and/or unwanted cell proliferation, a change in the antigenicity of the tumor cells which would render them unreactive with the antibody.

The antibodies and antigen-binding portions disclosed herein can be used as a therapeutic or a diagnostic tool in a variety of situations where PDGF-B is undesirably expressed or found as reviewed in Trojanowska, 2008, Rheumatology 47:v2-v4; Andrae et al. 2008 Genes Dev. 22:1276-1312; Heldin and Westermark, 1999, Physiological Revs. 79(4):1238-1316; Laimer et al., 2012, Nature Med. 18(11):1699-1704; Given the involvement of PDGF-B in tumorigenesis, and the role that PDGF-B plays in angiogenesis, cell proliferation, and cell migration, and excessive deposition of extracellular matrix, as well as the role of PDGFRβ and PDGF-B in numerous diseases, disorders and conditions, many such diseases, disorders or conditions are particularly suitable for treatment with an antibody or antigen-binding portion of the present invention. These diseases, disorders or conditions include, but are not limited to, conditions related to abnormal cell growth, for example, mesothelioma, hepatocarcinoma, prostate carcinoma, adenocarcinoma, glioma, glioblastoma, ovarian carcinoma, cholangiocarcinoma, NPM-ALK-driven lymphomas, colorectal cancer, skin cancer, breast cancer, pancreatic cancer, lung cancer, or a combination of one or more of the foregoing cancers. Further PDGF-B mediated conditions that may be treated with the antibodies, or fragments thereof, of the invention include, but are not limited to, inflammatory conditions (e.g., atherosclerosis, restenosis, osteoarthritis, rheumatoid arthritis, Type 1 diabetes, chronic obstructive pulmonary disease, ischemia, stroke, thrombosis), fibrotic conditions (e.g., idiopathic pulmonary fibrosis, renal disease, biliary fibrosis, liver fibrosis, idiopathic peritoneal fibrosis, glomerulonephritis, IgA nephropathy, lupus nephritis, Alport syndrome, Fanconi disease, focal segmental glomerulosclerosis, hypertensive nephrosclerosis, nephritic disease, scleroderma (SSc), cardiac, hypertrophy, primary biliary sclerosis, Peyronie's disease, uterine fibroids, endometriosis, pulmonary hypertension, post surgical adhesions, dermal scars, pulmonary arterial hypertension, primary sclerosing cholangitis, cardiac allograft vasculopathy and fibrosis); age-related macular degeneration, diabetic macular edema, dry eye, strictures, neointima formation, graft-versus-host-disease, benign prostatic hyperplasia, sarcoma, diabetic nephropathy, vasculitis, anaplastic astrocytoma, mesothelioma, leukemia, brain hemorrhage, fracture healing, cerebral infarction, apoptosis, acquired immune deficiency syndrome/HIV infection, chronic renal failure, cirrhosis, metastasis, primary pulmonary hypertension, secondary pulmonary hypertension, Kawasaki syndrome, reperfusion injury, mucocutaneous lymphy node syndrome, benign tumors, hyperlipidemia, stress incontinence, chronic myeloid leukemia, dermatofibroma, hypersensitivity, medulloblastoma, myeloid leukemia (acute and chronic), osteoporosis, Grave's ophthalmopathy, encephalitis, fibromyalgia, nervous system injury, aging, gallstones, liver disease, hypercholesterolemia, viral meningitis, reprotox, disorders of creatine metabolism, retina disease, systemic lupus erythematosus, malabsorption syndromes, allodynia, malignant hypertension, myelofibrosis, congenital anomalies, ocular toxicity, Alzheimer's dementia, carcinoid, pulmonary fibrosis, nasal polyps, purpura, aneurism, squamous cell carcinoma, chronic pancreatitis, digestive system neoplasm, thyroid neoplasm, atypical pneumonia, frailty, allergy, toxicity, solid tumors, Type II diabetes, dermal scarring, neuroendocrine cancer, asthma, adenoma, neuropathic pain, cytomegalovirus infection, neuroblastoma, retinopathy, atrophy, encephalopathy, shock, CNS cancer, sepsis, hyperoxia, intestinal cancer, bacterial respiratory disease, organ transplantation, pituitary cancer, obesity, keloid scars, nicotine addiction, generalized anxiety disorder, esophageal cancer, basal and squamous cell skin cancer, hypercalcemia, embryonic lethality, pneumonia, lung inflammation, neurological disease, nervous system cancer, Kaposis sarcoma, coagulation disorder, eye disease, pancreatitis, telangiectasia, respiratory disease, ocular and orbital inflammation, cryoglobulinemia, hepatocellular cancer, cardiovascular disorder, and Parkinson's disease.

To treat any of the foregoing disorders, pharmaceutical compositions for use in accordance with the present disclosure may be formulated in a conventional manner using one or more pharmaceutically acceptable carriers or excipients and administered as more fully discussed below.

Determining a therapeutically effective amount of an antibody or antigen-binding portion according to the present disclosure will largely depend on particular patient characteristics, route of administration, and the nature of the disorder being treated and is more fully discussed below.

Administration and dosing of the antibody are more fully discussed elsewhere below.

Diagnostic Methods

The antibodies, engineered antibodies, and engineered antibody conjugates of the invention can be used for diagnostic imaging. For example, the engineered antibody conjugate can be a radiolabeled monoclonal antibody. See, for example, Srivastava (ed.), Radiolabeled Monoclonal Antibodies For Imaging And Therapy, Plenum Press (1988); Chase, "Medical Applications of Radioisotopes," in Remington's Pharmaceutical Sciences, 18th Edition, Gennaro et al. (eds.), Mack Publishing Co., pp. 624-652 (1990); and Brown, "Clinical Use of Monoclonal Antibodies," in Biotechnology and Pharmacy, Pezzuto et al. (eds.), Chapman and Hall, pp. 227-249 (1993); Grossman, 1986, Urol. Clin. North Amer. 13:465-474; Unger et al., 1985, Invest. Radiol. 20:693-700; and Khaw et al., 1980, Science 209:295-297. This technique, also known as immunoscintigraphy, uses a gamma camera to detect the location of gamma-emitting radioisotopes conjugated to monoclonal antibodies. Diagnostic imaging can be used to diagnose cancer, autoimmune disease, infectious disease and/or cardiovascular disease. (See, e.g., Brown, supra.)

In one embodiment, the engineered antibody conjugates can be used to diagnose cardiovascular disease. For example, engineered antibody conjugates comprising anti-myosin antibody fragments can be used for imaging myocardial necrosis associated with acute myocardial infarction, among other uses.

In addition to diagnosis, monoclonal antibody imaging can be used to monitor therapeutic responses, detect recurrences of a disease, and guide subsequent clinical decisions.

For diagnostic and monitoring purposes, radioisotopes may be bound to antibody fragments either directly or indirectly by using an intermediary functional group. Such intermediary functional groups include, for example, DTPA (diethylenetriaminepentaacetic acid) and EDTA (ethylene diamine tetraacetic acid). The radiation dose delivered to the patient is typically maintained at as low a level as possible. This may be accomplished through the choice of isotope for the best combination of minimum half-life, minimum retention in the body, and minimum quantity of isotope which will permit detection and accurate measurement. Examples of radioisotopes which can be bound to antibodies and are appropriate for diagnostic imaging include $^{99}$mTc and $^{111}$In.

Studies indicate that antibody fragments, particularly Fab and Fab', provide suitable tumor/background ratios. (See, e.g., Brown, supra.)

The engineered antibody conjugates also can be labeled with paramagnetic ions for purposes of in vivo diagnosis. Elements which are particularly useful for Magnetic Resonance Imaging include Gd, Mn, Dy, and Fe ions.

The engineered antibody conjugates can also detect the presence of particular antigens in vitro. In such immunoassays, the engineered antibody conjugates may be utilized in liquid phase or bound to a solid-phase carrier. For example, an intact antibody, or antigen-binding fragment thereof, can be attached to a polymer, such as aminodextran, in order to link the antibody component to an insoluble support such as a polymer-coated bead, plate, or tube.

Alternatively, the engineered antibody conjugates can be used to detect the presence of particular antigens in tissue sections prepared from a histological specimen. Such in situ detection can be accomplished, for example, by applying a detectably-labeled immunoconjugate to the tissue sections. In situ detection can be used to determine the presence of a particular antigen and to determine the distribution of the antigen in the examined tissue. General techniques of in situ detection are well known to those of ordinary skill. (See, e.g., Ponder, "Cell Marking Techniques and Their Application," in Mammalian Development: A Practical Approach, Monk (ed.), IRL Press, pp. 115-138 (1987); Coligan et al., supra.)

Detectable labels such as enzymes, fluorescent compounds, electron transfer agents, and the like can be linked to a carrier by conventional methods well known to the art. These labeled carriers and the engineered antibody conjugates prepared from them can be used for in vitro immunoassays and for in situ detection, much as an antibody conjugate can be prepared by direct attachment of the labels to antibody. The loading of the engineered antibody conjugates with a plurality of labels can increase the sensitivity of immunoassays or histological procedures, where only a low extent of binding of the antibody, or antibody fragment, to target antigen is achieved.

Compositions

The invention also provides pharmaceutical compositions comprising an effective amount of a PDGF-B antibody described herein. Examples of such compositions, as well as how to formulate, are also described herein. In some embodiments, the composition comprises one or more PDGF-B antibodies. In other embodiments, the PDGF-B antibody recognizes PDGF-B. In other embodiments, the PDGF-B antibody is a human antibody. In other embodiments, the PDGF-B antibody is a humanized antibody. In some embodiments, the PDGF-B antibody comprises a constant region that is capable of triggering a desired immune response, such as antibody-mediated lysis or ADCC. In other embodiments, the PDGF-B antibody comprises a constant region that does not trigger an unwanted or undesirable immune response, such as antibody-mediated lysis or ADCC. In other embodiments, the PDGF-B antibody comprises one or more CDR(s) of the antibody (such as one, two, three, four, five, or, in some embodiments, all six CDRs).

It is understood that the compositions can comprise more than one PDGF-B antibody (e.g., a mixture of PDGF-B antibodies that recognize different epitopes of PDGF-B). Other exemplary compositions comprise more than one PDGF-B antibody that recognize the same epitope(s), or different species of PDGF-B antibodies that bind to different epitopes of PDGF-B. In some embodiments, the compositions comprise a mixture of PDGF-B antibodies that recognize different variants of PDGF-B or a mixture of PDGF antibodies that recognize a variety of PDGFs, e.g., PDGF-A, -B, -C and -D. In some embodiments, the compositions comprise a single PDGF-B antibody that recognizes epitope 1 and epitope 2 of PDGF-B.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The PDGF-B antibody and compositions thereof can also be used in conjunction with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein. In still other embodiments, the composition comprises either or both of the polynucleotides comprising the sequence shown in SEQ ID NO: 3 and SEQ ID NO: 5, either or both of the polynucleotides shown in SEQ ID NO: 13 and SEQ ID NO: 15, either or both of the polynucleotides shown in SEQ ID NO:35 and SEQ ID NO:45, either or both of the polynucleotides shown in SEQ ID NO:38 and SEQ ID NO:47, either or both of the polynucleotides shown in SEQ ID NO:40 and SEQ ID NO:45, or either or both of the polynucleotides shown in SEQ ID NO:43 and SEQ ID NO:47.

In another aspect, the polynucleotide can encode the VH, VL and/or both of the antibody of the invention. That is, the composition comprises a single polynucleotide or more than one polynucleotide encoding the antibody, or antigen-binding portion thereof, or the invention.

Pharmaceutical compositions of the disclosure also can be administered in combination therapy, such as, combined with other agents. For example, the combination therapy can include an engineered antibody or conjugate thereof of the present disclosure combined with at least one other therapy wherein the therapy may be surgery, immunotherapy, chemotherapy, radiation treatment, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the invention may be prepared, packaged, or sold in a formulation suitable for ophthalmic administration. Such formulations may, for example, be in the form of eye drops including, for example, a 0.1 1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences, Genaro, ed., Mack Publishing Co., Easton, Pa. (1985), which is incorporated herein by reference.

In one embodiment, the antibody, engineered antibody or engineered antibody conjugate is administered in an intravenous formulation as a sterile aqueous solution containing 5 mg/m, or more preferably, about 10 mg/ml, or yet more preferably, about 15 mg/ml, or even more preferably, about 20 mg/ml of antibody, with sodium acetate, polysorbate 80, and sodium chloride at a pH ranging from about 5 to 6. Preferably, the intravenous formulation is a sterile aqueous solution containing 5 or 10 mg/ml of antibody, with 20 mM sodium acetate, 0.2 mg/ml polysorbate 80, and 140 mM sodium chloride at pH 5.5. Further, a solution comprising an engineered antibody or engineered antibody conjugate can comprise, among many other compounds, histidine, mannitol, sucrose, trehalose, glycine, poly(ethylene) glycol, EDTA, methionine, and any combination thereof, and many other compounds known in the relevant art.

In one embodiment, part of the dose is administered by an intraveneous bolus and the rest by infusion of the antibody, engineered antibody or engineered antibody conjugate formulation. For example, a 0.01 mg/kg intravenous injection of the antibody, engineered antibody or engineered antibody conjugate may be given as a bolus, and the rest of a predetermined engineered antibody or engineered antibody conjugate dose may be administered by intravenous injection. A predetermined dose of the antibody or engineered antibody may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

Dosing/Administration

To prepare pharmaceutical or sterile compositions including an antibody, engineered antibody or engineered antibody conjugate of the disclosure, the antibody/antibody conjugate is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising antibodies, engineered antibodies or engineered antibody conjugates of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346: 1692-1698; Liu, et al., 1999, J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies or engineered antibodies or engineered antibody conjugates of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibody or engineered antibodies or engineered antibody conjugates of the disclosure may be calculated using the patient's weight in kilograms (kg) multiplied by the dose to be administered in mg/kg. The dosage of the antibodies of the disclosure may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.1 µg/kg or less of a patient's body weight.

Unit dose of the engineered antibodies or engineered antibody conjugates of the disclosure may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies, engineered antibodies or engineered antibody conjugates of the disclosure may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 v, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml/ml, or at least 400 µg/ml/ml in a subject. Alternatively, the dosage of the antibodies of the disclosure may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies, engineered antibodies or engineered antibody conjugates of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK). The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316, 024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934, 272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an engineered antibody or engineered antibody conjugate, combination therapy, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the antibodies, engineered antibodies or engineered antibody conjugates of the disclosure are administered in a controlled release or sustained release system, a pump may be used to achieve controlled or sustained release (see Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 71: 105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), polyvinyl alcohol), polyacrylamide, polyethylene glycol), polylactides (PLA), polyoeactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et ah, 1997, "Biodegradable Polymeric Carriers for a bFGF Antibody for Cardiovascular Application," Pro. MI. Symp. Control. Rel. Bioact. Mater. 24:853-854, and Lam et al., 1997, "Microencapsulation of Recombinant Humanized Monoclonal Antibody for Local Delivery," Proc. MI. Symp. Control Rel. Bioact. Mater. 24:759-160, each of which is incorporated herein by reference in their entirety.

If the antibody, engineered antibody or engineered antibody conjugate of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising antibodies, engineered antibodies or engineered antibody conjugates are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10 th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.). An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with the engineered antibodies or engineered antibody conjugates of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

The antibodies, engineered antibodies or engineered antibody conjugates of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies, engineered antibodies or engineered antibody conjugates of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); pI20 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising antibodies, engineered antibodies or engineered antibody conjugates of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies, engineered antibodies or engineered antibody conjugates of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Kits

The invention also provides kits comprising any or all of the antibodies described herein. Kits of the invention include one or more containers comprising a PDGF-B antibody described herein and instructions for use in accordance with any of the methods of the invention described herein. Generally, these instructions comprise a description of administration of the antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered pre-filled syringes (e.g., liquid syringes and lyosyringes), are included.

In some embodiments, the antibody is a human antibody. In some embodiments, the antibody is a humanized antibody. In some embodiments, the antibody is a monoclonal antibody. The instructions relating to the use of a PDGF-B antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PDGF-B antibody of the invention. The container may further comprise a second pharmaceutically active agent.

Kits may optionally provide additional components such as buffers and interpretive information. Normally, the kit comprises a container and a label or package insert(s) on or associated with the container.

The invention also provides diagnostic kits comprising any or all of the antibodies described herein. The diagnostic kits are useful for, for example, detecting the presence of PDGF-B in a sample. In some embodiments, a diagnostic kit can be used to identify an individual with a latent disease, disorder or condition that may put them at risk of developing PDGF-B mediated disease, disorder or condition. In some embodiments, a diagnostic kit can be used to determine whether an individual is at risk for a staphylococcal disease. In some embodiments, a diagnostic kit can be used to detect the presence and/or level of PDGF-B in an individual suspected of having a PDGF-B mediated disease.

Diagnostic kits of the invention include one or more containers comprising a PDGF-B antibody described herein and instructions for use in accordance with any of the methods of the invention described herein. Generally, these instructions comprise a description of use of the PDGF-B antibody to detect the presence of PDGF-B in individuals at risk for, or suspected of having, a PDGF-B mediated disease. In some embodiments, an exemplary diagnostic kit can be configured to contain reagents such as, for example, a PDGF-B antibody, a negative control sample, a positive control sample, and directions for using the kit.

Biological Deposit

Representative materials of the present invention were deposited in the American Type Culture Collection, 10801 University Boulevard, Manassas, Va. 20110-2209, USA, on Nov. 6, 2012. Vector MOR8457-GL-VH having ATCC Accession No. PTA-13303 comprises a DNA insert encoding the germlined MOR8457 heavy chain variable region, and vector MOR8457-GL-VL having ATCC Accession No. PTA-13302 comprises a DNA insert encoding the germlined MOR8457 light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Equivalents

The foregoing written specification is considered to be sufficient to enable one skilled in the art to practice the disclosure. The foregoing description and Examples detail certain exemplary embodiments of the disclosure. It will be appreciated, however, that no matter how detailed the foregoing may appear in text, the disclosure may be practiced in many ways and the disclosure should be construed in accordance with the appended claims and any equivalents thereof.

All references cited herein, including patents, patent applications, papers, text books, and the like, and the references cited therein, to the extent that they are not already, are hereby incorporated herein by reference in their entirety.

Exemplary Embodiments

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Antibody Generation from HuCAL® Libraries

For the generation of therapeutic antibodies against PDGF-BB, selections with the MorphoSys HuCAL GOLD® phagemid library were carried out. The phagemid library is based on the HuCAL® concept (Knappik et al., J Mol Biol, 2000, 296; 57-86 and employs the CysDisplay™ technology for displaying the Fab on the phage surface (Lohning, 2001 WO 01/05950 HuCAL GOLD® antibody-phage of different frameworks were either combined to form one pool (VH1-6) or were divided into sub-pools (e.g., VH1/5, VH2/4/6, VH3) and subsequently these sub-pools were individually subjected to selection rounds on antigen as described below. For those phage pools which were also used for in-line affinity maturation kappa and lambda phage were kept separated. Phage for the 1st round of pannings were prepared by Hyperphage (M13KO7ΔpIII, Progen, Heidelberg, Germany).

Solid Phase Panning Against PDGF-BB

Solid phase panning was performed using recombinant human PDGF-BB (PHG0043, Lot 032001; Biosource Int. Inc.). For all three rounds of pannings 400 nM (10 µg/ml) hPDGF-BB diluted in PBS was filled into an appropriate number of wells on Maxisorp plates (F96 Maxisorp™, 442402, Nunc).

Respective plates were then incubated overnight at 4° C. On the next day, the wells were washed twice with PBS and then blocked with MPBST (5% (w/v) milk powder, PBS, 0.05% Tween20 (Sigma, St. Louis, Mo., USA)) for 2 hours at room temperature (RT). Phage (100 µl) from original HuCAL GOLD® subpools (VH1-6, VH1/5 and VH3, prepared with hyperphage) were used. Phage were pre-blocked in a PBS solution containing 2.5% milk powder, 2.5% bovine serum albumin (BSA) and 0.05% Tween20. The pre-blocking of phage was performed in 2 ml reaction tubes for 2 hours at RT on a rotator.

In order to select antibodies which did not bind to PDGF-AA phage of each subpool were pre-blocked in a PBS solution containing a 10-fold molar excess of PDGF-AA (PHG0035, Biosource Int. Inc.), 2.5% milk powder, 2.5% BSA and 0.05% Tween20 in a parallel approach.

For the selection process the antigen solution was removed from the plate and the wells were washed three times with PBS. The pre-blocked phage were added to the corresponding wells and the plate was incubated for 2 hours at RT on a microplate shaker. Then, the phage solution was removed and the wells were washed several times (the washing stringency depended on the panning strategy and the selection round) with PBST (PBS, 0.05% Tween20), followed by the same washing steps with PBS. The washing stringency was increased from round to round. PBS was removed after the last washing step before continuing with elution. For elution of specifically bound phage 20 mM dithiothreitol (DTT) in 10 mM Tris/HCl, pH 8.0 was added and the samples were incubated for 10 minutes at RT. The eluates were used to infect log phase E. coli TG1 cultures. Infected E. coli were harvested by centrifugation and plated onto LB agar plates supplemented with 34 µg/ml chloramphenicol and 1% glucose. The agar plates were incubated overnight at 30° C. On the following day the colonies were scraped off and grown until reaching an OD600 of 0.5 to proceed to helper phage infection.

Helper phage infection: TG1 cells were infected with the helper phage VCSM13 (multiplicity of infection of at least 20) at 37° C. The infected cells were harvested by centrifugation and resuspended in 2× YT medium containing 34 µg/ml chloramphenicol, 50 µg/ml kanamycin and 0.25 mM IPTG (isopropyl-R-D-thiogalactopyranoside) for induction of Fab expression. The cells were grown overnight and the phage produced were precipitated from the supernatant with polyethylene glycol (PEG)/NaCl and the phage were resuspended in PBS. Input and output titers were determined by spot titration.

Solution Panning Against PDGF-BB

All tubes used for the selections were pre-blocked with ChemiBLOCKER (Chemicon, Temecula, Calif., USA). HuCAL GOLD® phage were blocked with ChemiBLOCKER (+0.05% Tween20) and pre-adsorbed twice on M-280 Streptavidin Dynabeads® (Dynal Biotech, Oslo, Norway). Pre-blocked phage and biotinylated PDGF-BB (biotin-PDGF-BB) antigen were incubated in a 2 ml tube for 2 hours at RT on a rotator. For the first selection round, 100 nM biotin-hPDGF-BB was used for bead coupling. Second and third panning round was performed using 10 nM biotin-hPDGF-BB. For those pannings, PDGF-AA was used as a competitor at 10 fold molar excess of PDGF-AA was used for pre-blocking of phage.

Pre-adsorbed Streptavidin Dynabeads® were added to the phage-antigen solution and incubated for further 10 min at RT on a rotator. A magnetic particle separator, MPC-E (Dynal Biotech, Oslo, Norway), was used to separate phage bound to the captured antigen. The beads were washed several times with PBST (PBS, 0.05% Tween 20), followed by several washing steps with PBS. The washing stringency was increased with every panning round. PBS was removed after the last washing step before continuing with elution. Elution and further steps were performed as described for solid phase panning.

In-Line Affinity Maturation Using RapMAT™ Technology

In order to obtain specific antibodies with improved affinities of enriched HuCAL GOLD® Fabs binding to PDGF-BB, second round output phage of solution pannings described in above were used for LCDR3 diversification. Plasmid DNA of the phage display vector encoding Fab fragments from the 2nd round panning pools were prepared by using the Qiagen Midiprep Kit (Cat. No. 12243). For LCDR3 RapMAT™-libraries, the DNA was cut with BbsI and SphI, thereby releasing the LCDR3-CL insert, and separated on a 1% agarose gel. HCDR2 RapMAT™-libraries were performed by cutting the DNA with EcoRI and XbaI thus releasing the HCDR2-CH insert which was also separated from the vector backbone on a 1% agarose gel.

The expected band of the pMORPH®23 vector backbone (~4650 bp) was excised from the gel and purified using Easy Pure Kit (Biozyme; Cat. No. 390001). Vector backbones were ligated with HuCAL® kappa or lambda light chain CDR cassettes or HuCAL® heavy chain CDR cassettes, respectively, at a molar ratio of 1:4. E. coli Top10F electrocompetent cells were transformed with the ligation samples. For amplification of the HCDR2 and LCDR3 libraries, 2×YT medium containing 34 µg/ml chloramphenicol and 1% glucose was inoculated with transformed cells and cultures were grown until reaching an OD600 nm of 1.5-2.0. Cells were pelleted and resuspended in glycerol medium. Phage of generated kappa and lambda libraries were combined prior use. Pre-blocking of phage was done in a blocking solution (PBS, 10% milk powder, 10% BSA, 10% human transferrin, and 0.2% Tween20). Third and fourth rounds of solution pannings were done as described above. In order to enrich for high affinity antibodies, the antigen concentration of biotin-PDGF-BB was lowered using 0.5 nM of biotin-PDGF-BB for bead coupling in 3rd round and 0.025 nM of biotin-PDGF-BB in the 4th round. The washing stringency was increased.

Subcloning and Microexpression of Selected Fab Fragments

To facilitate rapid expression of soluble Fab, the Fab encoding inserts of the selected HuCAL GOLD® phage were subcloned via XbaI and EcoRI into the expression vector pMORPH@X9_MH. After transformation of the expression plasmids into E. coli TG1 F- cells, chloramphenicol-resistant single clones were picked into the wells of a sterile 384-well microtiter plate pre-filled with 2×YT medium (supplemented with 34 µg/ml chloramphenicol and 1% glucose) and grown overnight at 37° C. These plates were regarded as masterplates. Before storage of the masterplates at −80° C., the E. coli TG1 F- cultures were inoculated into new, sterile 384-well microtiter plates pre-filled with 40 µl 2×YT medium supplemented with 34 µg/ml chloramphenicol and 0.1% glucose per well. The microtiter plates were incubated at 30° C. shaking at 400 rpm on a microplate shaker until the cultures were slightly turbid (~2-4 h) with an OD600 nm of ~0.5. These plates were regarded as expression plates, and 10 µl 2×YT medium supplemented with 34 µg/ml chloramphenicol and 5 mM IPTG was added per well (end concentration 1 mM IPTG), the microtiter plates were sealed with a gas-permeable tape, and incubated overnight at 30° C. shaking at 400 rpm. Generation of whole cell lysates (BEL extracts): To each well of the expression plates, 15 µl BEL buffer was added and incubated for 1 h at 22° C. on a microtiter plate shaker (400 rpm). BEL buffer: 24.7 g/l boric acid, 18.7 g NaCl/l, 1.49 g EDTA/l, pH 8.0 supplemented with 2.5 mg/ml lysozyme.

Example 2

Screening of PDGF-BB Positive Clones

PDGF-BB positive clones were identified by screening clones for antigen binding using ELISA as well as functional PDGF-BB inhibitory activity using a receptor inhibition assay in parallel.

Methods

Screening on Directly Coated PDGF-BB

Human PDGF-BB was used for overnight coating of Maxisorp microtiter plates at 4° C. at a concentration of 5 µg/ml (diluted in PBS). After overnight incubation, coated plates were washed twice with PBST (PBS/0.05% Tween20) and blocked with 5% MPBST (5% milk powder in PBST) for 1 hour at RT on a microplate shaker. The plates were washed twice with PBST before primary antibodies were added (crude extracts of microexpressed HuCAL® Fabs, purified HuCAL® Fabs, control antibody Fab_MOR07295). The plates containing the primary antibodies were incubated for 1 hour at RT on a microplate shaker. The plates were washed twice with PBST and for the detection of HuCAL® Fabs, the secondary antibody (Goat anti-human F(ab)2-Fragment specific—AP labeled, Jackson Cat. No. 109-055-097) was added, diluted 1:5000 in 0.5% MPBST (0.5% milk powder in PBST). The plate containing the secondary antibodies was incubated for 1 hour at RT on a microplate shaker. The wells were washed five times with TBST (TBS/0.05% Tween20), Attophos (AttoPhos Substrate Set, Roche, Cat. No. 11681982001) was added (diluted 1:10 in water) and fluorescence emission at 535 nm was recorded with excitation at 430 nm.

Capture Screening Using Biotinylated PDGF-BB

Maxisorp (Nunc, Rochester, N.Y., USA) 384 well plates were coated with 20 µl sheep anti-human IgG, Fd fragment specific, antibody diluted 1:1000 in PBS, pH 7.4 for 16 h at 4° C. Plates were washed twice with PBST (PBS/0.05% Tween20) and then blocked with 5% MPBST (5% milk powder in PBST) for 1 hour at RT on a microplate shaker. Plates were washed twice with PBST (PBS/0.05% Tween20) before primary antibodies were added (crude extracts of microexpressed HuCAL® Fabs, purified HuCAL® Fabs, control antibody Fab_MOR07295) and incubated for 1 hour at RT on a microplate shaker. Plates were washed twice with PBST (PBS/0.05% Tween20) and biotin-PDGF-BB antigen (0.5 µg/ml diluted in PBS) was incubated for 1 hour at RT on a microplate shaker. Plates were washed twice with PBST (PBS/0.05% Tween20) followed by incubation of Streptavidin-AP, (Zymed; Cat. No. 43-8322; Lot: 51102099; 1:2000 diluted in 0.5% MPBS) for 1 hour at RT on a microplate shaker. Finally the wells were washed five times with TBST (TBS/0.05% Tween20), Attophos (AttoPhos Substrate Set, Roche, Cat. No. 11681982001) was added (diluted 1:10 in ddH20) and fluorescence emission at 535 nm was recorded with excitation at 430 nm.

Functional Screening Using Receptor Inhibition Assay

A 384 well MSD plate was coated with 2.5 µg/ml PDGF-Rβ-Fc fusion protein (Cat. No. 385-PR, R&D Systems) overnight at 4° C. Next, 20 µl of E. coli crude extract was preincubated with 20 µl of 30 ng/ml biotin-PDGF-BB diluted in BV-buffer (PBS/0.02% Tween20/0.5% BSA) for 1 hour at RT on a microplate shaker. MSD plates were washed three times with 50 µl BV-buffer followed by transfer of the preincubated crude extract: biotin-PDGF-B complex. Plates were incubated 1 hour at RT on a microplate shaker followed by three times washing with BV-buffer. Plates were incubated for 1 hour at 37° C. using Streptavidin-BV (1:400 diluted in BV-buffer) followed again by 3 washes with BV-buffer and addition of 30 µl of MSD read buffer cont. surfactant (MSD, 1:4 diluted in dH2O). Detection was performed using a MSD MA6000 device.

Results

In total, 9568 primary hits were screened for antigen binding using ELISA and for inhibition of PDGF-BB/PDGFRβ—Fc binding in parallel. In binding assays, 6008 primary ELISA hits (from all panning strategies) showed signal 5 fold over background. Of these, 2949 primary hits showed signal of more than 80% inhibitory activity in the receptor binding inhibition assay. These hits were ranked on the basis of their ELISA activity, and 540 clones were selected for variable region sequencing. Sequence analysis resulted in 168 unique sequences.

Example 3

Characterization of HuCAL GOLD® Fabs and IgGs

Selected HuCAL GOLD® Fabs and IgGs were further characterized using several assays as described below, as well as with the ELISA techniques as described in Example 2.

Methods

Solution Equilibrium Titration (STE) Method for $K_D$ Determination and Cross-Reactivity Studies Affinity determination in solution was performed as described in the literature (Friguet et al., 1985, J. Immunol. Methods 77:305-319). In order to improve the sensitivity and accuracy of the SET method, it was transferred from classical ELISA to electrochemiluminescence (ECL) based BioVeris technology (Haenel et al., 2005, Anal. Biochem. 339:182-184). Goat-anti-human (Fab)$_2$ or goat-anti-mouse IgG, Fc fragment specific antibodies (Jackson Immuno Research) were labeled with BV-tag™ NHS-Ester (Bioveris Europe, Witney, Oxfordshire, UK) according to manufacturer's instructions. The experiments were carried out in polypropylene microtiter plates and PBS pH 7.4 with 0.5% BSA and 0.02% Tween 20 as assay buffer. Unlabeled antigen was diluted in 4n series. Wells without antigen were used to determine Smax values. After addition of 100 pM Fab or IgG (final concentration in 75 µL final volume), the mixture was incubated for 2 hours at RT. Subsequently, a mixture of 25 µl Dynabeads (0.4 mg/ml M-280 Streptavidin, DYNAL, Hamburg), coated with 0.25 µg/ml biotinylated antigen and BV-tag labeled detection antibody in a final dilution of 1:4000 for anti-human Fab or 1:2000 for anti-mouse IgG were added per well. After incubation for 30 min on an Eppendorf shaker (700 rpm) at RT, ECL signals were detected using a M-384 SERIES® Workstation (Bioveris Europe). Data were evaluated with Origin 5.0 (Microcal) software applying customized fitting models (for Fab: Haenel et al., 2005; for IgG: Piehler et al., 1997).

Expression and Purification of HuCAL-Fab Antibodies in E. coli

Expression of Fab fragments encoded by pMORPHX9_FH in TG-1 F- cells was carried out in shaker flask cultures with 1 l of 2×TY medium supplemented with 34 µg/ml chloramphenicol. After induction with 0.5 mM IPTG, cells were grown at 30° C. for 20 hours. Whole cell lysis (Lysozyme) of cell pellets was prepared and Fab fragments were isolated by HT-IMAC-purification. The apparent molecular weights were determined by size exclusion chromatography (SEC) with calibration standards. Concentrations were determined by UV-spectrophotometry.

PAE-PDGF-Rβ Phosphorylation Assay

PDGF-Rβ receptor phosphorylation by PDGF-BB ligand was analyzed using PAE cells stably transfected with PDGF-Rβ cultured in culture medium (F12 Nutrient ham medium with L-Glutamine (Gibco; Cat. No. 21765) supplemented with 10% FBS (PAN Biotech, Lot P250112), 2 mM L-Glutamine (PAA, Cat. No. P04-80100) and 500 µg/ml geneticin (PAA; Cat. No. P11-012). One day before assay start, 5×10$^5$ cells/well were seeded into 96-well plates (Nunclon #167008). After 6 hours, culture medium was exchanged to starving medium (culture medium cont. 0.1% FBS) and incubated overnight. On the next day different concentrations of antibodies (30 nm-1.5 pM) were preincubated with 0.4 nM PDGF-BB (final conc.) diluted in starving medium. Supernatant of cells was discarded and antibody: PDGF-BB complexes were added to the cells. After exactly 10 minutes at 37° C. (in the incubator), cells were washed once with ice cold PBS followed by cell lysis using MSD cell lysis buffer. Phosphorylation of Tyr751 of PDGF-Rβ was quantified using MSD Multispot PDGFRbeta whole cell lysis kit (Mesoscale Discovery) using the manufacturer's protocol.

Affinity Determination (Biacore)

The kinetic constants kon and koff were determined with serial dilutions of the respective Fab binding to covalently immobilized antigen PDGF-BB using the BIAcore 3000 instrument (Biacore, Uppsala, Sweden). For covalent antigen immobilization standard EDC-NHS amine coupling chemistry was used. Kinetic measurements were done in PBS (136 mM NaCl, 2.7 mM KCl, 10 mM Na2HPO4, 1.76 mM KH2PO4, pH 7.4) at a flow rate of 20 µl/min using Fab concentration range from 1.5-500 nM. Injection time for each concentration was 1 minute, followed by 3 minutes dissociation phase. For regeneration 5 µl 10 mM HCl was used. All sensorgrams were fitted using BIA evaluation software 3.1 (Biacore).

Results
Binding and Specificity

All 168 unique clones were used for SET affinity ranking and compared to MOR0729511 control clone. Forty one clones (selected in consideration of sequence diversity and panning origin) with the best affinities were selected for consolidation. After Fab expression and purification, 37 passed quality control criteria and were tested further.

All 37 Fabs were specific for human PDGF-BB (hPDGF-BB) and cross reactive to murine PDGF-BB (mPDGF-BB). None of the 37 Fabs showed binding to PDGF-AA by ELISA.

Inhibitory Activity

All 37 Fabs were tested for their inhibitory activity in receptor phosphorylation assay. Stably transfected PAE PDGF-Rβ cells constitutively express the PDGF-β receptor and can be stimulated by PDGF-BB resulting in the receptor phosphorylation on position Tyr751. For detection of phosphorylation a Phospho-PDGFRbeta kit (Mesoscale Discovery) was used based on detection of P-Tyr751 by a specific anti-P-Tyr751 antibody.

To narrow down the number of Fabs to be titrated all 37 antibodies were initially tested at only 4 concentrations for their ability to inhibit phosphorylation activity. Of these, 3 Fabs were determined to be less active, thus, 34/37 Fabs were used for full titration.

Full titration of Fabs was performed from 60 nM to 27 pM or 10 nM to 13 pM in 1:3 steps and used for pre-incubation of 400 pM (10 ng/ml) PDGF-BB resulting in a theoretical assay sensitivity limit of 200 pM. Mean values of triplicates were used for IC50 determination.

TABLE 1

Summary of PDGF-BB inhibition for 34 selected Fabs

| MOR# | IC50 [nM] |
|---|---|
| 8447 | 0.38 |
| 8448 | 0.5 |
| 8449 | 0.59 |
| 8450 | 0.57 |
| 8451 | 0.34 |
| 8452 | 0.27 |
| 8454 | 0.23 |
| 8456 | 1.1 |
| 8457 | 0.32 |
| 8458 | 1 |
| 8459 | 0.38 |
| 8462 | 0.49 |
| 8463 | n.d. |
| 8465 | 0.59 |
| 8467 | 0.31 |
| 8468 | n.d. |
| 8469 | 0.35 |
| 8470 | 1.16 |
| 8471 | 2.12 |
| 8475 | 1.44 |
| 8476 | n.d. |
| 8477 | 0.44 |
| 8478 | 0.73 |
| 8479 | 4.6 |
| 8480 | 0.6 |

TABLE 1-continued

Summary of PDGF-BB inhibition for 34 selected Fabs

| MOR# | IC50 [nM] |
|---|---|
| 8481 | 0.68 |
| 8484 | 2.02 |
| 8486 | 0.41 |
| 8487 | 0.22 |
| 8488 | 0.68 |
| 8489 | 0.63 |
| 8490 | 0.2 |
| 8493 | 0.28 |
| 8494 | 0.44 |
| 8495 | 1.3 |
| 8497 | 0.25 |
| 8498 | 0.29 |
| 7295 | 0.28 |

Data from the phosphorylation assay, and biochemical receptor binding inhibition assay were used to narrow the panel of Fabs from 37 to 16. Of these, 4 Fabs, consistently inhibited proliferation of NIH3T3 cells: MOR8457, MOR8494, MOR8487 and MOR8488. The lead sequences were further narrowed to remove those which contained potential chemical liabilities such as free cysteine, and Asp-Pro cleavage sites.

Thus, the procedures described above in Examples 1 to 3 were used to produce several fully human anti-PDGF-BB IgG antibodies, including antibodies designated as MOR8457 and variants thereof which are described herein.

The amino acid sequence of MOR8457 variable heavy domain is:

(SEQ ID NO: 1)
EVQLVESGGGLVQPGGSLRLSCAASGFTFSSYAMSWVRQAPGKGLEWV

SYISDDGSLKYYADSVKGRFTISRDNSKNTLYLQMNSLRAEDTAVYYC

ARHPYWYGGQLDLWGQGTLVTVSS

The amino acid sequence of MOR8457 variable light domain is:

(SEQ ID NO: 2)
SYELTQPPSVSVAPGQTARISCSGDSLGSYFVHWYQQKPGQAPVLVIYD

DSNRPSGIPERFSGSNSGNTATLTISGTQAEDEADYYCSAFTHNSDVFG

GGTKLTVL

Example 4

Expression of Full Length IgG

In order to express full length IgG, variable domain fragments of heavy (VH) and light chains (VL) were subcloned from Fab expression vectors into appropriate vectors for expression as human IgG. In some cases, a synthetic DNA insert encoding the variable region of the heavy or light chain of the anti-PDGF-BB antibodies was created via commercial gene synthesis. Fragments were subcloned in-frame with human or mouse constant regions into expression vectors for transient expression. Depending on the application, the constant regions consisted of human wild type IgG2 (SEQ ID NO:22), wild-type human IgG1 (SEQ ID NO:19), a human IgG1 with targeted mutations to ablate effector function termed "IgG1-3 m" (SEQ ID NO:21), or mouse IgG1 (SEQ ID NO:20). In some cases, MOR8457 was constructed with a light chain comprising germlined MOR8457 VL (SEQ ID NO:4) and further comprising an inadvertent sequence alteration in the light chain constant domain wherein the amino acid sequence TLV was substituted by IKR as the result of a PCR cloning error. The full length light chain comprising germlined MOR8457 VL and the light chain constant lambda domain comprising the IKR mutation was designated "MOR8457-GL-IKR-LC" (SEQ ID NO:17). Any antibody comprising a light chain constant domain comprising the "IKR" mutation is designated herein by including "IKR" in the name. Thus, the antibody comprising a light chain comprising the germlined MOR8457 VL sequence (SEQ ID NO:4) and further comprising the constant domain comprising the IKR sequence alteration in the constant domain (SEQ ID NO:17) and comprising a heavy chain comprising the germlined MOR8457 VH (SEQ ID NO:6) further comprising the human IgG1 triple effector null mutation in the constant region (SEQ ID NO:14) is referred to herein as antibody "MOR-8457-GL-IKR-hIgG1-3 m". An antibody comprising at least one germlined V domain, is referred to herein by the designation of "GL", and any antibody not comprising a germlined domain does not include that designation in its name. More preferably, both VH and VL domains are germlined where the antibody is designated as "GL."

Transient Expression and Purification of Full Length IgG

Transient expression of full length IgG was performed in HKB11 or HEK-293F cells, which were transfected with expression vectors encoding the heavy and light chains separately. Cell culture supernatant was harvested three to seven days after transfection and cleared by centrifugation.

After filtration (0.22 μm or 0.45 μm), the supernatant was subjected to standard protein A or G affinity chromatography (MabSelect SURE, GE). Proteins were eluted at pH 3 and neutralized in 3 M TRIS, pH 8. Further downstream processing involved buffer exchange to 1× Dulbecco's PBS (Invitrogen) and sterile filtration (0.2 μm; Millipore or Sartorius). Purity was analyzed under denaturing, reducing and denaturing, non-reducing conditions in SDS-PAGE or by capillary electrophoresis. HP-SEC was performed to analyze IgG preparations in their native state.

Example 5

Design and Generation of Genes Encoding a Germlined Antibody Variant of MOR8457

The Morphosys HuCAL library was constructed using consensus sequences derived from seven heavy and seven light chain variable regions, respectively. Thus, the lead sequences which were obtained from this library contain amino acids at multiple positions which differ from their human germline counterparts, and could represent a theoretical immunogenicity risk. Mutation of the sequence at these non-germline positions back to the germline residues (termed "germlining") was performed to eliminate this potential liability.

The variable chain sequences of the phage derived MOR-8457 lead were compared to those available in the ImmunoGenetics (IMGT) immunoglobulin repertoire. The most appropriate human heavy (FIG. 1A) and light chain (FIG. 1B) germline variable sequence was identified by alignment. FIGS. 1A and 1B show the alignments and the percent shared sequence identity between the MOR8457$V_H$ (FIG. 1A) and $V_L$ (FIG. 1B) and each of the various germline sequences.

Germlining of Heavy Chain V Domain

For germlining of the MOR-8457 heavy chain (SEQ ID NO:2), the germline variable region encoded by IMGT IGHV3-23*01 (DP-54; SEQ ID NO:25), sharing 98.6% sequence identity, was determined to be the most appropriate. As depicted in FIG. 1A, the framework regions of this variable gene contain the following substitutions V5L and R94K (Kabat numbering). Thus, a new germlined heavy chain V domain sequence (hereinafter referred to as "MOR8457-GL-VH", SEQ ID NO:6) was selected by replacing each of the substituted amino acids with those from the DP-54 germline variable region.

Germlining of Light Chain V Domain

For germlining of the MOR-8457 light chain (SEQ ID NO:1), the germline variable region encoded by IMGT IGLV3-1*01 (DPL-23; SEQ ID NO:29), sharing 92.7% sequence identity with MOR8457 VL, was determined to be the most appropriate. As depicted in FIG. 1B, the framework regions of this variable gene contain substitutions at five positions: A14S, R20S, S22T, A43S and E81M (Kabat numbering) compared with MOR8457 (SEQ ID NO:1). Thus, a new germlined sequence (hereinafter referred to as "MOR8457-GL-VL", SEQ ID NO:4) was selected by replacing each of the substituted amino acids with those from the DPL-23 germline variable region.

Example 6

Characterization of MOR-8457 and Sequence Variants as IgGs

Binding Affinity, Specificity and Cross Species Reactivity of MOR8457

The binding affinities of three IgG variants of MOR8457 were determined using a Biacore 2000 (GE Healthcare, Piscataway N.J.). One variant antibody, referred to as "MOR8457-IKR-hIgG1-3 m", comprises a full length heavy chain (MOR8457-hIgG1-3m-HC; SEQ ID NO:18) comprising the original MOR8457$V_H$ region sequence (SEQ ID NO:2) and a human IgG1 heavy chain constant domain containing an effector function null mutation (MOR8457-hIgG1-3m; SEQ ID NO:21) and a full-length light chain (SEQ ID NO:17; MOR8457-IKR-LC) comprising the original $V_L$ region sequence (SEQ ID NO:1) and a human lambda light chain constant domain (CA; SEQ ID NO:23) wherein the light chain sequence comprises an inadvertent sequence mutation as described previously elsewhere herein.

Another variant, referred to as "MOR8457-mIgG1", comprises a full length heavy chain comprising the original MOR8457$V_H$ region sequence (SEQ ID NO:2) and further comprises a mouse wild type IgG1 heavy chain constant domain (SEQ ID NO:20) to provide a full-length heavy chain termed "MOR8457-mIgG1-HC". The MOR8457-mIgG1 antibody further comprises a full-length light chain (MOR8457-m-LC) comprising the original MOR8457$V_L$ region sequence (SEQ ID NO:1) and a mouse wild type lambda constant domain (SEQ ID NO:24).

Yet another variant MOR8457 antibody, termed "MOR8457-GL-hIgG1-3 m", was constructed which comprises a full-length heavy chain (MOR8457-GL-hIgG1-3m-HC; SEQ ID NO:14) comprising the germlined MOR8457$V_H$ region sequence (MOR8457-GL-VH; SEQ ID NO:6) and a human IgG1 heavy chain constant domain containing an effector function null mutation (hIgG1-3m; SEQ ID NO:21) and the antibody further comprises a full-length light chain (SEQ ID NO:16; MOR8457-GL-LC) comprising the germlined MOR8457$V_L$ region sequence (SEQ ID NO:4; MOR8457-GL-VL) and the wild type human lambda light chain constant domain (SEQ ID NO:23).

MOR8457 Antibodies are Specific for PDGF-BB

In order to test the specificity and cross species reactivity, the binding affinities of three MOR8457 IgG variants, MOR8457-IKR-hIgG1-3m, MOR8457-mIgG1, and MOR8457-GL-hIgG1-3m, to different human PDGF ligands, including human PDGF-AA, -AB, -DD, as well as rat PDGF-BB (all obtained from R&D systems, Minneapolis, Minn.) and mouse PDGF-BB (Invitrogen, Carlsbad, Calif.) were tested. Briefly, anti-human or anti-mouse IgG (GE Healthcare) antibodies were immobilized in adjacent flow cells of a CM5 sensor chip between 8000-10,000 resonance units (RU) using amine coupling as directed by the manufacturer. Antibodies were diluted into PBS-NET (10 mM Phosphate pH 7.4, 287 mM NaCl, 2.7 mM KCl, 3.2 mM EDTA, 0.01% Tween 20) to 1 µg/mL and injected independently over the respective anti-human or anti-mouse surface for 10 seconds resulting in a stable anti-PDGF surface between 50-100 RU. PDGF proteins were diluted to 1 nM in PBS-NET and serially diluted two-fold to 0.25 nM. Each concentration of PDGF was then injected over the antibody surface for 2 minutes at a flow rate of 100 µl/min. The complex was allowed to dissociate for 10 minutes. The surface was regenerated with a 30 second injection of 10 mM magnesium chloride leaving the surface ready for another round of anti-PDGF antibody capture and PDGF binding kinetics. Kinetic data were double referenced (Myszka et al., 1999, J. Mol. Recognit. 12 279) using scrubber2 software (Bio-Logic Software), then fit to a 1:1 binding model using Biacore evaluation software version 4.1. The results shown were an average of three independent binding studies. FIG. 2 shows representative sensorgrams and Table 2 summarizes the binding affinities.

PDGF-BB binds to homodimeric PDGFR-αα and PDGFR-ββ receptor complex as well as to heterodimeric PDGFR-αβ receptor complex, while PDGF-AB binds to homodimeric PDGFR-αα and heterodimeric PDGFR-αβ receptors to trigger down steam signaling involved in various diseases or disorders. Binding of MOR8457 to PDGF-AB and PDGF-BB, which blocks binding of PDGF-B to its receptors, could be used to block PDGF-AB and PDGF-BB interaction with their respective receptor complexes, thereby inhibiting the downstream signaling which mediates or is associated with various disease states. Thus, MOR8457 may provide a novel therapeutic for any PDGF-AB and PDGF-BB associated disease. Further, MOR8457 bound with similar characteristics to mouse and rat PDGF-BB, i.e., 10 pM and 25 pM, respectively, making it a useful surrogate antibody for use in preclinical animal model studies thus further increasing its potential usefulness in development of potential therapeutics to treat PDGF-B-mediated signaling diseases or disorders.

Binding Stoichiometry and Epitope Mapping of MOR8457 Binding to PDGF-BB

The data demonstrating that MOR8457 bound to PDGF-AB disclosed elsewhere herein suggested each PDGF-B subunit comprises at least one MOR8457 binding site. This raised the question of whether the two binding sites on a PDGF-BB homodimer interact with two IgV domains from one antibody or from two antibodies, in other words, it was unclear whether the stoichiometry of antibody binding to PDGF-BB is 1:1 or 2:1. In order to address this question, the fact that the same IgV domain but different Fc domains are present on MOR8457-mIgG1 (mouse) and MOR8457-GL-IKR-hIgG1-3m (human) was exploited to perform sequential competition binding assays using Biacore to assess the stoichiometry of MOR8457 binding to PDGF-BB.

TABLE 2

Summary of binding affinities of MOR8457 variants to different PDGFs determined on Biacore

| Analyte | MOR8457-IKR-hIgG1-3m | | | MOR8457-mIgG1 | | | MOR8457-GL-hIgG1-3m | | |
|---|---|---|---|---|---|---|---|---|---|
| | $k_a \times$ $10^7 M^{-1}s^{-1}$ | $k_d \times$ $10^{-4} s^{-1}$ | $K_D$ (pM) | $k_a \times$ $10^7 M^{-1}s^{-1}$ | $k_d \times$ $10^{-4} s^{-1}$ | $K_D$ (pM) | $k_a \times$ $10^7 M^{-1}s^{-1}$ | $k_d \times$ $10^{-4} s^{-1}$ | $K_D$ (pM) |
| huBB | 1.27 | 3.62 | 28 | 1.12 | NA* | <10 | 1.5± (0.4) | 1.9± (0.3) | 13± (3) |
| muBB | 2.95 | 2.93 | 10 | 2.48 | NA* | <10 | 5.3± (1.0) | 2.0± (0.7) | 4± (2) |
| ratBB | 1.77 | 4.47 | 25 | 1.42 | NA* | <10 | 1.7± (0.3) | 2.4± (0.1) | 15± (2) |
| huAB | 0.65 | 4.50 | 69 | 0.59 | NA* | <10 | not tested | not tested | not tested |

All three antibodies demonstrated low pM binding affinity to human PDGF-BB. Germlined variable domains retained tight binding of $K_D$=13 pM±3. Conversion to mouse IgG1 backbone slowed the off rate of MOR8457-mIgG1 antibody binding to all PDGFs, to an extent beyond the limits of kinetics binding on Biacore (indicated in Table 2 as "NA*"). The affinity of this type of binding was estimated to be less than 10 pM (<10) and beyond the limits of the Biacore instrument. The various MOR8457 antibody constructs were specific for PDGF-B demonstrated by the fact that MOR8457 variants only bound PDGF-BB and PDGF-AB (Table 2) but did not bind to PDGF-AA nor PDGF-DD (data not shown). Binding of MOR8457 to PDGF-AB and PDGF-BB, but not PDGF-AA, suggests that each PDGF-B subunit in the dimer has one exposed MOR8457 binding site. Binding affinities to PDGF-AB and PDGF-BB showed a slight difference, 69 pM and 28 pM, which may be due to minor conformational differences of PDGF-B present in the hetero-dimer PDGF-AB and the homo-dimer PDGF-BB.

Figure 3:
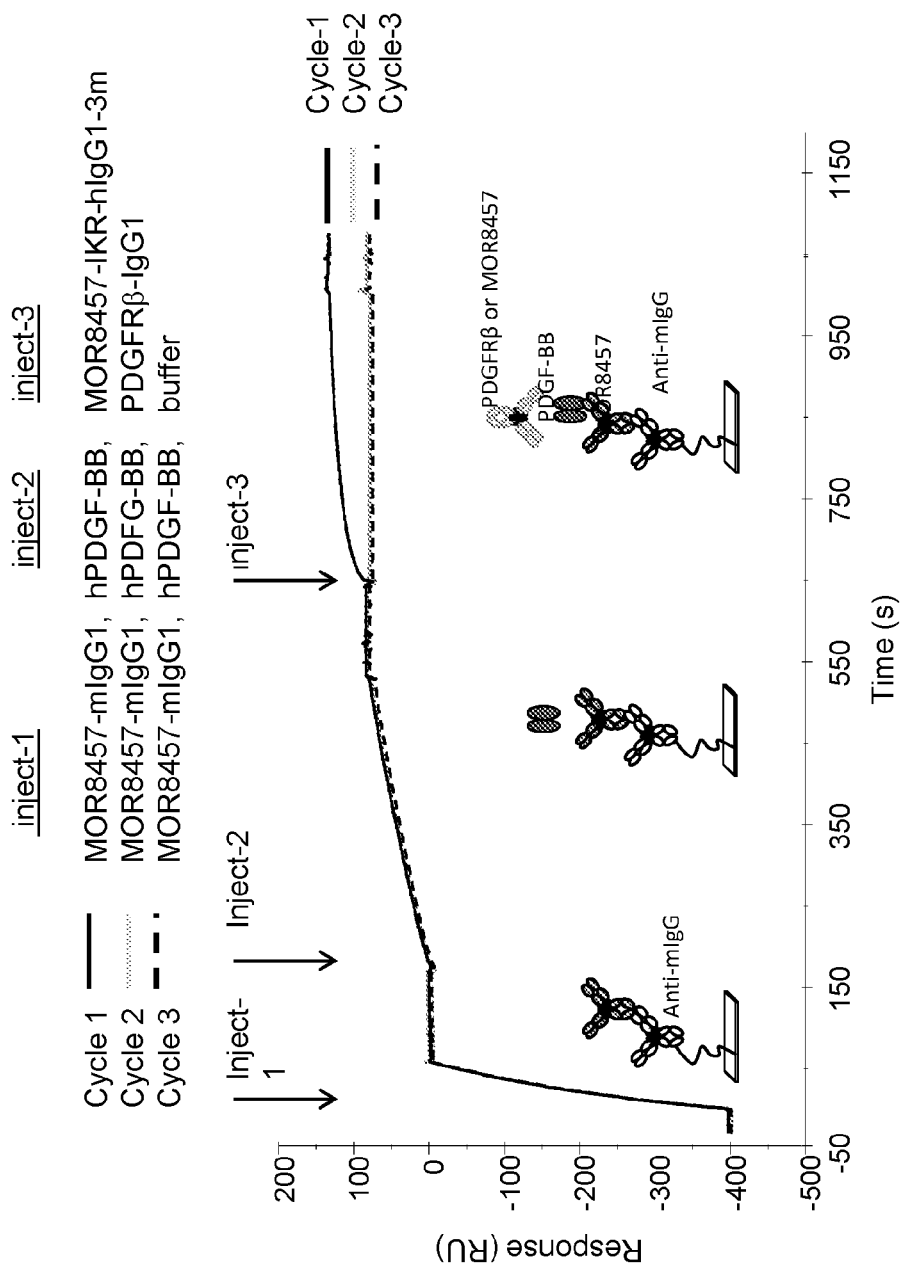
FIG. 3 depicts a sensorgram and a drawing illustrating that MOR8457-IKR-hIgG1-3m but not PDGFRβ-hIgg1 bound human PDGF-BB when it was already bound to MOR8457-mIgG1. MOR8457-mIgG1 was captured via anti-mouse IgG immobilized onto a CM5 sensor chip, resulting in a stable surface of 200-400 RU (inject 1). Human PDGF-BB at 1 nM was injected for 6 minutes to reach the surface saturation (inject 2), followed by injection of MOR8457-IKR-hIgG1-3m (Cycle1, inject-3, black line), or PDGFRβ-hIGg1 (Cycle 2, inject 3, grey line), or buffer (Cycle 3, inject 3, dashed line). In contrast to PDGFRβ-hIgG1 and buffer which did not show binding (Cycle 2 and Cycle 3 lines show no increase in RU after injection 3), MOR8457-IKR-hIgG1-3m bound to pre-assembled MOR8457-mIgG1/PDGF-BB complex on the chip (Cycle 1 sensorgram showed an increase in resonance after injection3), demonstrating that the PDGF-BB dimer bound to two MOR8457 molecules and that binding of PDGF-BB by one MOR8457 was sufficient to block the PDGFRββ receptor binding. Data shown are from one representative experiment of two independent experiments.

In the first sequential competition binding assay, MOR8457-mIgG1 was captured via anti-mouse IgG (GE Healthcare) immobilized onto a CM5 sensor chip, resulting in a stable surface of 200-400 RU. Then, human PDGF-BB at 1 nM was injected for 6 minutes followed by MOR8457-IKR-hIgG1-3m as illustrated in the drawing shown in FIG. 3 and in the sensorgram shown by the solid line after Inject 2. In FIG. 3, the sensorgram data disclosed for Cycle 1 after Inject 3 demonstrate that MOR8457-IKR-hIgG1-3m bound to pre-assembled MOR8457-mIgG/PDGF-BB complex (formed after Inject 2, indicating MOR8457-mIgG bound only to one site on PDGF-BB while the other binding site on PDGF-BB was available for a second antibody, in this case, the second site was available for MOR8457-IKR-hIgG1-3m binding. Therefore, these data demonstrate that the binding stoichiometry of MOR8457 to PDGF-BB is 2:1. This contrasts the 1:1 stoichiometry binding of PDGFRββ homodimer ectodomain to PDGF-BB (Shim et al., 2010, Proc. Natl. Acad. Sci. USA 107:11307-11312). Without wishing to be limited to any particular theory, it may be that the 2:1 stoichiometry binding mode of MOR8457:PDGF-BB makes it possible to form a large molecular weight MOR8457: PDGF-BB complexes by alternatively cross linking between antibody and PDGF-BB, which may potentiate drug clearance and/or stimulate anti-drug antibody responses. Thus, the skilled artisan would appreciate that it may be desirable to reformat MOR8457 antibodies to provide a single arm antibody such that any potential cross-linking of multiple PDGF-BBs and antibodies will be avoided or reduced.

Antibody Inhibition of PDGF-BB Binding to PDGFRβ

As discussed previously elsewhere herein, PDGF-BB signaling is activated after its binding to cell surface PDGF receptor 13 dimers. In order to test whether binding of MOR8457 antibodies to PDGF-BB blocked this binding to the receptor and thereby inhibited downstream signaling, competitive binding analyses were performed between MOR8457 and a PDGFRβ-hIgG1 fusion protein comprising the ectodomain of PDGFRβ and a human wild type IgG1 constant domain to provide a soluble PDGFRβ on Biacore via either sequentially binding on the chip or neutralizing PDGF-BB in solution.

Sequential Binding Analysis on Solid Support (Biacore Chip)

Figure 4:
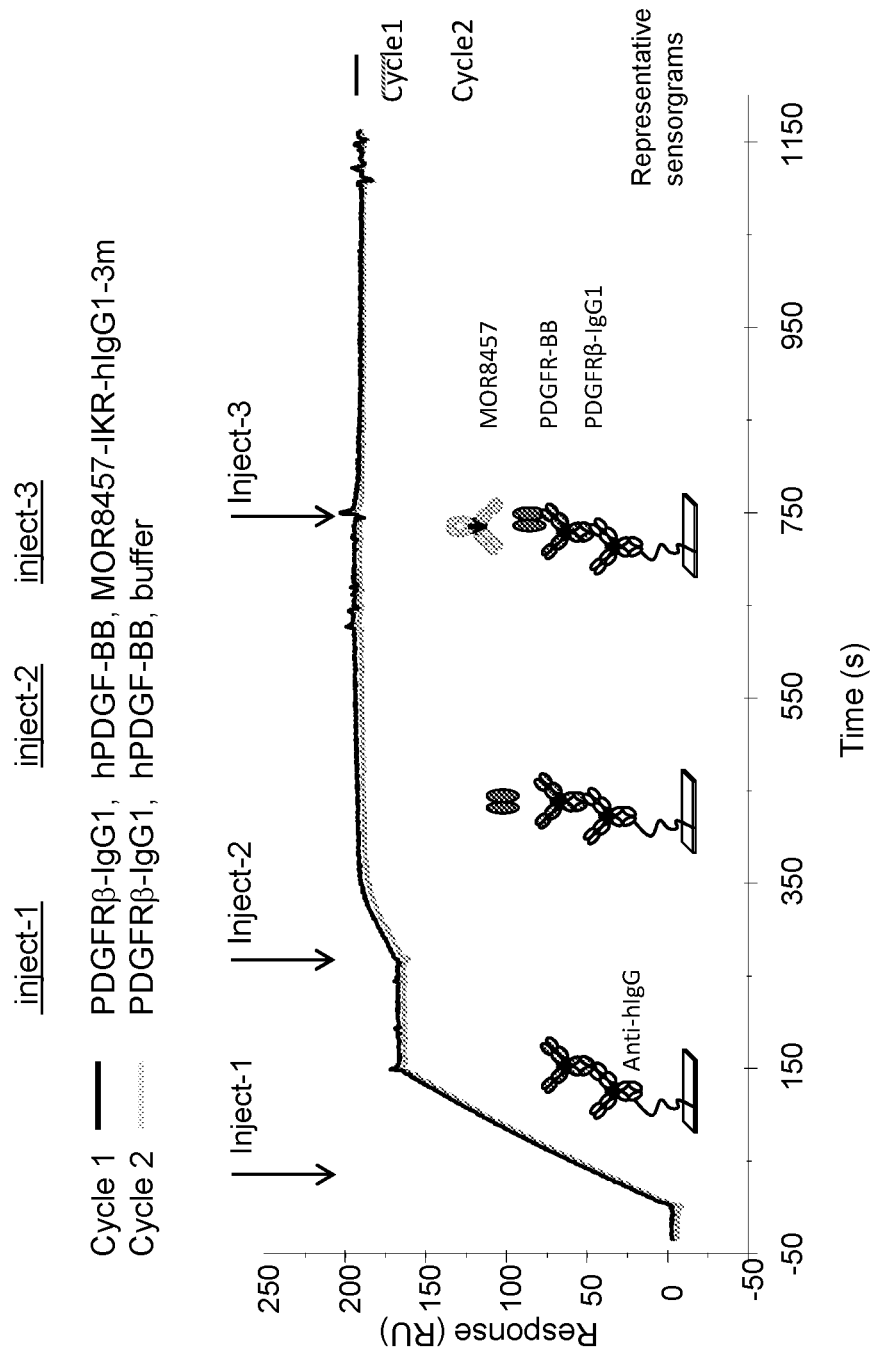
FIG. 4 depicts a sensorgram and a diagram illustrating that MOR8457-IKR-hIgG1-3m could not bind human PDGF-BB when PDGF-BB was bound to hPDGFRβ-hIgG1. PDGFRβ-hIgG1 was captured onto a CM5 sensor chip via an anti-human IgG antibody (inject-1). Human PDGF-BB was then injected at a concentration of 1 nM for 6 minutes to saturate the binding sites on PDGFRβ-hIgG1 (inject-2), followed by injecting MOR8457-IKR-hIgG1-3m (Cycle 1, inject-3, black line), or buffer (Cycle 2, inject-3, grey line). MOR8457-IKR-hIgG1-3m did not bind to pre-assembled PDGFRβ-hIgG1/PDGF-BB complex suggesting that MOR8457 and PDGFR compete for the same binding sites on PDGF-BB. Data shown are from one representative experiment of two independent experiments.

For the sequential binding analysis on the chip, PDGFRβ-hIgG1 was captured onto a CM5 sensor chip via an anti-human IgG antibody as illustrated in the drawing in FIG. 4A). Human PDGF-BB was then injected at a concentration of 1 nM for 6 minutes to saturate the binding sites on PDGFRβ-hIgG1, followed by injecting MOR8457-mIgG1. Binding of PDGFRβ-hIgG1 to PDGF-BB blocked the binding of MOR8457-mIgG1 to PDGF-BB (see sensorgram for Cycle 1 shown in FIG. 4). Conversely, when MOR8457-mIgG1 antibody was captured on the chip first, binding of MOR8457-mIgG1 to PDGF-BB blocked the PDGFRβ-hIgG1 fusion protein binding to PDGF-BB as shown by the Cycle 2 sensorgram depicted in FIG. 3. These results demonstrate that MOR8457 cross-competes for binding with PDGFRβ for PDGF-BB and they further demonstrate that single site occupancy by MOR8457 is sufficient to block the interaction of PDGF-BB with PDGFRβ. These data are consistent with the data provided by the detailed computer modeling disclosed below which shows the binding interaction between MOR8457 and PDGF-BB. Briefly, as more fully discussed below, the detailed epitope mapping revealed by the co-crystal structure of PDGF-BB with MOR8457 Fab confirmed that the interface between PDGF-BB and MOR8457 overlaps with the receptor binding sites. Thus, MOR8457 directly competes with the PDGFRβ receptor for binding with PDGF-BB further supporting the use of MOR8457 as a potential novel therapeutic for treatment of diseases or disorders mediated by PDGF-BB binding to its receptors (PDGFRαβ and PDGFRββ).

Sequential Binding Analysis in Solution

Figure 5:
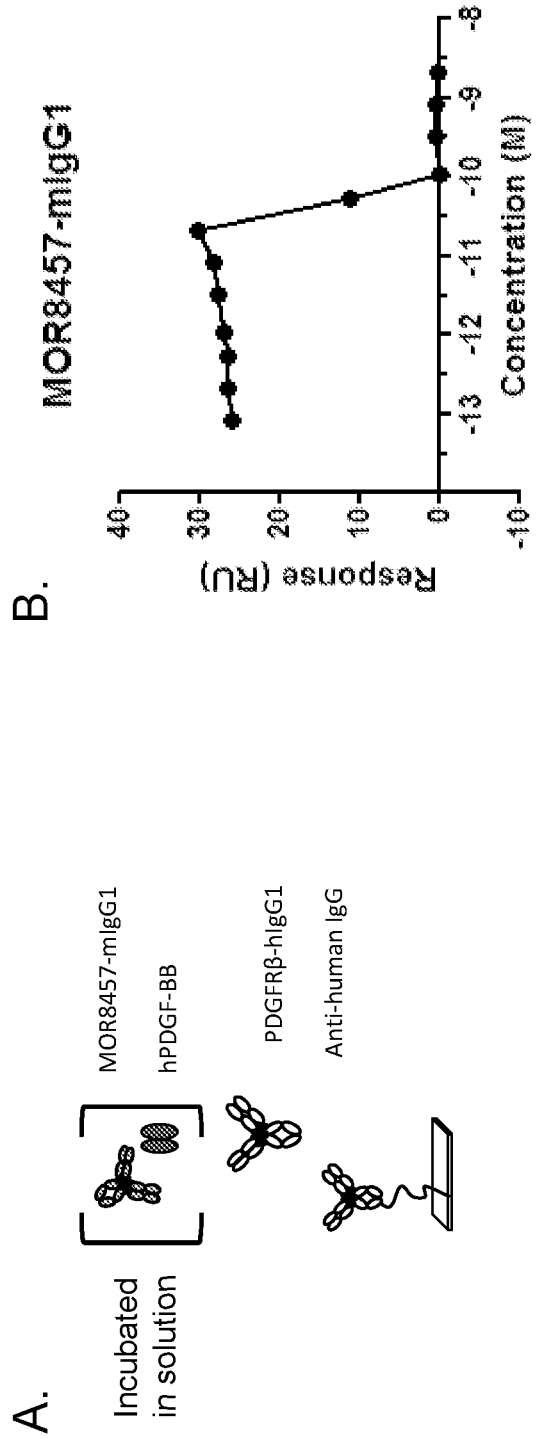
FIG. 5, comprising panels A and B, shows that MOR8457 blocked human PDGF-BB binding to PDGFRβ-hIgG1 in solution.

Because of the complexity of the 2:1 binding stoichiometry, and also to avoid any potential artifacts introduced by sequential binding on the chip, the competitive binding was further confirmed by neutralizing PDGF-BB with MOR8457 in solution as illustrated by the diagram shown in FIG. 5A. MOR8457-mIgG1 was serially diluted in PBS then mixed with 1 mM of human PDGF-BB and incubated for 20 hours at 2-8° C. to reach equilibrium. Each MOR8457-mIgG1 and PDGF-BB dilution mixture shown between [brackets] in FIG. 5A, was then injected over the surface of PDGFRβ-hIgG1 captured by anti-human IgG1 on a CM5 chip. FIG. 5B depicts a graph showing the concentration response curve of MOR8457 inhibition. With increased concentration, MOR8457-mIgG1 completely blocked the binding of PDGF-BB to PDGFRβ-hIgG1 on the chip. All of these data demonstrate a shared binding site between MOR8457 and PDGFRβ onto PDGF-BB. These data further demonstrate that the binding site of MOR8457 for PDGF-BB directly competes with the binding site of the receptor for PDGF-BB and that binding of one MOR8457 on PDGF-BB is sufficient to block the ligand's binding to its receptor. These data further confirm the potential usefulness of MOR8457 as a novel therapeutic to treat diseases or disorders mediated by or associated with PDGF-B binding to its receptors.

Example 7

Crystal Structure of PDGF-BB in Complex with the Neutralizing Antibody Fragment Fab-MOR8457

Structural Insight into the Binding Mode of MOR8457 to PDGF-BB

PDGF-BB in complex with MOR8457-Fab was crystallized at 18° C. from a solution containing 22% PEG 3350 and 0.1M Tris, pH 7.0. The crystals had symmetry consistent with monoclinic space group $P2_1$ with cell parameters a=90.2 Å, b=68.5 Å; c=95.3 Å, β=97.6° and with one protein complex in the asymmetric unit cell. A data set to a 2.3 Å resolution was collected from a single frozen crystal at IMCA beamline 17-ID at the Argonne National Laboratory (APS). The data were processed and scaled using autoPROC and SCALA. The final data set was 99.7% complete with average redundancy of 3.4 and with $R_{sym}$, of 5.8%.

The structure was solved by molecular replacement with PHASER starting with the fab fragment models prepared from the Brookhaven PDB entries: 2adg and 8fab, and with the PDGF-BB model prepared from entry: 3 mjg. The initial solution was obtained by searching for each of the four domains of the Fab molecule separately. This partial solution was used to search for a second copy of the Fab fragment, followed by a final search for the PDGF-BB molecule. The final complete molecular replacement solution contained two MOR8457-Fab fragments bound to one PDGF-BB dimer. Several iterative rounds of model manual adjustment and model rebuilding using COOT followed by crystallographic refinement using autoBUSTER yielded the final refined model of the complex with a crystallographic $R_{work}$ of 21.1% and $R_{free}$ of 24.47%. The final MOR8457-Fab +PDGF-BB model comprises two chains of the first Fab copy, H and L (residues 1H-133H, 142H-191H, 200H-220H of heavy chain H and residues 3L-205L of light chain L), two chains of the second Fab copy, B and A (1B-134B, 141B-220B of heavy chain B and 2A-207A of light chain A) and two chains of PDGF-BB, C and D (10C-101C of chain C and 7D-102D of chain D). Missing amino acids in some regions were not modeled into the structure because of the lack of electron density, very likely due to disorder. Non-protein atoms present in the model include 327 water molecules.

Figure 6:
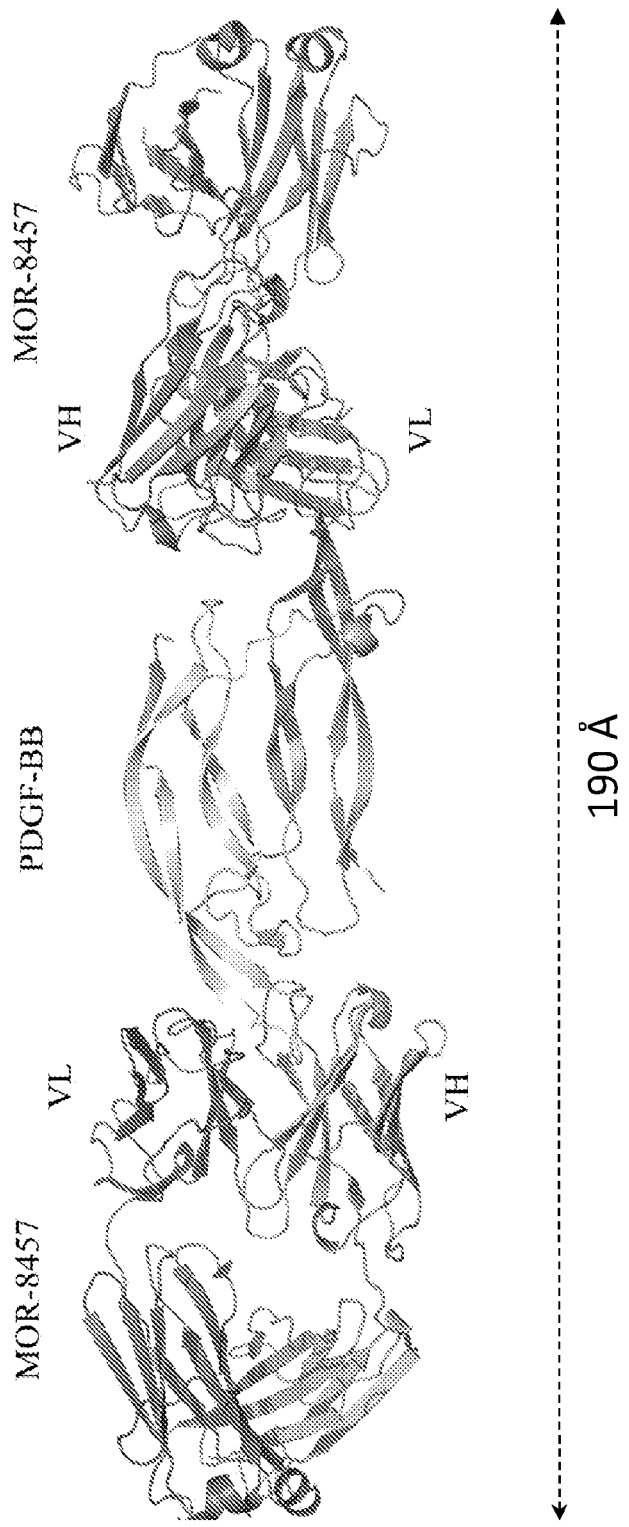
FIG. 6 depicts a diagram illustrating the binding mode of MOR8457 to a PDGF-BB dimer. The drawing illustrates that binding epitopes 1 and 2 on the PDGF-BB molecule are approximately 190 Å apart such that a single MOR8457 antibody cannot bind both epitopes 1 and 2 simultaneously. Thus, the model demonstrates that the 2:1 binding stoichiometry observed elsewhere herein is due to the geometric constraints of the two epitopes being too far apart.

The crystal structure revealed two MOR8457-Fab molecules binding to the two symmetrical sites at the two opposite ends of a single PDGF-BB cytokine as illustrated by the ribbon diagram shown in FIG. 6. The C-termini of the two MOR8457-Fab molecules are separated by about 190 Å, which imposes certain geometric constraints on observed stoichiometry and further confirms the 2:1 binding stoichiometry for MOR8457 and PDGF-BB, with one PDGF-BB molecule cross-linked by two spatially distant MOR8457 antibodies.

The Two Binding Epitopes with Similar Interactions

As noted previously, the crystal structure reveals two MOR8457-Fab molecules binding to the two symmetrical sites at the two opposite ends of a single PDGF-BB cytokine (ribbon diagram in FIG. 6). The C-termini of the two MOR8457-Fab molecules are separated by about 190 Å, which imposes certain geometric constraints on observed stoichiometry.

Figure 7:
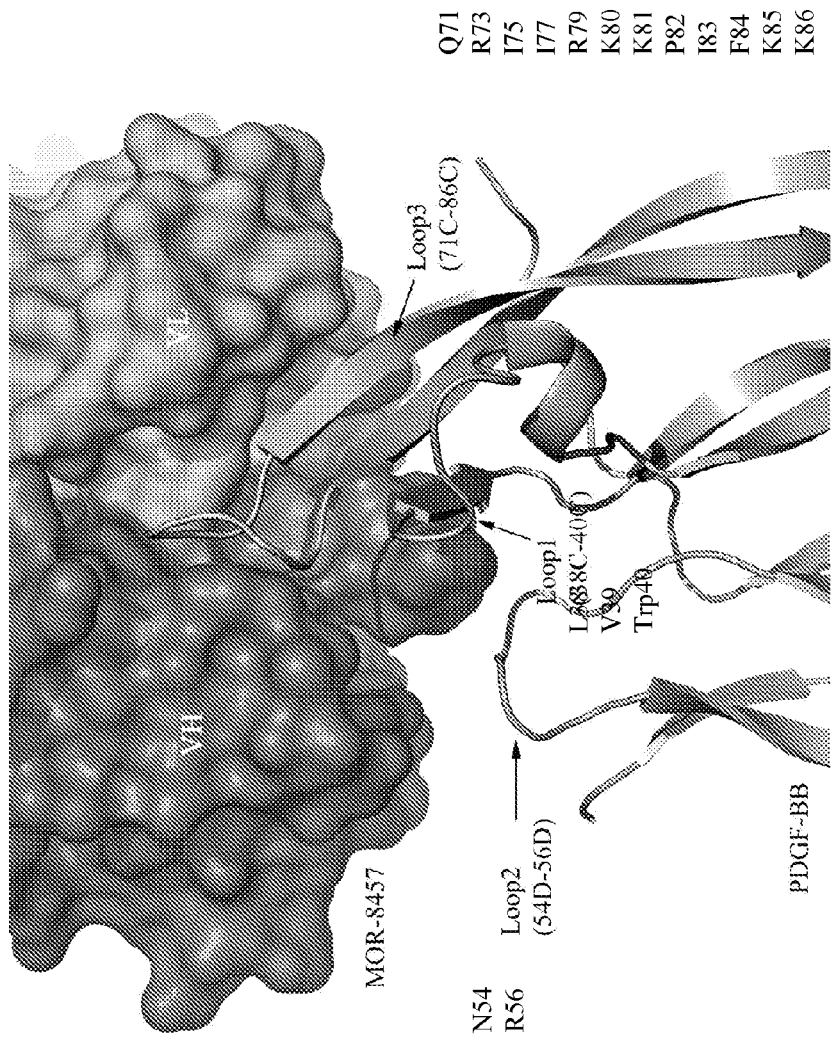
FIG. 7 depicts a diagram of a model showing the binding of one MOR8457 to one binding epitope on one PDGF-B. The diagram further depicts that the VH and VL domains of MOR8457 bind (i.e., contact residues less than 4 Å apart) the following amino acid residues of PDGF-B: Leu 38, Val, 39, Trp 40, Asn 54, Arg 56, Glu 71, Arg 73, Ile 75, Ile 77, Arg 79, Lys 80, Lys 81, Pro 82, Ile 83, Phe 84, Lys 85 and Lys 86.

The observed crystal structure and its comparison with the PDGF-BB/PDGFβ-receptor complex (Shim et al., 2010, Proc. Natl. Acad. Sci. USA 107:11307-11312) further demonstrates that the neutralizing effect of MOR8457 is due to direct competition of the antibody and the PDGFβ-receptor for the same binding determinants on PDGF-BB. As shown by Shim et al., in the case with PDGFβ-receptor, the binding of MOR8457 to each of the opposite ends of PDGF-BB creates two interacting surfaces and hence the two binding epitopes, numbers 1 and 2, on the cytokine surface. As both these binding surfaces involve similar interactions, details displayed in FIG. 7 refer to only one epitope, binding epitope number 1, that involves the antibody chains H and L (represented by the molecular surface shown in FIG. 7) and the cytokine monomers C and D represented by the ribbon diagram in FIG. 7.

At each of the two interfaces, the PDGF-BB residues essential for binding are contributed by both PDGF-B monomers, with 87% of the interactions coming from one monomer (Loop 1 and Loop 3) and the remaining 13% (Loop 2) from the other monomer. A total of 17 residues from PDGF-BB and 22 residues from MOR8457-Fab are involved in interactions at each interface as indicated by the fact that they are less than four angstroms (4 Å) apart and therefore considered "contact residues." All CDR regions, except CDR-H1, are involved in interaction with PDGF-BB, with the largest contribution coming from CDR-H3. Each binding interface results from an interplay of hydrogen-bonding and aromatic ring interactions, with striking complementarily between negatively charged CDRs and positively charged Arg/Lys residues on PDGF-BB. All direct interactions within 4 Å, covering both binding epitopes #1 and #2, are set forth in Table 3 below. Thus, all direct interactions within 4 Å, covering both antibody paratopes and binding epitopes #1 and #2, are listed in Table 3 below.

TABLE 3

| Paratope | | | Binding Epitope number 1 | | | |
|---|---|---|---|---|---|---|
| VH (chain H) atoms | | | PDGF-BB (chain C) Atoms | | | distance |
| Trp | 47H | CZ3 | . . . Lys | 81C | CB | . . . 3.96 |
| Trp | 47H | CH2 | . . . Lys | 81C | CB | . . . 3.75 |
| Tyr | 50H | CD1 | . . . Pro | 82C | CG | . . . 4.00 |
| Leu | 57H | CD1 | . . . Ile | 77C | CG2 | . . . 3.84 |
| | | | . . . Ile | 77C | CD1 | . . . 3.93 |
| Leu | 57H | CD2 | . . . Ile | 77C | CG2 | . . . 3.67 |
| Tyr | 59H | CB | . . . Lys | 80C | O | . . . 3.53 |
| | | | . . . Lys | 81C | CA | . . . 3.95 |
| | | | . . . Pro | 82C | CD | . . . 3.96 |
| Tyr | 59H | CG | . . . Lys | 80C | O | . . . 3.94 |
| | | | . . . Lys | 81C | CA | . . . 3.89 |
| | | | . . . Pro | 82C | CD | . . . 3.51 |
| Tyr | 59H | CD1 | . . . Pro | 82C | CD | . . . 3.47 |
| Tyr | 59H | CD2 | . . . Lys | 80C | C | . . . 3.82 |
| | | | . . . Lys | 80C | O | . . . 3.45 |
| | | | . . . Lys | 81C | CA | . . . 3.56 |

TABLE 3-continued

| | | | | | | |
|---|---|---|---|---|---|---|
| | | | . . . Pro | 82C | CD | . . . 3.91 |
| | | | . . . Arg | 79C | O | . . . 3.53 |
| | | | . . . Lys | 81C | N | . . . 3.87 |
| | | | . . . Lys | 81C | C | . . . 3.92 |
| Tyr | 59H | CE1 | . . . Pro | 82C | CD | . . . 3.85 |
| Tyr | 59H | CE2 | . . . Ile | 77C | O | . . . 3.29 |
| | | | . . . Arg | 79C | O | . . . 3.42 |
| Tyr | 59H | CZ | . . . Ile | 77C | O | . . . 3.62 |
| Tyr | 59H | OH | . . . Ile | 77C | CA | . . . 3.57 |
| | | | . . . Ile | 77C | C | . . . 3.71 |
| | | | . . . Ile | 77C | CB | . . . 3.87 |
| | | | . . . Ile | 77C | CG2 | . . . 3.45 |
| | | | . . . Ile | 77C | O | . . . 3.05 |
| | | | . . . Ile | 77C | CD1 | . . . 3.70 |
| Tyr | 60H | N | . . . Lys | 80C | O | . . . 3.95 |
| Tyr | 60H | O | . . . Lys | 80C | O | . . . 3.71 |
| Asp | 62H | OD1 | . . . Lys | 80C | CD | . . . 3.65 |
| Asp | 62H | OD2 | . . . Lys | 80C | CD | . . . 3.98 |
| Trp | 102H | O | . . . Phe | 84C | CE2 | . . . 3.68 |
| Trp | 102H | CZ2 | . . . Trp | 40C | CE3 | . . . 3.68 |
| Trp | 102H | CZ3 | . . . Leu | 38C | CD1 | . . . 3.65 |
| | | | . . . Leu | 38C | CB | . . . 3.77 |
| | | | . . . Ile | 75C | CD1 | . . . 3.67 |
| Trp | 102H | CH2 | . . . Val | 39C | O | . . . 3.72 |
| | | | . . . Ile | 75C | CD1 | . . . 3.97 |
| Tyr | 103H | O | . . . Phe | 84C | CG | . . . 3.82 |
| | | | . . . Phe | 84C | CD2 | . . . 3.14 |
| | | | . . . Phe | 84C | CE2 | . . . 3.77 |
| | | | . . . Arg | 73C | CD | . . . 3.14 |
| | | | . . . Arg | 73C | NE | . . . 3.80 |
| | | | . . . Arg | 73C | CZ | . . . 3.65 |
| | | | . . . Arg | 73C | NH1 | . . . 2.76 |
| Tyr | 103H | C | . . . Phe | 84C | CD2 | . . . 3.44 |
| | | | . . . Phe | 84C | CE2 | . . . 3.60 |
| | | | . . . Arg | 73C | NH1 | . . . 3.71 |
| Tyr | 103H | CB | . . . Trp | 40C | CB | . . . 3.74 |
| | | | . . . Ile | 75C | CD1 | . . . 3.67 |
| | | | . . . Trp | 40C | CG | . . . 3.95 |
| Tyr | 103H | CG | . . . Trp | 40C | CB | . . . 3.90 |
| | | | . . . Trp | 40C | CG | . . . 3.53 |
| | | | . . . Trp | 40C | CD1 | . . . 3.88 |
| | | | . . . Trp | 40C | CD2 | . . . 3.78 |
| Tyr | 103H | CD1 | . . . Arg | 73C | CD | . . . 3.95 |
| | | | . . . Trp | 40C | CG | . . . 3.61 |
| | | | . . . Trp | 40C | CD1 | . . . 3.45 |
| | | | . . . Trp | 40C | NE1 | . . . 3.74 |
| | | | . . . Arg | 73C | NE | . . . 3.91 |
| | | | . . . Arg | 73C | CZ | . . . 3.97 |
| Tyr | 103H | CD2 | . . . Trp | 40C | CE3 | . . . 3.65 |
| | | | . . . Trp | 40C | CG | . . . 3.79 |
| | | | . . . Trp | 40C | CD2 | . . . 3.51 |
| | | | . . . Trp | 40C | CE2 | . . . 3.94 |
| Tyr | 103H | CE1 | . . . Trp | 40C | CD1 | . . . 3.58 |
| | | | . . . Trp | 40C | NE1 | . . . 3.34 |
| | | | . . . Trp | 40C | CE2 | . . . 3.67 |
| Tyr | 103H | CE2 | . . . Trp | 40C | CE3 | . . . 3.72 |
| | | | . . . Trp | 40C | CZ3 | . . . 3.82 |
| | | | . . . Trp | 40C | CH2 | . . . 3.77 |
| | | | . . . Trp | 40C | CD2 | . . . 3.54 |
| | | | . . . Trp | 40C | CE2 | . . . 3.49 |
| | | | . . . Trp | 40C | CZ2 | . . . 3.62 |
| Tyr | 103H | CZ | . . . Trp | 40C | CD2 | . . . 3.82 |
| | | | . . . Trp | 40C | NE1 | . . . 3.51 |
| | | | . . . Trp | 40C | CE2 | . . . 3.33 |
| | | | . . . Trp | 40C | CZ2 | . . . 3.51 |
| Tyr | 103H | OH | . . . Trp | 40C | NE1 | . . . 3.87 |
| | | | . . . Trp | 40C | CE2 | . . . 3.66 |
| | | | . . . Trp | 40C | CZ2 | . . . 3.39 |
| Gly | 104H | O | . . . Phe | 84C | CZ | . . . 3.77 |
| Gly | 104H | N | . . . Phe | 84C | CD2 | . . . 3.90 |
| | | | . . . Phe | 84C | CE2 | . . . 3.78 |
| Gly | 104H | CA | . . . Arg | 73C | NH1 | . . . 3.79 |
| Gly | 104H | C | . . . Phe | 84C | CE1 | . . . 3.99 |
| | | | . . . Phe | 84C | CZ | . . . 3.85 |
| Gly | 105H | N | . . . Phe | 84C | CD1 | . . . 3.80 |
| | | | . . . Phe | 84C | CE1 | . . . 3.73 |
| Gly | 105H | CA | . . . Phe | 84C | CE1 | . . . 3.68 |

TABLE 3-continued

| VH (chain H) atoms | | | PDGF-BB (chain D) atoms | | | distance |
|---|---|---|---|---|---|---|
| Trp | 102H | CB | ... Arg | 56D | CD | ... 3.80 |
| Trp | 102H | CG | ... Arg | 56D | CG | ... 3.66 |
|  |  |  | ... Arg | 56D | CD | ... 3.73 |
| Trp | 102H | CD1 | ... Arg | 56D | CG | ... 3.62 |
|  |  |  | ... Asn | 54D | O | ... 3.72 |
| Trp | 102H | CD2 | ... Arg | 56D | CG | ... 3.93 |
|  |  |  | ... Arg | 56D | NH1 | ... 3.64 |
| Trp | 102H | NE1 | ... Arg | 56D | CG | ... 3.88 |
|  |  |  | ... Asn | 54D | O | ... 3.07 |
| Trp | 102H | CE3 | ... Arg | 56D | NH1 | ... 3.39 |
| Trp | 102H | CZ3 | ... Arg | 56D | NH1 | ... 3.56 |
| Trp | 102H | CH2 | ... Arg | 56D | NH1 | ... 3.95 |

| VL (chain L) atoms | | | PDGF-BB (chain C) atoms | | | distance |
|---|---|---|---|---|---|---|
| Gly | 28L | C | ... Lys | 86C | NZ | ... 3.82 |
| Gly | 28L | O | ... Lys | 86C | CD | ... 3.39 |
|  |  |  | ... Lys | 86C | CE | ... 3.57 |
|  |  |  | ... Lys | 86C | NZ | ... 2.77 |
| Ser | 29L | C | ... Lys | 86C | N | ... 3.93 |
|  |  |  | ... Lys | 86C | CG | ... 3.97 |
| Ser | 29L | O | ... Lys | 85C | CA | ... 3.55 |
|  |  |  | ... Lys | 85C | CG | ... 3.38 |
|  |  |  | ... Lys | 85C | C | ... 3.67 |
|  |  |  | ... Lys | 86C | N | ... 2.85 |
|  |  |  | ... Lys | 86C | CA | ... 3.76 |
|  |  |  | ... Lys | 86C | CB | ... 3.59 |
|  |  |  | ... Lys | 86C | CG | ... 3.72 |
| Tyr | 30L | C | ... Lys | 86C | CE | ... 3.88 |
| Tyr | 30L | O | ... Lys | 86C | CE | ... 3.36 |
|  |  |  | ... Lys | 86C | NZ | ... 3.16 |
| Tyr | 30L | CD1 | ... Lys | 85C | CA | ... 3.99 |
|  |  |  | ... Phe | 84C | O | ... 3.96 |
| Tyr | 30L | CE1 | ... Ile | 83C | CG2 | ... 3.70 |
|  |  |  | ... Lys | 85C | CG | ... 3.90 |
|  |  |  | ... Lys | 85C | CD | ... 3.74 |
| Tyr | 30L | OH | ... Lys | 85C | CD | ... 3.97 |
| Phe | 31L | N | ... Phe | 84C | O | ... 3.95 |
| Phe | 31L | CD1 | ... Arg | 73C | NH2 | ... 3.76 |
| Phe | 31L | CD2 | ... Phe | 84C | O | ... 3.27 |
|  |  |  | ... Arg | 73C | NH1 | ... 3.90 |
| Phe | 31L | CE1 | ... Arg | 73C | CZ | ... 3.89 |
|  |  |  | ... Arg | 73C | NH2 | ... 3.48 |
|  |  |  | ... Gln | 71C | NE2 | ... 3.76 |
| Phe | 31L | CE2 | ... Arg | 73C | CB | ... 3.69 |
|  |  |  | ... Phe | 84C | O | ... 3.74 |
|  |  |  | ... Arg | 73C | NE | ... 3.78 |
|  |  |  | ... Arg | 73C | CZ | ... 3.74 |
|  |  |  | ... Arg | 73C | NH1 | ... 3.98 |
|  |  |  | ... Lys | 86C | CG | ... 3.78 |
| Phe | 31L | CZ | ... Arg | 73C | CB | ... 3.93 |
|  |  |  | ... Arg | 73C | NE | ... 3.63 |
|  |  |  | ... Arg | 73C | CZ | ... 3.66 |
|  |  |  | ... Arg | 73C | NH2 | ... 3.70 |
|  |  |  | ... Lys | 86C | CG | ... 3.61 |
|  |  |  | ... Gln | 71C | NE2 | ... 3.74 |
| Asp | 49L | CG | ... Arg | 73C | NH2 | ... 3.63 |
| Asp | 49L | OD1 | ... Arg | 73C | NH2 | ... 3.66 |
| Asp | 49L | OD2 | ... Arg | 73C | NH2 | ... 3.35 |
| Asp | 50L | CG | ... Lys | 86C | NZ | ... 3.61 |
| Asp | 50L | OD1 | ... Lys | 86C | NZ | ... 3.80 |
| Asp | 50L | OD2 | ... Lys | 86C | CE | ... 3.28 |
|  |  |  | ... Lys | 86C | NZ | ... 2.74 |
| Asn | 65L | ND2 | ... Lys | 86C | NZ | ... 3.52 |
| Phe | 90L | O | ... Ile | 83C | CA | ... 3.98 |
|  |  |  | ... Phe | 84C | N | ... 3.71 |
| Phe | 90L | CB | ... Pro | 82C | O | ... 3.33 |
|  |  |  | ... Phe | 84C | CD1 | ... 3.71 |
|  |  |  | ... Phe | 84C | CE1 | ... 3.98 |
| Phe | 90L | CG | ... Pro | 82C | O | ... 3.75 |

TABLE 3-continued

| Paratope | | | Binding Epitope number 2 | | | |
|---|---|---|---|---|---|---|
| VH (chain B) atoms | | | PDGF-BB (chain C) atoms | | | distance |
| Trp | 102B | CD1 | ... Asn | 54C | O | ... 3.82 |
| Trp | 102B | NE1 | ... Asn | 54C | C | ... 3.86 |
|  |  |  | ... Asn | 54C | O | ... 2.80 |
| Trp | 102B | CE2 | ... Asn | 54C | O | ... 3.63 |
| Trp | 102B | CZ2 | ... Asn | 54C | O | ... 3.87 |

| VH (chain B) atoms | | | PDGF-BB (chain D) atoms | | | distance |
|---|---|---|---|---|---|---|
| Trp | 47B | CZ3 | ... Lys | 81D | CB | ... 3.88 |
| Trp | 47B | CH2 | ... Lys | 81D | CB | ... 3.72 |
| Leu | 57B | CD1 | ... Ile | 77D | CG2 | ... 3.70 |
| Leu | 57B | CD2 | ... Ile | 77D | CG2 | ... 3.60 |
| Tyr | 59B | CB | ... Lys | 80D | O | ... 3.57 |
|  |  |  | ... Lys | 81D | CA | ... 3.96 |
|  |  |  | ... Pro | 82D | CD | ... 3.85 |
| Tyr | 59B | CG | ... Lys | 81D | CA | ... 3.95 |
|  |  |  | ... Pro | 82D | CD | ... 3.46 |
| Tyr | 59B | CD1 | ... Pro | 82D | CD | ... 3.54 |
| Tyr | 59B | CD2 | ... Arg | 79D | O | ... 3.48 |
|  |  |  | ... Lys | 80D | C | ... 3.87 |
|  |  |  | ... Lys | 80D | O | ... 3.53 |
|  |  |  | ... Lys | 81D | N | ... 3.89 |
|  |  |  | ... Lys | 81D | CA | ... 3.58 |
|  |  |  | ... Lys | 81D | C | ... 3.90 |
|  |  |  | ... Pro | 82D | N | ... 3.96 |
|  |  |  | ... Pro | 82D | CD | ... 3.83 |
| Tyr | 59B | CE1 | ... Pro | 82D | CD | ... 3.98 |
| Tyr | 59B | CE2 | ... Ile | 77D | O | ... 3.12 |
|  |  |  | ... Arg | 79D | O | ... 3.41 |
| Tyr | 59B | CZ | ... Ile | 77D | O | ... 3.46 |
| Tyr | 59B | OH | ... Ile | 77D | O | ... 2.93 |
|  |  |  | ... Ile | 77D | CG2 | ... 3.20 |
|  |  |  | ... Ile | 77D | CA | ... 3.46 |
|  |  |  | ... Ile | 77D | C | ... 3.58 |
|  |  |  | ... Ile | 77D | CB | ... 3.67 |
|  |  |  | ... Ile | 77D | CD1 | ... 3.61 |
| Tyr | 60B | N | ... Lys | 80D | O | ... 3.84 |
| Tyr | 60B | O | ... Lys | 80D | O | ... 3.63 |
| Asp | 62B | OD1 | ... Lys | 80D | CD | ... 3.60 |
| Lys | 65B | NZ | ... Lys | 80D | CG | ... 3.72 |
| Trp | 102B | O | ... Phe | 84D | CE2 | ... 3.83 |
| Trp | 102B | CZ2 | ... Trp | 40D | CE3 | ... 3.67 |
| Trp | 102B | CZ3 | ... Ile | 75D | CD1 | ... 3.89 |
| Tyr | 103B | O | ... Phe | 84D | CG | ... 3.87 |
|  |  |  | ... Phe | 84D | CD2 | ... 3.16 |
|  |  |  | ... Arg | 73D | CD | ... 3.26 |
|  |  |  | ... Arg | 73D | NE | ... 3.84 |
|  |  |  | ... Arg | 73D | CZ | ... 3.67 |
|  |  |  | ... Arg | 73D | NH1 | ... 2.80 |
|  |  |  | ... Phe | 84D | CE2 | ... 3.73 |
| Tyr | 103B | C | ... Phe | 84D | CD2 | ... 3.52 |
|  |  |  | ... Arg | 73D | NH1 | ... 3.76 |
|  |  |  | ... Phe | 84D | CE2 | ... 3.62 |
| Tyr | 103B | CB | ... Trp | 40D | CB | ... 3.96 |
|  |  |  | ... Ile | 75D | CD1 | ... 3.83 |
| Tyr | 103B | CG | ... Trp | 40D | CG | ... 3.79 |
| Tyr | 103B | CD1 | ... Arg | 73D | CD | ... 3.98 |
|  |  |  | ... Arg | 73D | NE | ... 3.81 |
|  |  |  | ... Arg | 73D | CZ | ... 3.85 |
|  |  |  | ... Trp | 40D | CG | ... 3.90 |
|  |  |  | ... Trp | 40D | CD1 | ... 3.71 |
| Tyr | 103B | CD2 | ... Trp | 40D | CE3 | ... 3.99 |
|  |  |  | ... Trp | 40D | CD2 | ... 3.81 |
| Tyr | 103B | CE1 | ... Trp | 40D | CD1 | ... 3.86 |
|  |  |  | ... Trp | 40D | NE1 | ... 3.67 |
| Tyr | 103B | CE2 | ... Trp | 40D | CD2 | ... 3.90 |
|  |  |  | ... Trp | 40D | CE2 | ... 3.80 |
|  |  |  | ... Trp | 40D | CZ2 | ... 3.93 |
| Tyr | 103B | CZ | ... Trp | 40D | NE1 | ... 3.80 |
|  |  |  | ... Trp | 40D | CE2 | ... 3.73 |
|  |  |  | ... Trp | 40D | CZ2 | ... 3.92 |
| Tyr | 103B | OH | ... Trp | 40D | CZ2 | ... 3.89 |
| Gly | 104B | O | ... Phe | 84D | CZ | ... 3.87 |
| Gly | 104B | N | ... Phe | 84D | CE2 | ... 3.82 |

TABLE 3-continued

| | | | | | | |
|---|---|---|---|---|---|---|
| Gly | 104B | CA | ... Arg | 73D | NH1 | ... 3.90 |
| Gly | 104B | C | ... Phe | 84D | CZ | ... 3.88 |
| Gly | 105B | N | ... Phe | 84D | CD1 | ... 3.87 |
| | | | ... Phe | 84D | CE1 | ... 3.75 |
| Gly | 105B | CA | ... Phe | 84D | CE1 | ... 3.70 |

| VL (chain A) atoms | | | PDGF-BB (chain D) atoms | | | distance |
|---|---|---|---|---|---|---|
| Gly | 28A | C | ... Lys | 86D | NZ | ... 3.88 |
| Gly | 28A | O | ... Lys | 86D | CD | ... 3.48 |
| | | | ... Lys | 86D | CE | ... 3.62 |
| | | | ... Lys | 86D | NZ | ... 2.81 |
| Ser | 29A | C | ... Lys | 86D | N | ... 3.93 |
| Ser | 29A | O | ... Lys | 85D | CA | ... 3.50 |
| | | | ... Lys | 85D | C | ... 3.66 |
| | | | ... Lys | 85D | CB | ... 3.95 |
| | | | ... Lys | 85D | CG | ... 3.33 |
| | | | ... Lys | 86D | N | ... 2.89 |
| | | | ... Lys | 86D | CA | ... 3.84 |
| | | | ... Lys | 86D | CB | ... 3.73 |
| | | | ... Lys | 86D | CG | ... 3.91 |
| Ser | 29A | CB | ... Lys | 85D | NZ | ... 3.97 |
| Ser | 29A | OG | ... Lys | 85D | NZ | ... 3.76 |
| Tyr | 30A | CA | ... Phe | 84D | O | ... 3.95 |
| Tyr | 30A | O | ... Lys | 86D | CE | ... 3.54 |
| | | | ... Lys | 86D | NZ | ... 3.32 |
| Tyr | 30A | CD1 | ... Phe | 84D | O | ... 3.98 |
| Tyr | 30A | CE1 | ... Lys | 85D | CD | ... 3.73 |
| | | | ... Lys | 85D | CG | ... 3.97 |
| | | | ... Ile | 83D | CG2 | ... 3.71 |
| Phe | 31A | N | ... Phe | 84D | O | ... 3.84 |
| Phe | 31A | CD2 | ... Phe | 84D | C | ... 3.97 |
| | | | ... Phe | 84D | O | ... 3.18 |
| Phe | 31A | CE1 | ... Gln | 71D | NE2 | ... 3.85 |
| | | | ... Lys | 86D | CG | ... 3.97 |
| | | | ... Arg | 73D | NH2 | ... 3.83 |
| Phe | 31A | CE2 | ... Lys | 86D | CG | ... 3.84 |
| | | | ... Phe | 84D | O | ... 3.67 |
| | | | ... Arg | 73D | CB | ... 3.70 |
| | | | ... Arg | 73D | CZ | ... 3.99 |
| Phe | 31A | CZ | ... Gln | 71D | NE2 | ... 3.84 |
| | | | ... Lys | 86D | CG | ... 3.62 |
| | | | ... Arg | 73D | CB | ... 3.87 |
| | | | ... Arg | 73D | NE | ... 3.86 |
| | | | ... Arg | 73D | CZ | ... 3.84 |
| Asp | 49A | CG | ... Arg | 73D | NH2 | ... 3.81 |
| Asp | 49A | OD1 | ... Arg | 73D | NH2 | ... 3.92 |
| Asp | 49A | OD2 | ... Arg | 73D | NH2 | ... 3.39 |
| Asp | 50A | CG | ... Lys | 86D | NZ | ... 3.63 |
| Asp | 50A | OD1 | ... Lys | 86D | NZ | ... 3.88 |
| Asp | 50A | OD2 | ... Lys | 86D | CE | ... 3.23 |
| | | | ... Lys | 86D | NZ | ... 2.72 |
| Asn | 65A | ND2 | ... Lys | 86D | NZ | ... 3.61 |
| Phe | 90A | O | ... Ile | 83D | CA | ... 3.88 |
| | | | ... Ile | 83D | CG2 | ... 3.92 |
| | | | ... Phe | 84D | N | ... 3.60 |
| Phe | 90A | CB | ... Pro | 82D | O | ... 3.29 |
| | | | ... Phe | 84D | CD1 | ... 3.68 |
| | | | ... Phe | 84D | CE1 | ... 3.94 |
| Phe | 90A | CG | ... Pro | 82D | O | ... 3.69 |
| | | | ... Phe | 84D | CE1 | ... 3.90 |
| Phe | 90A | CD1 | ... Pro | 82D | O | ... 3.35 |
| | | | ... Pro | 82D | CG | ... 3.90 |
| Phe | 90A | CD2 | ... Phe | 84D | CE1 | ... 3.97 |
| Phe | 90A | CE1 | ... Pro | 82D | CG | ... 3.95 |
| Thr | 91A | O | ... Ile | 83D | CG1 | ... 3.36 |
| | | | ... Ile | 83D | CD1 | ... 3.57 |
| | | | ... Lys | 81D | CE | ... 3.41 |
| Thr | 91A | C | ... Ile | 83D | CG1 | ... 3.88 |
| His | 92A | CG | ... Ile | 83D | CD1 | ... 3.87 |
| His | 92A | ND1 | ... Ile | 83D | CD1 | ... 3.93 |
| His | 92A | CD2 | ... Ile | 83D | CD1 | ... 3.79 |
| His | 92A | CE1 | ... Glu | 76D | OE1 | ... 3.80 |
| | | | ... Ile | 83D | CD1 | ... 3.86 |
| His | 92A | NE2 | ... Glu | 76D | OE2 | ... 3.93 |
| | | | ... Ile | 83D | CD1 | ... 3.79 |
| Asn | 93A | O | ... Lys | 81D | CE | ... 3.24 |
| | | | ... Lys | 81D | NZ | ... 2.63 |
| Asn | 93A | C | ... Lys | 81D | NZ | ... 3.65 |
| Ser | 94A | O | ... Lys | 81D | NZ | ... 3.08 |
| Ser | 94A | CA | ... Lys | 81D | NZ | ... 3.58 |
| Ser | 94A | C | ... Lys | 81D | NZ | ... 3.24 |
| Asp | 95A | N | ... Lys | 81D | NZ | ... 3.86 |
| Val | 96A | CG2 | ... Lys | 81D | NZ | ... 3.47 |
| | | | ... Phe | 84C | CE1 | ... 3.93 |
| Phe | 90L | CD1 | ... Pro | 82C | O | ... 3.42 |
| Thr | 91L | O | ... Lys | 81C | NZ | ... 3.60 |
| | | | ... Ile | 83C | CG1 | ... 3.34 |
| | | | ... Lys | 81C | CE | ... 3.40 |
| | | | ... Ile | 83C | CD1 | ... 3.48 |
| Thr | 91L | C | ... Ile | 83C | CG1 | ... 3.85 |
| | | | ... Ile | 83C | CD1 | ... 3.91 |
| His | 92L | O | ... Lys | 81C | NZ | ... 3.94 |
| His | 92L | CA | ... Ile | 83C | CD1 | ... 3.93 |
| Asn | 93L | O | ... Lys | 81C | NZ | ... 3.28 |
| | | | ... Lys | 81C | CE | ... 2.96 |
| Asn | 93L | C | ... Lys | 81C | NZ | ... 3.88 |
| | | | ... Lys | 81C | CE | ... 3.93 |
| Ser | 94L | O | Lys | 81C | CE | ... 3.99 |

To summarize the results shown in Table 3, the following are the contact residues on the antibody (paratope):

For the MOR8457 heavy chain HC: Trp 47, Tyr 50, Leu 57, Tyr 59, Tyr 60 and Asp 62 from CDR-H2; Trp 102, Tyr 103, Gly 104 and Gly 105 from CDR-H3 and light chain L: Gly 28, Ser 29, Tyr 30 and Phe 31 from CDR-L1; Asp 49, Asp 50 and Asn 65 from CDR-L2; Phe 90, Thr 91, His 92, Asn 93 and Ser 94 from CDR-L3.

The contact residues on PDGF-B (epitope) are as follows for epitope number 1:

Chain C: Leu 38, Val, 39 and Trp 40 from loop 1; Glu 71, Arg 73, Ile 75, Ile 77, Arg 79, Lys 80, Lys 81, Pro 82, Ile 83, Phe 84, Lys 85 and Lys 86 from Loop 3; and Chain D: Asn 54 and Arg 56 from loop 2 all with respect to the sequence of SEQ ID NO:33 (NCBI Ref. Seq. NP_002599.1).

The amino acid residues on MOR8457 and their respective contact (less than 4 Å apart) residues on PDGF-BB are provided in Table 4 (epitope 1) and Table 5 (epitope 2) below.

TABLE 4

Direct residue contacts within 4 Å for Epitope 1

| | MOR-8457 | | PDGF-BB |
|---|---|---|---|
| CDR-H2 | TRP 47 | LYS 81 | MONOMER C |
| | TYR 50 | PRO 82 | |
| | LEU 57 | ILE 77 | |
| | TYR 59 | ILE 77 | |
| | | ARG 79 | |
| | | LYS 80 | |
| | | LYS 81 | |
| | | PRO 82 | |
| | TYR 60 | LYS 80 | |
| | ASP 62 | LYS 80 | |
| CDR-H3 | TRP 102 | LEU 38 | MONOMER C |
| | | VAL 39 | |
| | | TRP 40 | |
| | | ILE 75 | |
| | | PHE 84 | |
| | | ASN 54 | MONOMER D |
| | | ARG 56 | |
| | TYR 103 | TRP 40 | MONOMER C |
| | | ARG 73 | |
| | | ILE 75 | |
| | | PHE 84 | |
| | GLY 104 | ARG 73 | |
| | | PHE 84 | |
| | GLY 105 | PHE 84 | |
| CDR-L1 | GLY 28 | LYS 86 | MONOMER C |
| | SER 29 | LYS 85 | |
| | | LYS 86 | |

TABLE 4-continued

Direct residue contacts within 4 Å for Epitope 1

| MOR-8457 | | PDGF-BB |
|---|---|---|
| | TYR 30 | ILE 83 |
| | | PHE 84 |
| | | LYS 85 |
| | | LYS 86 |
| | PHE 31 | GLN 71 |
| | | ARG 73 |
| | | PHE 84 |
| | | LYS 86 |
| CDR-L2 | ASP 49 | ARG 73 |
| | ASP 50 | LYS 86 |
| | ASN 65 | LYS 86 |
| CDR-L3 | PHE 90 | PRO 82 |
| | | ILE 83 |
| | | PHE 84 |
| | THR 91 | LYS 81 |
| | | ILE 83 |
| | HIS 92 | LYS 81 |
| | | ILE 83 |
| | ASN 93 | LYS 81 |
| | SER 94 | LYS 81 |

TABLE 5

Direct residue contacts within 4 Å for Epitope 2

| MOR-8457 | | PDGF-BB | |
|---|---|---|---|
| CDR-H2 | TRP 47 | LYS 81 | MONOMER D |
| | LEU 57 | ILE 77 | |
| | TYR 59 | ILE 77 | |
| | | ARG 79 | |
| | | LYS 80 | |
| | | LYS 81 | |
| | | PRO 82 | |
| | TYR 60 | LYS 80 | |
| | ASP 62 | LYS 80 | |
| | LYS 65 | LYS 80 | |
| CDR-H3 | TRP 102 | TRP 40 | MONOMER D |
| | | ILE 75 | |
| | | PHE 84 | |
| | | ASN 54 | MONOMER C |
| | TYR 103 | TRP 40 | MONOMER D |
| | | ARG 73 | |
| | | ILE 75 | |
| | | PHE 84 | |
| | GLY 104 | ARG 73 | |
| | | PHE 84 | |
| | GLY 105 | PHE 84 | |
| CDR-L1 | GLY 28 | LYS 86 | MONOMER D |
| | SER 29 | LYS 85 | |
| | | LYS 86 | |
| | TYR 30 | ILE 83 | |
| | | PHE 84 | |
| | | LYS 85 | |
| | | LYS 86 | |
| | PHE 31 | GLN 71 | |
| | | ARG 73 | |
| | | PHE 84 | |
| | | LYS 86 | |
| CDR-L2 | ASP 49 | ARG 73 | |
| | ASP 50 | LYS 86 | |
| | ASN 65 | LYS 86 | |
| CDR-L3 | PHE 90 | PRO 82 | |
| | | ILE 83 | |
| | | PHE 84 | |
| | THR 91 | LYS 81 | |
| | | ILE 83 | |
| | HIS 92 | GLU 76 | |
| | | ILE 83 | |
| | ASN 93 | LYS 81 | |
| | SER 94 | LYS 81 | |

TABLE 5-continued

Direct residue contacts within 4 Å for Epitope 2

| MOR-8457 | | PDGF-BB |
|---|---|---|
| | ASP 95 | LYS 81 |
| | VAL 96 | LYS 81 |

The data disclosed herein demonstrate that the two epitopes bound by MOR8457 on the PDGF-BB dimer are extremely similar but not identical.

Without wishing to be bound by any particular theory, based on the relatively small (approximately three-fold) reduction in binding observed by Biacore between MOR8457 binding to PDGF-BB ($K_D$=28 pM) compared with binding to PDGF-AB ($K_D$=69 pM), it may be that the binding mode of MOR8457 to PDGF-AB is essentially that observed in the crystal structure for biding of MOR8457 to PDGF-BB, providing that the PDGF-AB association into the heterodimer is mostly the same as the association of both B subunits of the PDGF-BB homodimer. If the association of the subunits into the AB and BB dimers is essentially the same, then the only difference in direct contacts within 4 Å is in monomer D (for epitope 1) in which there is a substitution of Arg 56 in PDGF-B to Ser 50 in PDGF-A. This single substitution may account for the slight reduction in binding observed by Biacore between MOR8457 binding to PDGF-BB ($K_D$=28 pM) compared with binding to PDGF-AB ($K_D$=69 pM).

Example 8

Inhibition of Human Mesangial Cell Proliferation

Accumulated evidence in the art supports a central role of PDGF-B and/or -D mediated PDGFR-β activation in mesangial cell proliferation and glomerular matrix expansion during the progress of mesangioproliferative diseases such as IgA nephritis. Furthermore, reduction of mesangial cell proliferation and matrix accumulation by specific intervention of PDGFR-β signaling had been demonstrated in rodent models in multiple studies (Ostendorf et al., 2012, Pediatric Nephrol. 27:1041-1050). Because, as more fully set forth previously herein (see, e.g., FIG. 3, Cycle 2 sensorgram, and FIG. 5B), MOR8457 binding to PDGF-BB blocked binding of the ligand to PDGFRβ, the ability of MOR8457-IKR-IgG1-3 mM to functionally inhibit PDGF-BB induced mesangial proliferation in primary human mesangial cells was assessed.

Primary human mesangial cells (ScienCell Research, Carlsbad, Calif.) were cultured and seeded at 15,000 cells/well in black solid-bottom 96-well plates (Cat#353376, BD Biosciences, Franklin Lakes, N.J.). The cells were washed and growth-arrested for 24 hours with serum-free MCM media (ScienCell Research, Carlsbad, Calif.). After 24 hours, the cells were stimulated with serially diluted PDGF-BB (R&D Systems, Minneapolis, Minn.) for 4 hours at 37° C. DNA synthesis was determined during the last 16 hours using a 5-bromo-2'-deoxyuridine (BrdU) incorporation assay according to the manufacturer's instructions (Roche, Mannheim, Germany). The following day, the cells were fixed and assayed for BrdU incorporation according to the manufacturer's protocol.

FIG. 8A depicts a graph showing the concentration response curve showing the dose-dependent increase in mesangial cell proliferation induced by increasing concentrations of PDGF-BB in the absence of MOR8457. PDGF- BB robustly stimulated human mesangial cells proliferation with EC50=2.3 ng/mL (100 pM). Then, the inhibition of cell proliferation by MOR8457-IKR-hIgG1-3m was determined. MOR8457-IKR-hIgG1-3m was half-log diluted from 100 nM down to 0.1 nM then mixed with 2.5 ng/ml of PDGF-BB in serum-free MCM media with 0.1% BSA for 30 minutes before adding to the cells. FIG. 8B shows a representative dose-dependent curve showing inhibition of mesangial cell proliferation with increasing concentrations of MOR8457-IKR-hIgG1-3m. The average IC50 was determined from three independent experiments and is 13.4±2.8 pM and the maximum inhibition is 87.9±5.7%, demonstrating that MOR8457- is a functionally potent inhibitor of PDGF-B/PDGF-β mediated human mesangial proliferation.

The data disclosed previously herein demonstrated competitive inhibition between MOR8457-IKR-hIgG1-3m and PDGFR-β fusion protein for binding of PDGF-BB using Biacore (see, e.g., FIG. 4, Cycle 1 sensorgram). To determine whether the competitive inhibition on the binding interaction observed using Biacore translated to competitive inhibition in the human mesangial cell proliferation functional assay, a Schild analysis (Arunklakshana & Schild, 1959, Br. J. Pharmacol. 65:48-58) was performed. More specifically, a constant amount of antibody was mixed with a series of diluted PDGF-BB before adding to the cells. The EC50 of PDGF-BB measured in the absence and presence of antibodies was used to calculate the dose ratio (DR). A series of log (DR-1) values for a series of log [B] antibody concentrations were plotted on a graph and the pA2 is deduced from the graph, referring to as the concentration of the antibody that causes two-fold shift of the PDGF-BB concentration response curve. The value of pA2 is system independent and reflects the intrinsic affinity of the antibody in the functional cell assay.

Figure 9:
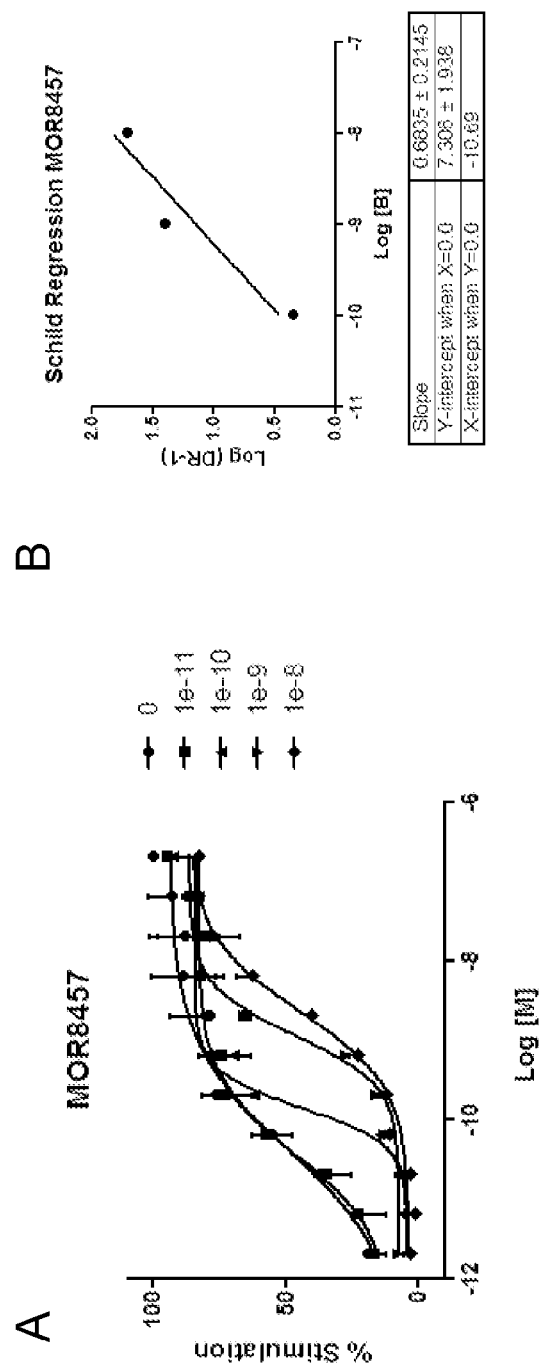
FIG. 9, comprising panels A and B, depicts two graphs showing a Schild analysis for competitive inhibition of MOR8457.

As shown in FIG. 9A, the concentration response curve of PDGF-BB shifted to the right with the increased concentration of MOR8457-IKR-hIgG1-3m and the extent of the inhibition was surmountable (FIG. 9A). The deduced pA2 was about 20 pM which was in the same range as determined by Biacore (13 pM, Table 2). Because the 2:1 binding mode of MOR8457-IKR-hIgG1-3m to PDGF-BB, the right shift of the concentration response curves did not appear parallel as expected seen with a simple 1:1 competitive inhibitor. This was also reflected in a <1 slope of the Schild plot shown on FIG. 9B. Nevertheless, the right shift of the curve, the surmountable inhibition and the low pM pA2 value confirmed that MOR8457-IKR-hIgG1-3m is a potent and competitive PDGF-BB inhibitor of human mesangial cells proliferation.

Mesangial cell proliferation is well-known to play a central role in mesangioproliferative diseases such as IgA nephropathy. Several lines of evidence indicate that increased PDGF-BB expression was associated with IgA nephropathy and blockade of PDGF-BB expression or signaling reduced disease severity. Thus, it would be appreciated by one skilled in the art armed with the disclosure provided herein, that MOR8457, which is a potent competitive inhibitor of PDGF-BB that functionally inhibits mesangial cell proliferation would be a novel potential therapeutic for treatment of mesangioproliferative diseases associated with increased levels of PDGF-BB and/or PDGF-B mediated signaling.

Example 9

Assessment of MOR8457-mIgG1 in an Acute Thy1.1 Rat Model

Figure 10:
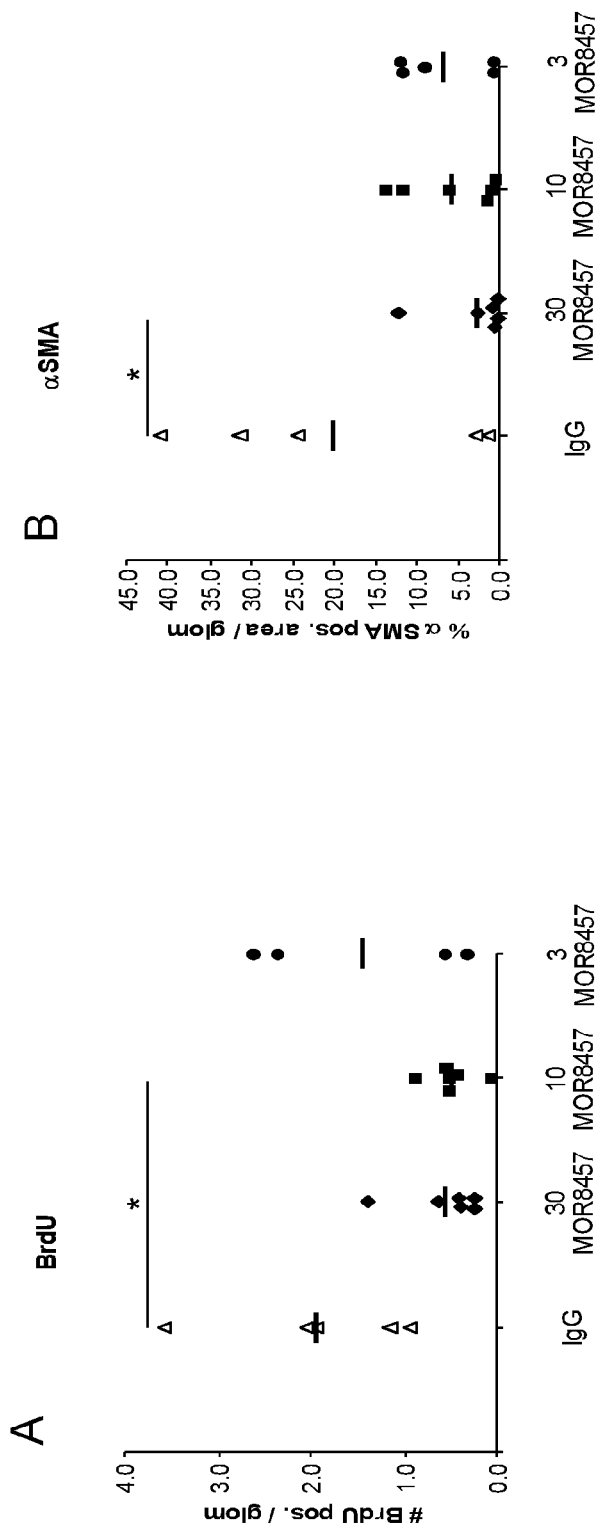
FIG. 10, comprising panels A and B, depict graphs demonstrating the effect of MOR8457-mIgG1 on mesangial cell proliferation on anti-Thy1.1 nephritis kidney tissue samples day 9 post OX-7 induction in rats. Nephritis was initiated in male Wistar rats by i.v. injection of monoclonal antibody OX-7 (1 mg/kg). MOR8457-mIgG1 (3, 10 and 30 mg/kg) and isotype control IgG (30 mg/kg) were administered sub-cutaneously to separate cohorts of animals (n=6) on day 1.5 after disease induction. On day 8, all rats were given an intraperitoneal injection of 50 mg/kg bromodeoxyuridine (BrdU) in order to label cells in the DNA (S) phase of the cell cycle. Animals were sacrificed on day 9 and kidney tissue samples were obtained to assess the effects of MOR8457-mIgG1 on cell proliferation (FIG. 10A) and mesangial and podocyte activation (immunohistochemistry for alpha-smooth muscle actin (α-SMA), FIG. 10B). The data show that MOR8457-mIgG1 induced a dose-dependent decrease in mesangial cell proliferation (FIG. 10A) and reduced alpha-smooth muscle actin positive staining (FIG. 10B).

An in vivo assessment of MOR8457-mIgG1 for effects on mesangial cell proliferation compared with a control IgG was conducted in an anti-Thy1.1 art-recognized rat model of nephritis according to published methods (Boor et al., 2007, Nephrol. Dial. Transplant. 22:1323-1331). Briefly, nephritis was initiated in 150-200 g male Wistar rats by i.v. bolus injection of monoclonal anti-Thy 1.1 antibody OX-7 (1 mg/kg). MOR8457-mIgG1 (3, 10 and 30 mg/kg) and isotype control IgG (30 mg/kg) were administered sub-cutaneously to separate cohorts of animals (n=6) on day 1.5 after disease induction. On day 8, all rats were given an intraperitoneal injection of 50 mg/kg bromodeoxyuridine (BrdU) in order to label cells in the DNA (S) phase of the cell cycle. The animals were sacrificed on day 9 and serum and kidney tissue samples were obtained to confirm mAb exposure and, by histology/immunohistochemical techniques, to assess the effects of MOR8457-mIgG1 on cell proliferation (as determined by quantitation of mitotic figures) and mesangial and podocyte activation (as assessed by immunohistochemistry for alpha-smooth muscle actin (α-SMA), desmin). MOR8457-mIgG1 induced a dose dependent decrease in mesangial cell proliferation, determined by accumulation of BrdU as shown in FIG. 10A. Further, MOR8457-mIgG1 induced a dose dependent decrease in mesangial cell proliferation as shown by the decrease in alpha-smooth muscle actin positive staining (FIG. 10B). These data further suggest that MOR8457 is a potential novel therapeutic for treatment of disease mediated by or associated with, PDGF-BB-PDGFRβ interaction and/or downstream signaling.

Example 10

Reduction of Viscosity MOR8457 Antibodies Via Engineering

The viscosity of monoclonal antibodies at high concentrations is determined by a number of factors including charge, shape, volume and specific self-interactions (Yadav et al., 2010, J. Pharm. Sci., 99(12):4812-4829). Experimental results show that the total charge dictates some of the viscosity at high concentrations, but also close range specific interactions are seen to be equally important (Yadav 2010, supra). The total charge along with the precise patterning of the charges is important to determine the self-association at high concentrations. Coarse-grained molecular dynamics simulations suggest that a decrease in viscosity in solution correlates to a decreases in Fab-Fab attractions. This is associated with the overall increase in net charge of the molecule (Chaudhri et al., 2013, J. Phys. Chem. B, 117(5): 1269-1279). Charge swapping experiments decreasing the asymmetric nature of the charge distribution correlates to decreases in viscosity (Ketchem et al., 2012, "Modification of Protein Viscosity by Modification of Protein Surface Charge" PEGS Symposium, Boston Mass., and Yadav et al., 2012, Mol. Pharmaceutics. 9(4):791-802). These suggest that self-association mediated by negative charge patches lead to highly viscous antibodies. Therefore, increasing the total charge to increase the repulsive force or reducing the size or effect of negative charge patches is an approach to reducing the viscosity of antibodies at high concentrations. The activity of the antibody may suffer though if this design is not done with knowledge of key interactions of the antibody-antigen complex (Ketchem 2012, supra).

Figure 11:
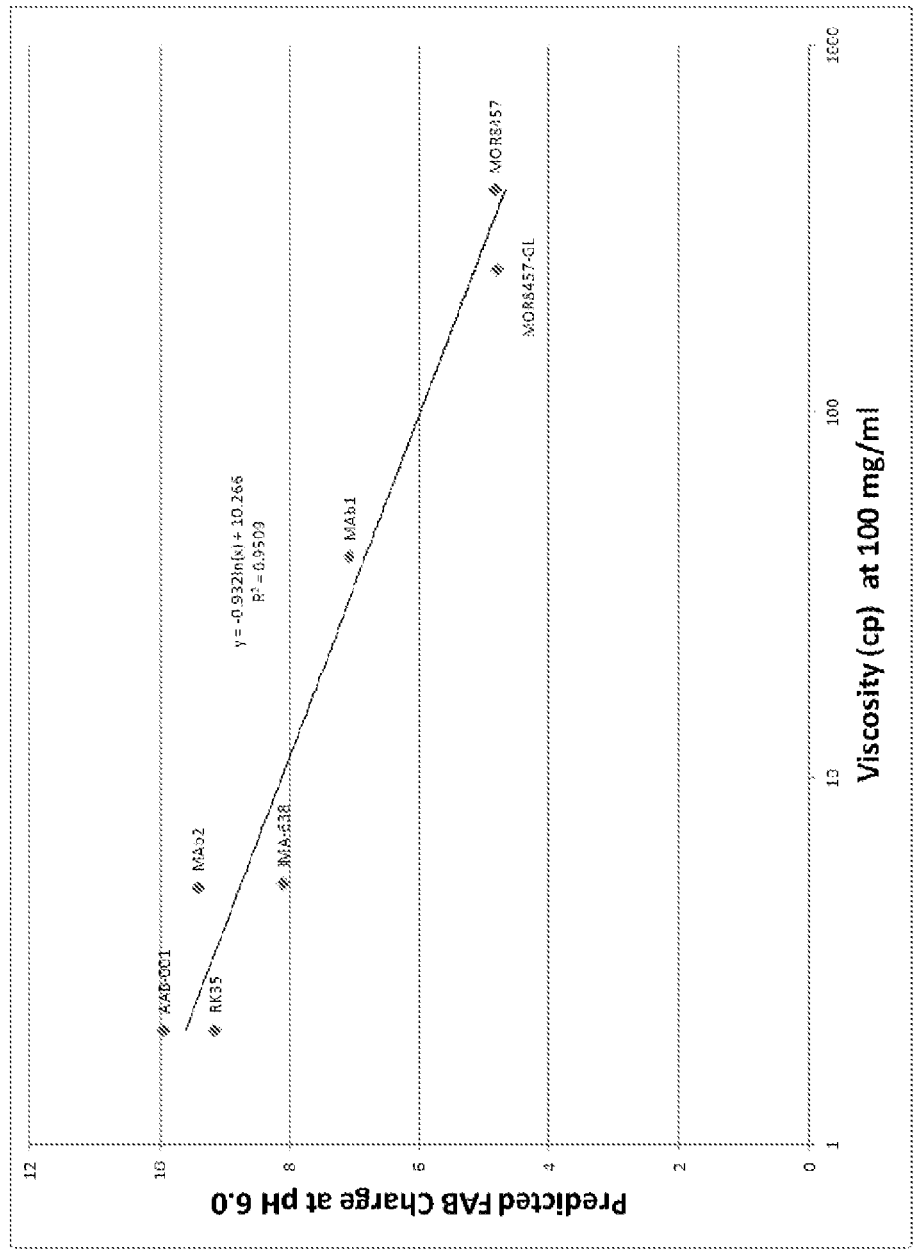
FIG. 11 depicts a graph showing the viscosity of seven antibodies at 100 mg/ml concentration in low salt and pH6.0 plotted against the Predicted FAB charge at pH6.0. The predicted FAB charge is calculated using the Discovery Studio 3.5 pKa predictor. The viscosity of antibodies AAB-001, RK35, IMA-638, MOR8457 and MOR8457-GL are measured as described in the methods. MAb1 and MAb2 viscosity measurements are described in Yadav 2012, supra.
Figure 12:
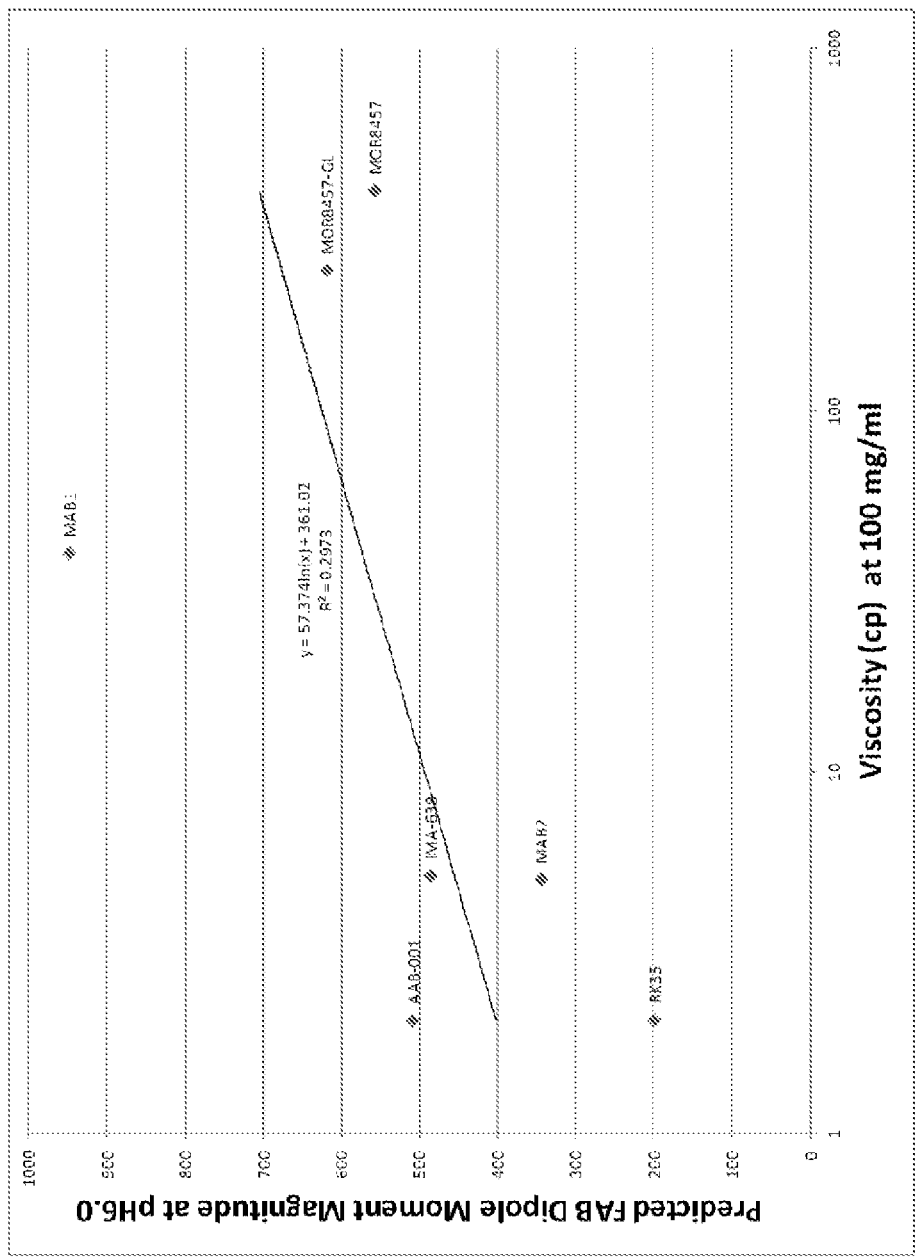
FIG. 12 shows the viscosity of seven antibodies at 100 mg/ml concentration in low salt and pH6.0 plotted against the Predicted Fab Dipole Moment Magnitude at pH 6.0. The predicted FAB charges were calculated using the Discovery Studio 3.5 pKa predictor. The dipole moment was then calculated using these charges. The viscosity of AAB-001, RK35, IMA-638, MOR8457 and MOR8457-GL were measured as described in the methods. MAb1 and MAb2 viscosity measurements are described in Yadav 2012, supra.
Figure 13:
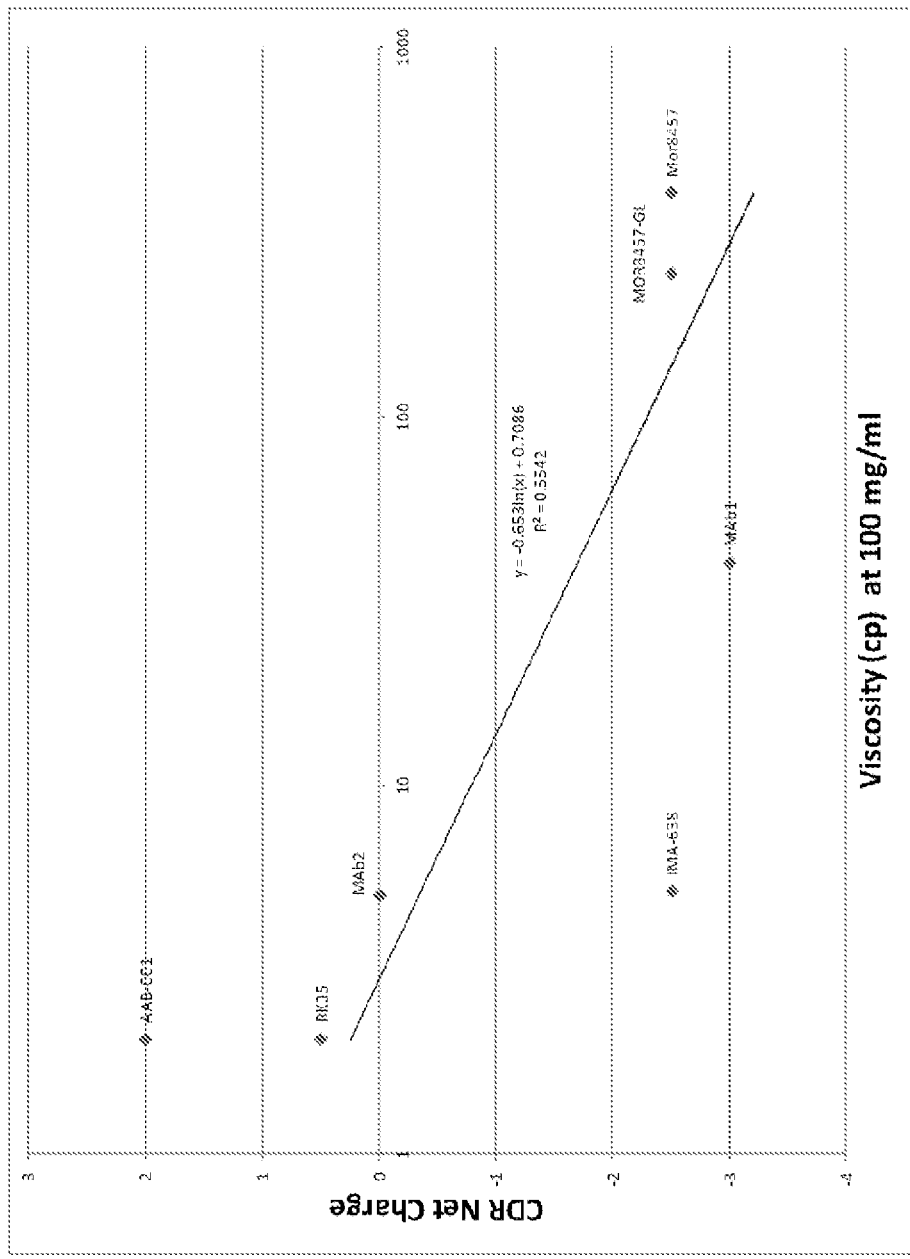
FIG. 13 depicts a graph showing the viscosity of seven antibodies at 100 mg/ml concentration in low salt and pH6.0 plotted against the net charge of the residues in the CDR region. The net charge is calculated by giving positive charged residues +1, negative charged residues -1, and H is a +½ charge. The viscosity of AAB-001, RK35, IMA-638, MOR8457 and MOR8457-GL are measured as described in the methods. MAb1 and MAb2 viscosity measurements are described in Yadav 2012, supra.
Figure 14:
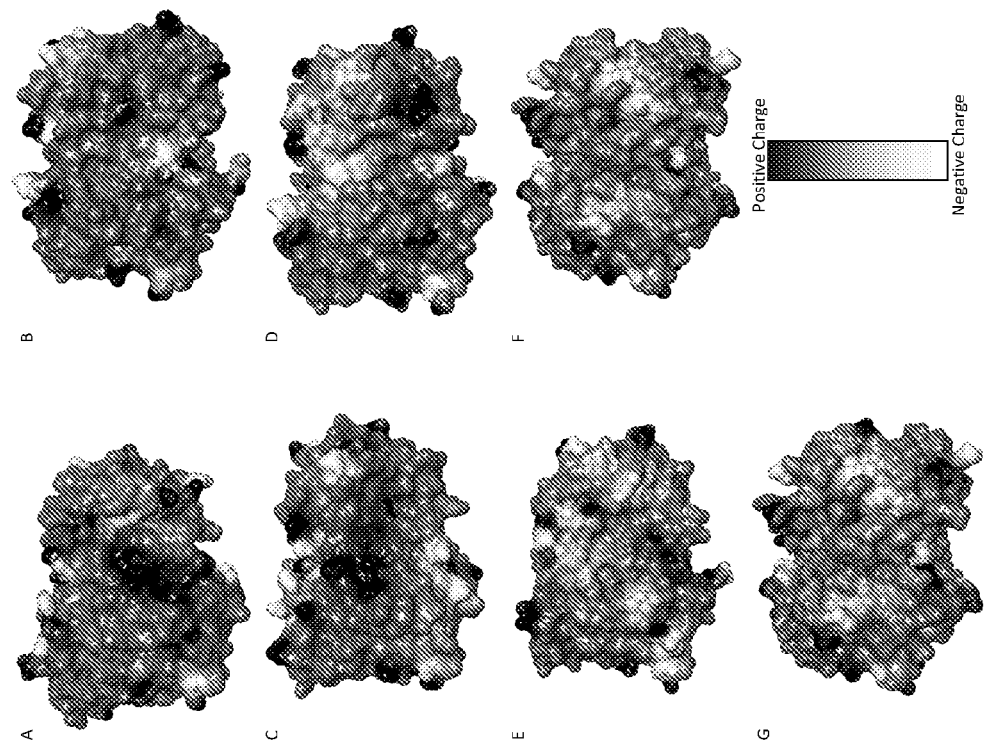
FIG. 14, comprising panels A through G, depicts the electrostatic potential energy surfaces highlighting the CDR regions of: (A) AAB-001 (B) RK35 (C) MAb2 (D) IMA-638 (E) MAb1 (F) MOR8457-GL (G) MOR8457. Surface charge is shown as a spectrum from black for positively charged patches to white for negatively charged patches as depicted by the bar at the bottom right hand of the figure. All molecules are shown oriented such that each CDR region is facing outward (out of the plane of the paper) with the heavy chain to the left and the light chain to the right.

Here, several parameters were examined to determine which, if any, parameter correlated strongly with changes in viscosity. This was done by examining seven different antibodies. The viscosities at high concentrations of five antibodies: AAB-001 (bapineuzumab, CAS Registry Number 648895-38-9), RK35 (U.S. Pat. No. 7,888,486), IMA- 638 (anrukinzumab, CAS Registry Number 910649-32-0), MOR8457 and MOR8457-GL were measured as described below. MAb1 and MAb2 are described in Yadav 2012, supra, including the measurements of their viscosities at high-concentrations. The viscosity was compared to the total charge of the Fab (FIG. 11), dipole moment of the Fab (FIG. 12) and net charge of the CDR (FIG. 13). For bapineuzumab and IMA-638, structural models of the Fab were required. For RK35, MAb1 and MAb2, crystal structures were available. For AAB-001, IMA-638, MOR8457 and MOR8457-GL homology models were generated using the Modeler package from Discovery Studio 3.5. For each of these models, the charge assignment was generated using the "Calculate Protein Ionization and Residue pK" package from Discovery Studio 3.5. Using the charges calculated, the total charge of the Fab at pH6.0 and the dipole moment were calculated. The net charge of the CDR was taken from sequence giving positive charged residues +1, negative charged residues −1, and H is a +½ charge. Looking at the comparison of the measurements, it is clear that the total charge ($R^2$=0.95) and net charge of the CDR($R^2$=0.55) correlated with the high concentration viscosity of the antibody. The dipole moment ($R^2$=0.29) also correlated somewhat with viscosity but not as strongly. In addition to point charge properties, an electrostatic potential energy surface map was calculated using the Delphi package of Discovery Studio 3.5 with Delphi Default Charges. The electrostatic potential energy surface of each antibody is shown in FIG. 14 with the low viscosity antibodies shown in panels A-D (AAB-001, RK35, MAb2 and IMA-638, respectively) and higher viscosity antibodies shown in panels E-G (Mab1, MOR8457-GL, and MOR8457, respectively). These data demonstrate that the higher viscosity antibodies have larger negative charge patches in their CDR regions (larger white patch in the figure) than the lower viscosity antibodies.

Design Strategy

The effect of charge and charge distribution on the viscosity of antibodies at high concentration, shown in FIGS. 11-14, correlates strongly with the finding described above (Yadav 2010, supra, Yadav 2012, supra, Ketchem 2012, supra, and Chaudhri 2013, supra). Moreover, for MOR8457-GL, which has high viscosity at high concentrations, it was demonstrated that the antibody has a low total charge (FIG. 11), negative net-charge in the CDR region (FIG. 13), and a large negative charged patch (FIG. 14F). Given these finding, a scheme was devised to identify residues that could increase the total charge, reduce the negative charged residues in the CDR, and/or block or reduce the negatively charged patch. Given the difficulty of other optimizations in maintaining activity of the antibody (Ketchem 2012, supra), additional constraints were included to make sure that binding affinity was not lost and that the framework regions remained highly homologous to human germlines. Based on the amino acid sequence of MOR8457-GL, distributions of amino acid probabilities from human antibodies for each site in frameworks -H1, -H2, -H3, -H4, -L1, -L2, -L3 and -L4 and CDR-H1, -H2, -H3, -L1, -L2, and -L3 were generated. For each segment, all human antibodies with the same length segment from publicly available databases, such as IMGT and the PDB, were aligned and the frequency at each position was determined. From the sets of framework residues all sites which had a high probability of Lys or Arg residues (>10%) or sites with a wild-type Glu or Asp that had a high probability of another neutral residue (>10%) were identified. For each of the sites the change in stability upon mutation and the charge in binding affinity upon mutation were calculated using Discovery Studio 3.5 and the MOR8457:PDGF-B crystal structure. For the CDR regions (a) all mutations of Glu or Asp to Gln, Asn and the most common residue type and (b) all other sites for mutations to Arg, Lys or H is were evaluated for the change in stability upon mutation and the charge in binding affinity upon mutation. From these calculations, a set of mutations were determined that were predicted to increase the net charge while not affecting stability or binding affinity (predicted ΔΔG<0.5 kcal/mol). The list of mutations is shown in Table 6.

TABLE 6

List of mutations which are predicted to increase the net charge without affecting stability or binding affinity.

| Viscosity Mutant Identity# | Mutation Position in Heavy or Light Chain (Kabat numbering) | Mutation Position in Heavy or Light Chain (Linear numbering) | Wild Type Amino Acid Residue in MOR8457-GL | Mutated Amino Acid Residue | Mutation Position in Heavy or Light Chain (Kabat numbering) | Mutation Position in Heavy or Light Chain (Linear numbering) | Wild Type Amino Acid Residue in MOR8457-GL | Mutated Amino Acid Residue |
|---|---|---|---|---|---|---|---|---|
| 1 | H1 | H1 | E | Q | | | | |
| 2 | H6 | H6 | E | Q | | | | |
| 3 | H85 | H89 | E | S | | | | |
| 4 | H101 | H108 | D | N | | | | |
| 5 | L3 | L3 | E | V | | | | |
| 6 | L60 | L59 | E | S | | | | |
| 7 | L96 | L95 | D | N | | | | |
| 8 | H13 | H13 | Q | K | | | | |
| 9 | H23 | H23 | A | R | | | | |
| 10 | H105 | H112 | Q | R | | | | |
| 11 | L18 | L17 | T | R | | | | |
| 12 | L20 | L19 | S | R | | | | |
| 13 | L42 | L41 | Q | R | | | | |
| 14 | L45 | L44 | V | R | | | | |
| 15 | L77 | L76 | G | R | | | | |
| 16 | H30 | H30 | S | H | | | | |
| 17 | H52 | H52 | S | H | | | | |
| 18 | H55 | H56 | S | H | | | | |
| 19 | H62 | H63 | S | H | | | | |
| 20 | L27 | L26 | S | H | | | | |
| 21 | L52 | L51 | S | H | | | | |

TABLE 6-continued

List of mutations which are predicted to increase the net charge without affecting stability or binding affinity.

| Viscosity Mutant Identity# | Mutation Position in Heavy or Light Chain (Kabat numbering) | Mutation Position in Heavy or Light Chain (Linear numbering) | Wild Type Amino Acid Residue in MOR8457-GL | Mutated Amino Acid Residue | Mutation Position in Heavy or Light Chain (Kabat numbering) | Mutation Position in Heavy or Light Chain (Linear numbering) | Wild Type Amino Acid Residue in MOR8457-GL | Mutated Amino Acid Residue |
|---|---|---|---|---|---|---|---|---|
| 22 | L52 | L51 | S | R | | | | |
| 23 | H28 | H28 | T | K | | | | |
| 24 | H60 | H61 | A | K | | | | |
| 25 | H81 | H82 | Q | R or K | | | | |
| 26 | L24 | L23 | S | R | | | | |
| 27 | L53 | L52 | N | K | | | | |
| 28 | H52A | H53 | D | N | | | | |
| 29 | H53 | H54 | D | N | | | | |
| 30 | L26 | L25 | D | N | | | | |
| 31 | H95 | H99 | H | R | | | | |
| 32 | H31 | H31 | S | R | | | | |
| 33 | H30 | H30 | S | R | | | | |
| 34 | H1 | H1 | E | Q | H6 | H6 | E | Q |
| 35 | H1 | H1 | E | Q | H13 | H13 | Q | K |
| 36 | H1 | H1 | E | Q | H105 | H112 | Q | R |
| 37 | H6 | H6 | E | Q | H13 | H13 | Q | K |
| 38 | H6 | H6 | E | Q | H105 | H112 | Q | R |
| 39 | H13 | H13 | Q | K | H105 | H112 | Q | R |
| 40 | L20 | L19 | S | R | L3 | L3 | E | V |

A subset of these mutations was tested experimentally. These were prioritized to include mutations whose total segment or surrounding residues were found in human germlines and mutations that were in close proximity to the negative charge patch in the CDR (as shown in FIG. 14F). Also, one double mutant was selected whose segment was found in a human germline (DP-21, IGHV7-4-1, IMGT Accession No. Z12323). Finally, combinations of heavy chain and light chain mutations were also selected. This was done because FIG. 11 suggests that it may require a charge change of +2 or +3 to reduce the viscosity to desirable levels. These experimentally tested MOR8457 variants and respective mutations incorporated therein are set forth in Table 7. It is understood that because the antibodies, or antigen-binding portion thereof, is dimeric, single mutants comprise two mutations per antibody molecule, i.e., one on each H or L chain. Similarly, where double mutations are present, the antibody comprises four (4) mutations since there are two heavy chains and two light chains. Where there are three (3) mutations which one on the H or L chain and two on the other H or L chain, the antibody comprises six mutations, and so on.

TABLE 7

Mutations Tested Experimentally

| MOR8457 variant | Mutation relative to MOR8457-GL | No. of Amino Acid Mutations |
|---|---|---|
| MOR8457-2 | single heavy (E6Q) | 1 |
| MOR8457-3 | single heavy (Q13K) | 1 |
| MOR8457-4 | single heavy (A23R) | 1 |
| MOR8457-5 | single heavy (D52aN) | 1 |
| MOR8457-6 | single heavy (Q105R) | 1 |
| MOR8457-7 | double heavy (E6Q, Q13K) | 2 |
| MOR8457-8 | single light (E3V) | 1 |
| MOR8457-9 | single light (T18R) | 1 |
| MOR8457-10 | single light (N53K) | 1 |
| MOR8457-11 | single light (D96N) | 1 |
| MOR8457-12 | double heavy (E6Q, Q13K) + single light (E3V) | 3 |

TABLE 7-continued

Mutations Tested Experimentally

| MOR8457 variant | Mutation relative to MOR8457-GL | No. of Amino Acid Mutations |
|---|---|---|
| MOR8457-13 | single heavy (E6Q) + single light (T18R) | 2 |
| MOR8457-14 | double heavy (E6Q, Q13K) + single light (T18R) | 3 |
| MOR8457-15 | double heavy (E6Q, Q13K) + single light (D96N) | 3 |
| MOR8457-16 | double heavy (E6Q, Q13K) + single light (N53K) | 3 |
| MOR8457-17 | single heavy (Q13K) + single light (T18R) | 2 |
| MOR8457-18 | single heavy (Q105R) + single light (T18R) | 2 |

Viscosity Measurements

Transient expression of full length IgG was performed in HEK-293F cells, which were transfected with expression vectors encoding the heavy and light chains separately (MOR8457-2 to MOR8457-18 from table 7). Cell culture supernatant was harvested three to seven days after transfection and cleared by centrifugation.

After filtration (0.22 μm or 0.45 μm), the supernatant was subjected to standard protein A or G affinity chromatography (MabSelect SURE, GE). Proteins were eluted at pH 3 and neutralized in 3 M TRIS, pH 8. Further downstream processing involved buffer exchange to 1× Dulbecco's PBS (Invitrogen) and sterile filtration (0.2 μm; Millipore or Sartorius). Purity was analyzed under denaturing, reducing and denaturing, non-reducing conditions in SDS-PAGE or by capillary electrophoresis. HP-SEC was performed to analyze IgG preparations in their native state.

Viscosity of the engineered variants of MOR8457 was measured as follows. Proteins in PBS were extensively dialyzed against 20 mM histidine, 85 mg/ml sucrose, 0.05 mg/ml EDTA pH 6.0 using membrane cassette devices 10K MWCO (Thermo Scientific). Proteins were harvested from dialysis and filtered using a 0.2 micron syringe filter. Proteins were concentrated using Vivaspin centrifugal concentrators 10K MWCO (GE Healthcare). Sample aliquots (12 µl) were removed from the concentrator retentate as the protein volume was reduced and the protein concentration increased. 300 nm beads (Nanosphere, Thermo Scientific) were added to the protein samples and buffer blank. The beads were diluted 1:10 in 20 mM histidine, 85 mg/ml sucrose, 0.05 mg/ml EDTA pH 6.0 and 0.75 µl diluted beads were spiked into the protein sample. The protein/bead and buffer/bead samples were mixed by gently vortexing. 8 µl sample was transferred to 1536 well plate (SensoPlate, glass bottom, Greiner Bio-One) for analysis by dynamic light scattering measurements (DLS). The plate was sealed with optically clear tape and centrifuged at 2000 RPM for 2 minutes to remove bubbles.

The DLS measurements were made using a DynaPro Plate Reader (Wyatt Technology, Santa Barbara, Calif.). Samples were incubated at 25° C. and measured with 15 consecutive 25 second acquisitions. Radius of the bead was averaged for data acquisitions that had acceptable decay curves. The viscosity was calculated based on the Stokes-Einstein equation. Sample viscosity was calculated as the measured apparent radius divided by the nominal bead radius times 0.893 cP, the viscosity of water at 25° C.

Figure 15:
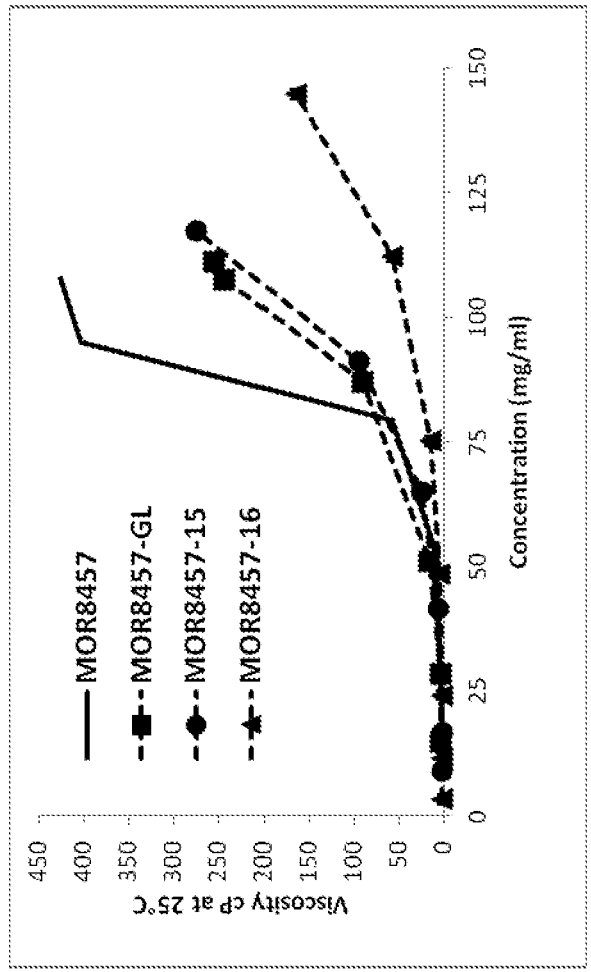
FIG. 15 depicts a graph showing the viscosity measurements for MOR8457 and engineered variants thereof as a function of increasing concentration. The parental MOR8457 antibody is shown as a solid line. Germlined MOR8457-GL is shown as a dotted line with solid squares. Engineered variant MOR8457-15 is shown as a dotted line with solid circles. Engineered variant MORR8457-16 is shown as a dotted line with solid triangles. The data shown demonstrate that the viscosity of MOR8457-16 is reduced compared with the other three MOR8457 antibodies.

The data demonstrate that variant MOR8547-16 showed substantially reduced viscosity compared to either the parental MOR-8457 antibody or the germlined MOR8457-GL construct (FIG. 15). MOR8457-15 did not show decreased viscosity compared with MOR8457-GL but demonstrated significantly decreased viscosity relative to the parental MOR8457 antibody.

Analysis of Top Clones

Figure 16:
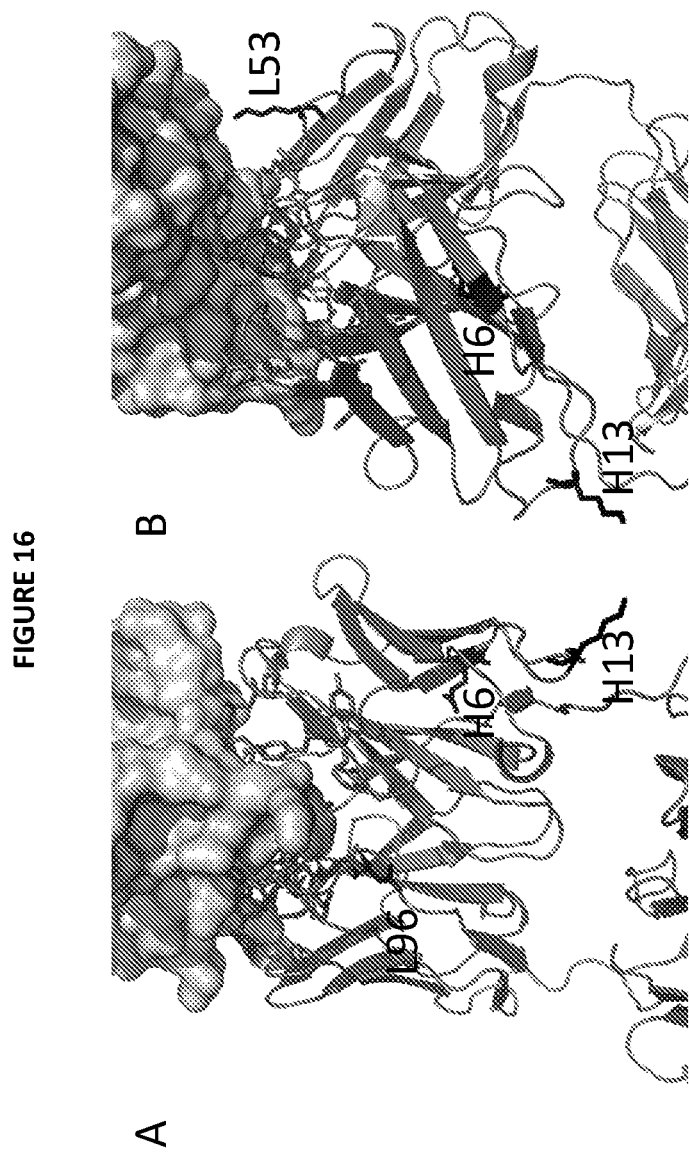
FIG. 16, comprising panels A and B, depicts a diagram showing the structural model of (A) MOR8457-15 and (B) MOR8457-16 in complex with a PDGF-BB dimer. The Fab is shown as gray ribbons and the PDGF-BB dimer is a light gray surface representation. The residues that are in direct contact with PDGF-BB are shown as gray sticks and those mutated residues relative to the parent antibody are shown as black sticks. The data shown demonstrate that for both engineered MOR8457, variants, none of the three mutations interact with PDGF-B dimer.
Figure 17:
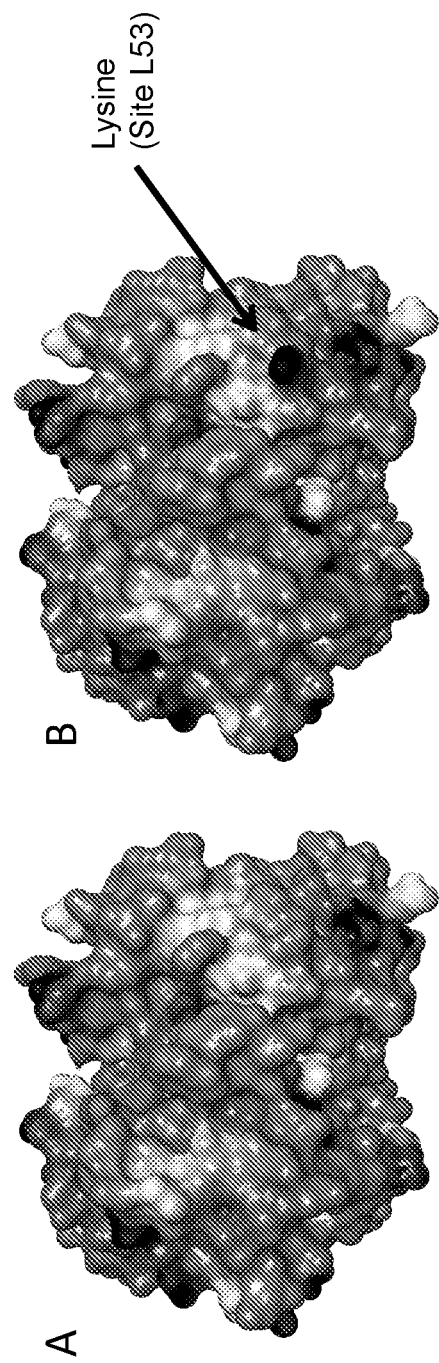
FIG. 17, comprising panels A and B, depicts the electrostatic potential energy surface of (A) MOR8457-GL and (B) MOR8457-16. The charge surface scaling shown in this figures is the same as that shown in FIG. 14. Site L53 which is mutated from Asn in MOR8457-GL to Lys in MOR8457-16, is indicated with the arrow. This residue is immediately adjacent to the large negatively charged patch in the light chain CDR (white patch above the L53 site) and these data suggest this residue is responsible for the decrease in viscosity relative to the parent antibody.
Figure 18:
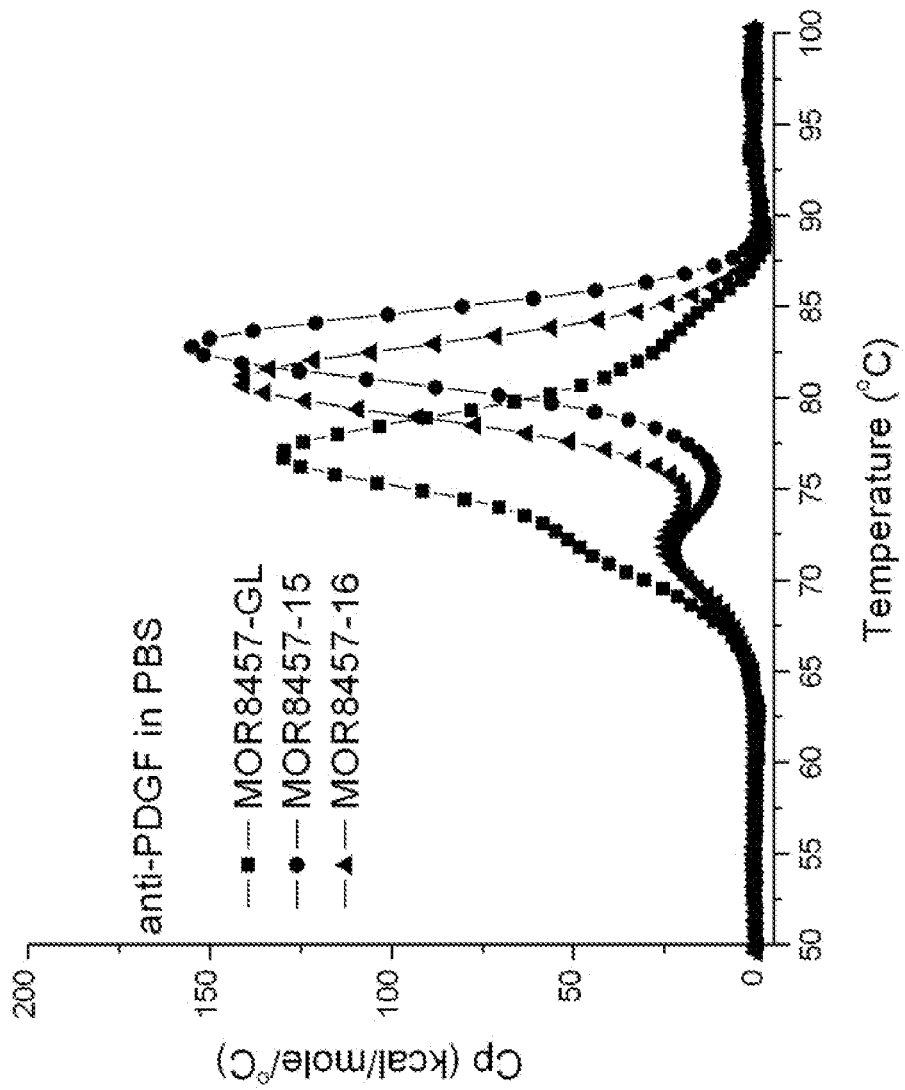
FIG. 18 depicts a graph showing the Differential Scanning calorimetry (DSC) profiles of MOR8457-GL (squares), MOR8457-15 (circles) and MOR8457-16 (triangles) in phosphate buffered saline.
Figure 19:
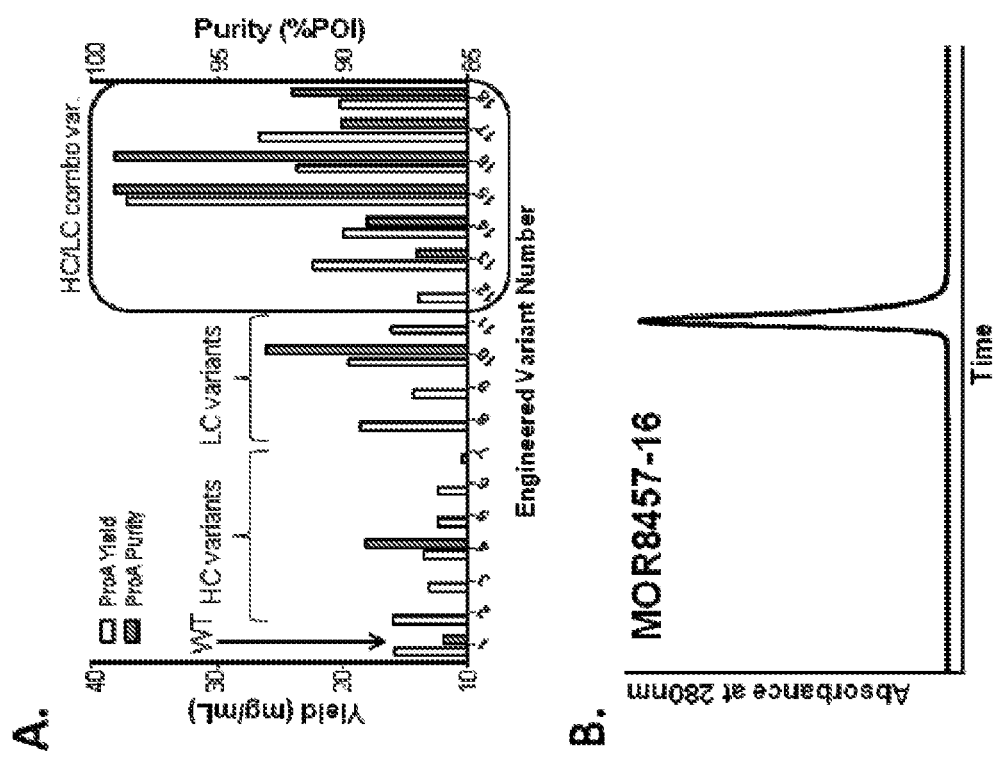
FIG. 19, comprising panels A and B, depicts a graph showing the expression and the purification profile of MOR8457 and its engineered variants, respectively. Panel A shows a bar graph showing the expression level (shown in white bars as mg/mL) after transient expression in 293 culture and purification yield after Protein A capture (shown as gray bars as percent peak area of interest) for each antibody. Panel B depicts a graph showing the analytical size exclusion chromatograph for MOR8457-16 after protein A elution showing a single peak.

Two clones, MOR8457-15 and MOR8457-16 showed increased stability and expression relative to the parental mAb MOR8457-GL (see examples 11, 12). In addition to stability and expression improvements, MOR8457-16 showed decreased viscosity relative to MOR8457 parental antibody and to MOR8457-GL. Both clones shared the heavy chain E6Q and Q13K mutations, while MOR8457-15 also had a light chain D96N mutation and MOR8457-16 had a light chain N53K mutation, i.e., they share a common heavy chain and differ in the light chain by a single amino acid residue. Homology models of these two mutants in complex with PDGF-B are shown in FIG. 16. These homology models were generated using the Modeler package of Discovery Studio 3.5 and the MOR8457:PDGF-B crystal structure. The heavy chain H6 and H13 sites are distant from the binding site, whereas light chain sites L96 and L53 are close to the binding site but do not directly interact with PDGF-B. Additionally FIG. 17 shows the proximity of the L53 site to the negatively charged patch in the light chain CDR region. This negatively charged patch is making direct contact with PDGF-B in the crystal structure and in homology models. Without wishing to be bound by any particular theory, the mutated light chain N53K residue seems to be able to block some of the self-association related to or mediated by this negative charge patch but is also far enough away from the PDGF-B binding site to not affect binding affinity.

Decreased viscosity is an important factor in the successful commercialization of a protein therapeutic as it relates to the ability to manufacture the protein in that it may provide decreased aggregation and may affect the ability to concentrate the protein to deliver the protein parenterally or subcutaneously. In addition, decreased viscosity may facilitate the delivery of the antibody to a patient, including the ability to administer through a delivery device comprising a smaller bore (i.e., internal diameter) and/or gauge (i.e., external diameter) and/or at a faster delivery rate. Also, as aggregates may be associated with the development of anti-drug antibodies (ADA), and since increased viscosity may relate to decreased aggregation, decreased viscosity may be an important factor in the successful commercialization of a protein therapeutic. Thus, decreased viscosity of the MOR8457 variants is an important desirable characteristic that may provide a significant advantage to the antibody as a potential novel therapeutic.

Example 11

Improved Stability of Engineered MOR8457 Variants

For evaluation of the thermal stability of the MOR8457 variant antibodies, protein samples were diluted in PBS (8.1 mM $Na_2HPO_4$, 1.47 mM $KH_2PO_4$, 137 mM NaCl, 2.7 mM KCl pH 7.2) to 0.3 mg/ml in a volume of 400 μl. PBS was used as a buffer blank in the reference cell. Samples were dispensed into the sample tray of a MicroCal VP-Capillary DSC with Autosampler (GE Healthcare Bio-Sciences, Piscataway, N.J.). Samples were equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions.

Two of the antibody variants, MOR8457-15 and MOR8457-16, showed increased thermal stability (FIG. 18) and expression (FIG. 19) relative to the parental mAb MOR8457-GL. The thermal stability and expression level of a potential therapeutic are important factors in the successful commercialization of the novel therapeutic as they impact, among other things, cost of goods.

Example 12

Improved Manufacturability Profile of Engineered MOR8457 Variants

Yield and Purity Analysis of MOR8457-GL and the Engineered Variants.

Analytical size-exclusion chromatography (SEC) and UV absorption spectroscopy was used to asses purity and yield following protein A capture of the panel of MOR8457 antibodies transiently expressed in HEK293 cells (FIG. 19 panel A). Protein A affinity chromatography was accomplished by first filtering HEK293 conditioned media through a 0.2 mm PES filter and then loading it on a Mab Select Sure (GE Healthcare) Protein A column equilibrated with 137 mM NaCl, 2.7 mM KCl, 8.1 mM $Na_2HPO_4$, 2.7 mM $KH_2PO_4$, pH 7.2 (PBS). The column was then washed with PBS and bound protein was eluted using 20 mM citric acid, 150 mM sodium chloride pH 2.5. Peak fractions were pooled, and neutralized with 2M Tris, pH8.0. Quantification of total captured protein was performed with UV absorption measurements at 280 nm and a molar extinction coefficient for each antibody. The extinction coefficients were derived using the Edelhoch method (Edelhoch H., 1967, Biochemistry 6:1948-1954) with the extinction coefficients for Trp and Tyr (Pace et al., 1995, Protein Sci. 4:2411-2423). SEC was performed on an Agilent 1200 HPLC (Agilent Technologies) fitted with a Superdex200 (GE Healthcare). For this, approximately 20 to 30 ug of protein was injected at a flow rate of 0.5 mL/min onto a column equilibrated in PBS and isocratic elution for 60 min. Protein was detected by absorption at 280 nm. The results of this analysis are shown as an increase in purity and protein A yield in the combination variants (FIG. 19 panel A; gray bars compared with white bars). In particular, MOR8457-16 showed >99% peak of interest (P01) in protein A eluate (FIG. 19 panel B) in addition to an increase in protein A yield. Improved manufacturability, including characteristics such as reduced viscosity and increased yield, is an important factor in the commercial development of a therapeutic as it impacts the cost of manufacturing and commercialization of the therapeutic.

Example 13

Binding Affinity, Specificity and Potency of MOR8457-16 Variant

The binding affinities of MOR8457-16 to different PDGF isoforms were determined as previously described (Example 6) using a Biacore 3000 (GE Healthcare, Piscataway N.J.). Briefly, an anti-human IgG (GE Healthcare) antibody was immobilized in flow cells of a CM5 sensor chip between 8,000-10,000 resonance units (RU) using amine coupling as directed by the manufacturer. Test antibodies were diluted into PBS-NET (10 mM Phosphate pH 7.4, 287 mM NaCl, 2.7 mM KCl, 3.2 mM EDTA, 0.01% Tween-20) to 0.5 ug/mL and injected over the anti-human antibody surface for 30 seconds resulting in a stable anti-PDGF surface between 82-122 RU. PDGF proteins were diluted to 1 nM in PBS-NET and serially diluted two-fold to 0.25 nM. Each concentration of PDGF was then injected over the antibody surface for 2 minutes at a flow rate of 100 ul/min. The complex was allowed to dissociate for 10 minutes. The surface was regenerated with a 30 second injection of 3M magnesium chloride leaving the surface ready for another round of anti-PDGF antibody capture and PDGF binding kinetics. Kinetic data was double referenced (D. G. Myszka et al., *J. Mol. Recognit.* 12:279, 1999) using Scrubber2 software (Bio-Logic Software), then fit to a 1:1 binding model using Biacore evaluation software version 4.1. Protein concentrations of all PDGF isoforms were corrected with active concentrations determined under the condition of limiting mass transport (Karlsson et al., *METHODS: A companion to Methods in Enzymology* 6:99-110, 1994). Results shown were averages of two independent binding studies.

Figure 20:
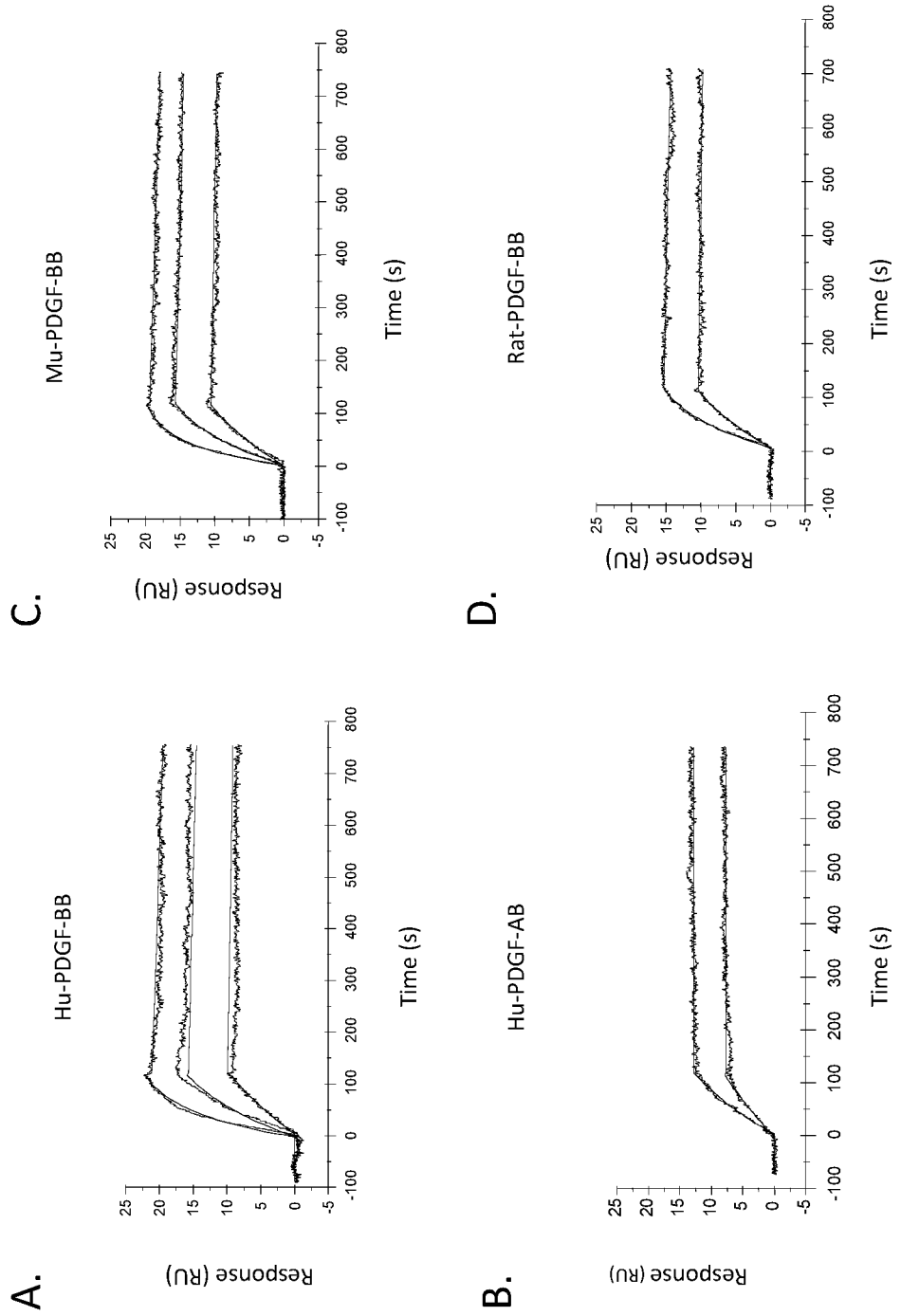
FIG. 20, comprising panels A through D, depicts Biacore sensorgrams showing the binding kinetics of MOR8457-16 to different PDGF isoforms. MOR8457-16 was captured onto CM5 chips using an anti-human IgG antibody. The binding kinetics of each PDGF isoform was assessed by flowing different concentrations of each PDGF isoform over the captured MOR8457-16 surface. The concentrations of Hu-PDGF-BB (A) and Mu-PDGF-BB (C) were 0.25, 0.5, and 1 nM, and the concentrations for Hu-PDGF-AB (B) and Rat-PDGF-BB (D) were 0.5 and 1 nM. Each sensorgram is one representative of two independent experiments. Kinetics data were double referenced and fit using Biacore evaluation software version 4.1. The on- and off-rates and binding affinities shown in this figure are listed in Table 8.

The MOR8457-16 antibody retained the low pM binding affinity to human PDGF-AB and BB and the cross reactivity to mouse and rat PDGF-BB (FIG. 20 and Table 8). Its binding affinity and specificity were comparable to that of parent MOR8457-GL (Example 6), suggesting that the mutations resulting in the improvement of the viscosity did not comprise the binding to PDGFs.

Figure 21:
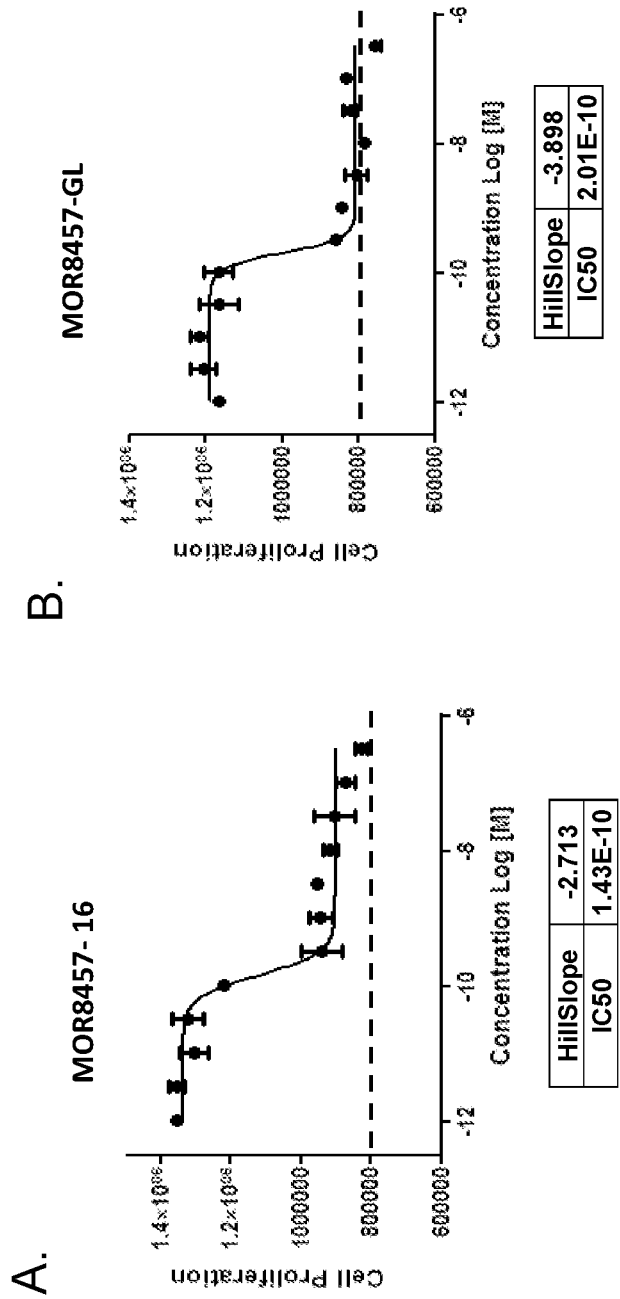
FIG. 21, comprising panels A and B, show graphs depicting the inhibition curve of MOR8457-16 (A) and MOR8457-GL (B) in the mesangial cell proliferation assay. Cell proliferation was stimulated with 2.5 ng/ml of PDGF-BB. The assay was performed as described in Example 8. The $IC_{50}$ of MOR8457-16 was 14 pM while the $IC_{50}$ of parent MOR8457-GL was 20 pM.

In order to confirm the functional activity of MOR8457-16, we tested its inhibition of mesangial cell proliferation. The assay was performed as described previously (Example 8). Briefly, antibodies were half-log diluted from 100 nM down to 0.1 nM then mixed with 2.5 ng/ml of PDGF-BB in serum-free MCM media with 0.1% BSA for 30 minutes before adding to the cells. FIG. 21 shows the inhibition curve of MOR8457-16 (A) compared with parent MOR8457-GL (B) in the same experiment. The $IC_{50}$ of MOR8457-16 is 14 pM, which is similar to the $IC_{50}$ of parent MOR8457 of 20 pM.

TABLE 8

Binding affinity and specificity of MOR8457-16 to different PDGF isoforms determined by Biacore

| Analyte | Ligand | $k_a$ (M$^{-1}$s$^{-1}$) | $k_d$ (s$^{-1}$) | $K_D$ (M) |
|---|---|---|---|---|
| Hu PDGF-BB | MOR8457-16 | 1.73 (±0.06) × 10$^7$ | 1.69 (±0.58) × 10$^{-4}$ | 9.75 (±3.43) × 10$^{-9}$ |
| Mu PDGF-BB | MOR8457-16 | 2.16 (±0.29) × 10$^7$ | 1.80 (±0.47) × 10$^{-4}$ | 8.62 (±3.15) × 10$^{-9}$ |
| Rat PDGF-BB | MOR8457-16 | 1.29 (±0.14) × 10$^7$ | 1.14 (±0.04) × 10$^{-4}$ | 8.88 (±1.31) × 10$^{-9}$ |
| Hu PDGF-AB | MOR8457-16 | 3.39 (±4.73) × 10$^6$ | 4.28 (±3.06) × 10$^{-7}$ | 8.02 (±11.29) × 10$^{-9}$ |

Note:
Data are average of two independent experiments.

SUMMARY OF SEQUENCE LISTING

| SEQ ID NO: | Description | Sequence |
|---|---|---|
| 1 | AA sequence of MOR8457 light chain V domain (MOR8457-VL) | SYELTQPPSVSVAPGQTARISCSGDSLGSYFVHWYQQKPGQAP VLVIYDDSNRPSGIPERFSGSNSGNTATLTISGTQAEDEADYY CSAFTHNSDVFGGGTKLTVL |
| 2 | AA sequence of MOR8457 heavy chain V domain (MOR8457-VH) | EVQLVESGGGLVQPGGSLRLSCAASGFTFSSYAMSWVRQAPGK GLEWVSYISDDGSLKYYADSVKGRFTISRDNSKNTLYLQMNSL RAEDTAVYYCARHPYWYGGQLDLWGQGTLVTVSS |
| 3 | NA encoding MOR8457 light chain V domain germlined (MOR8457-GL-VL) | AGCTACGAGCTGACCCAGCCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAACAGACCCAGCGGCATCC CCGAGAGATTCAGCGGCAGCAACAGCGGCAACACCGCCACCCT |

| SEQ ID NO: | Description | Sequence |
|---|---|---|
| | | GACCATCAGCGGCACCCAGGCCATGGACGAGGCCGACTACTAC TGCAGCGCCTTCACCCACAACAGCGACGTGTTCGGCGGCGGCA CCAAGCTGACCGTGCTA |
| 4 | AA sequence of MOR8457 light chain V domain germlined (MOR8457-GL-VL) | SYELTQPPSVSVSPGQTASITCSGDSLGSYFVHWYQQKPGQSP VLVIYDDSNRPSGIPERFSGSNSGNTATLTISGTQAMDEADYY CSAFTHNSDVFGGGTKLTVL |
| 5 | NA encoding MOR8457 heavy chain V domain germlined (MOR8457-GL-VH) | GAGGTGCAGCTGCTGGAGAGCGGCGGCGGCCTGGTGCAGCCCG GCGGCAGCCTGAGACTGAGCTGCGCCGCCAGCGGCTTCACCTT CAGCAGCTACGCCATGAGCTGGGTGAGACAGGCCCCCGGCAAG GGCCTGGAGTGGGTGAGCTACATCAGCGACGACGGCAGCCTGA AGTACTACGCCGACAGCGTGAAGGGCAGATTCACCATCAGCAG AGACAACAGCAAGAACACCCTGTACCTGCAGATGAACAGCCTG AGAGCCGAGGACACCGCCGTGTACTACTGCGCCAAACACCCCT ACTGGTACGGCGGCCAGCTGGACCTGTGGGGCCAGGGCACCCT GGTGACCGTGTCCTCA |
| 6 | AA sequence of MOR8457 heavy chain V domain germlined (MOR8457-GL-VH) | EVQLLESGGGLVQPGGSLRLSCAASGFTFSSYAMSWVRQAPGK GLEWVSYISDDGSLKYYADSVKGRFTISRDNSKNTLYLQMNSL RAEDTAVYYCAKHPYWYGGQLDLWGQGTLVTVSS |
| 7 | MOR8457 CDR-H1 | GFTFSSYAMS |
| 8 | MOR8457 CDR-H2 | YISDDGSLKYYADSVKG |
| 9 | MOR8457 CDR-H3 | HPYWYGGQLDL |
| 10 | MOR8457 CDR-L1 | SGDSLGSYFVH |
| 11 | MOR8457 CDR-L2 | DDSNRPS |
| 12 | MOR8457 CDR-L3 | SAFTHNSDV |
| 13 | NA encoding MOR8457 full length heavy chain germlined with triple effector null mutant IgG1 constant domain (MOR8457-GL- hIgG1-3m- -HC) | GAGGTGCAGCTGCTGGAGAGCGGCGGCGGCCTGGTGCAGCCCG GCGGCAGCCTGAGACTGAGCTGCGCCGCCAGCGGCTTCACCTT CAGCAGCTACGCCATGAGCTGGGTGAGACAGGCCCCCGGCAAG GGCCTGGAGTGGGTGAGCTACATCAGCGACGACGGCAGCCTGA AGTACTACGCCGACAGCGTGAAGGGCAGATTCACCATCAGCAG AGACAACAGCAAGAACACCCTGTACCTGCAGATGAACAGCCTG AGAGCCGAGGACACCGCCGTGTACTACTGCGCCAAACACCCCT ACTGGTACGGCGGCCAGCTGGACCTGTGGGGCCAGGGCACCCT GGTGACCGTGTCCTCAGCGTCGACCAAGGGCCCATCGGTCTTC CCCCTGGCACCCTCCTCCAAGAGCACCTCTGGGGGCACAGCGG CCCTGGGCTGCCTGGTCAAGGACTACTTCCCCGAACCGGTGAC GGTGTCGTGGAACTCAGGCGCCCTGACCAGCGGCGTGCACACC TTCCCGGCTGTCCTACAGTCCTCAGGACTCTACTCCCTCAGCA GCGTGGTGACCGTGCCCTCCAGCAGCTTGGGCACCCAGACCTA CATCTGCAACGTGAATCACAAGCCCAGCAACACCAAGGTGGAC AAGAAAGTTGAGCCCAAATCTTGTGACAAAACTCACACATGCC CACCGTGCCCAGCACCTGAAGCCGCTGGGGCACCGTCAGTCTT CCTCTTCCCCCCAAAACCCAAGGACACCCTCATGATCTCCCGG ACCCCTGAGGTCACATGCGTGGTGGTGGACGTGAGCCACGAAG ACCCTGAGGTCAAGTTCAACTGGTACGTGGACGGCGTGGAGGT GCATAATGCCAAGACAAAGCCGCGGGAGGAGCAGTACAACAGC ACGTACCGTGTGGTCAGCGTCCTCACCGTCCTGCACCAGGACT GGCTGAATGGCAAGGAGTACAAGTGCAAGGTCTCCAACAAAGC CCTCCCAGCCCCCATCGAGAAAACCATCTCCAAAGCCAAAGGG CAGCCCCGAGAACCACAGGTGTACACCCTGCCCCCATCCCGGG AGGAGATGACCAAGAACCAGGTCAGCCTGACCTGCCTGGTCAA AGGCTTCTATCCCAGCGACATCGCCGTGGAGTGGGAGAGCAAT GGGCAGCCGGAGAACAACTACAAGACCACGCCTCCCGTGCTGG ACTCCGACGGCTCCTTCTTCCTCTATAGCAAGCTCACCGTGGA CAAGAGCAGGTGGCAGCAGGGGAACGTCTTCTCATGCTCCGTG ATGCATGAGGCTCTGCACAACCACTACACGCAGAAGAGCCTCT CCCTGTCCCCGGGA |
| 14 | AA sequence of MOR8457 full length heavy chain germlined with triple effector null mutant IgG1 constant | EVQLLESGGGLVQPGGSLRLSCAASGFTFSSYAMSWVRQAPGK GLEWVSYISDDGSLKYYADSVKGRFTISRDNSKNTLYLQMNSL RAEDTAVYYCAKHPYWYGGQLDLWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPEAAGAPSVFLFPPKPKDTLMISR |

| SEQ ID NO: | Description | Sequence |
|---|---|---|
| | domain (MOR8457-GL-hIgG1-3m-HC) | TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPG |
| 15 | NA encoding germlined MOR8457 full length light chain (MOR8457-GL-LC) | AGCTACGAGCTGACCCAGCCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAACAGACCCAGCGGCATCC CCGAGAGATTCAGCGGCAGCAACAGCGGCAACACCGCCACCCT GACCATCAGCGGCACCCAGGCCATGGACGAGGCCGACTACTAC TGCAGCGCCTTCACCCACAACAGCGACGTGTTCGGCGGCGGCA CCAAGCTGACCGTGCTAGGTCAGCCCAAGGCTGCCCCCTCGGT CACTCTGTTCCCGCCCTCCTCTGAGGAGCTTCAAGCCAACAAG GCCACACTGGTGTGTCTCATAAGTGACTTCTACCCGGGAGCCG TGACAGTGGCCTGGAAGGCAGATAGCAGCCCCGTCAAGGCGGG AGTGGAGACCACCACACCCTCCAAACAAAGCAACAACAAGTAC GCGGCCAGCAGCTATCTGAGCCTGACGCCTGAGCAGTGGAAGT CCCACAGAAGCTACAGCTGCCAGGTCACGCATGAAGGGAGCAC CGTGGAGAAGACAGTGGCCCCTACAGAATGTTCA |
| 16 | AA sequence of MOR8457 full length light chain germlined (MOR8457-GL-LC) | SYELTQPPSVSVSPGQTASITCSGDSLGSYFVHWYQQKPGQSP VLVIYDDSNRPSGIPERFSGSNSGNTATLTISGTQAMDEADYY CSAFTHNSDVFGGGTKLTVLGQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| 17 | AA of MOR8457-IKR full length light chain (MOR8457-IKR-LC) | SYELTQPPSVSVAPGQTARISCSGDSLGSYFVHWYQQKPGQAP VLVIYDDSNRPSGIPERFSGSNSGNTATLTISGTQAEDEADYY CSAFTHNSDVFGGGTKLTIKRQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| 18 | AA MOR8457-hIgG1 full length heavy chain with triple effector null mutant IgG1 constant domain (MOR8457-hIgG1-3m-HC) | EVQLVESGGGLVQPGGSLRLSCAASGFTFSSYAMSWVRQAPGK GLEWVSYISDDGSLKYYADSVKGRFTISRDNSKNTLYLQMNSL RAEDTAVYYCARHPYWYGGQLDLWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPEAAGAPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPG |
| 19 | AA sequence of wild type human IgG1 constant region (hIgG1) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRWQ QGNVFSCSVMHEALHNHYTQKSLSLSPGK |
| 20 | AA sequence of wild type mouse IgG1 (mIgG1) | AKTTPPSVYPLAPGSAAQTNSVTLGCLVKGYFPEPVTVTWNSG SLSSGVHTFPAVLQSDLYTLSSSVTVPSSTWPSETVTCNVAHP ASSTKVDKKIVPRDCGCKPCICTVPEVSSVFIFPPKPKDVLTI TLTPKVTCVVVDISKDDPEVQFSWFVDDVEVHTAQTQPREEQF NSTFRSVSELPIMHQDWLNGKEFKCRVNSAAFPAPIEKTISKT KGRPKAPQVYTIPPPKEQMAKDKVSLTCMITDFFPEDITVEWQ WNGQPAENYKNTQPIMDTDGSYFVYSKLNVQKSNWEAGNTFTC SVLHEGLHNHHTEKSLSHSPGK |
| 21 | AA sequence of human IgG1 triple mutant (3m) effector null mutant constant region (hIgG1-3m) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEAAGAPSVFLFPPK PKDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRWQ QGNVFSCSVMHEALHNHYTQKSLSLSPG |

| SEQ ID NO: | Description | Sequence |
|---|---|---|
| 22 | AA sequence of human wild type IgG2 constant region (hIgG2) | ASFKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTVVVDVSHEDPEVQFNWYVDGVEVHNAKTKPRE EQFNSTFCVVSVLTVVHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |
| 23 | Human wild type lambda constant domain (Cλ) | GQPKAAPSVTLFPPSSEELQANKATLVCLISDFYPGAVTVAWK ADSSPVKAGVETTTPSKQSNNKYAASSYLSLTPEQWKSHRSYS CQVTHEGSTVEKTVAPTECS |
| 24 | Mouse wild type light lambda chain constant domain | QPKSSPSVTLFPPSSEELETNKATLVCTITDFYPGVVTVDWFT KVDGTPVTQGMETTQPSKQSNNKYMASSYLTLTARAWERHSSY SCQVTHEGHTVEFTKSLSRADCS |
| 25 | IGHV3-23*01 (DP-54) | EVQLLESGGGLVQPGGSLRLSCAASGFTFSSYAMSWVRQAPGK GLEWVSAISGSGGSTYYADSVKGRFTISRDNSKNTLYLQMNSL RAEDTAVYYCAK |
| 26 | IGHV3-23*02 | EVQLLESGGGLVQPGGSLRLSCAASGFTFSSYAMSWVRQAPGK GLEWVSAISGSGGSTYYGDSVKGRFTISRDNSKNTLY LQMNSLRAEDTAVYYCAK |
| 27 | IGHV3-23*03 | EVQLLESGGGLVQPGGSLRLSCAASGFTFSSYAMSWVRQAPGK GLEWVSVIYSGGSSTYYADSVKGRFTISRDNSKNTLY LQMNSLRAEDTAVYYCAK |
| 28 | IGHV3-23*05 | EVQLLESGGGLVQPGGSLRLSCAASGFTFSSYAMSWVRQAPGK GLEWVSAIYSSGSSTYYADSVKGRFTISRDNSKNTLY LQMNSLRAEDTAVYYCAK |
| 29 | IGLV3-1*01 (DPL-23) | SYELTQPPSVSVSPGQTASITCSGDKLGDKYACWYQQKPGQSP VLVIYQDSKRPSGIPERFSGSNSGNTATLTISGTQAMDEADYY C |
| 30 | IGLV3-25*03 | SYELTQPPSVSVSPGQTARITCSGDALPKQYAYWYQQKPGQAP VLVIYKDSERPSGIPERFSGSSSGTTVTLTISGVQAE DEADYYC |
| 31 | IGLV3-9*01 | SYELTQPLSVSVALGQTARITCGGNNIGSKNVHWYQQKPGQAP VLVIYRDSNRPSGIPERFSGSNSGNTATLTISRAQAG DEADYYC |
| 32 | IGLV3-25*01 | SYELMQPPSVSVSPGQTARITCSGDALPKQYAYWYQQKPGQAP VLVIYKDSERPSGIPERFSGSSSGTTVTLTISGVQAE DEADYYC |
| 33 | AA sequence of human PDGF-B | MNRCWALFLSLCCYLRLVSAEGDPIPEELYEMLSDHSIRSFDD LQRLLHGDPGEEDGAELDLNMTRSHSGGELESLARGRRSLGSL TIAEPAMIAECKTRTEVFEISRRLIDRTNANFLVWPPCVEVQR CSGCCNNRNVQCRPTQVQLRPVQVRKIEIVRKKPIFKKATVTL EDHLACKCETVAAARPVTRSPGGSQEQRAKTPQTRVTIRTVRV RRPPKGKHRKFKHTHDKTALKETLGA |
| 34 | AA sequence of MOR8457-15 light chain engineered V domain (MOR8457-15-VL) | SYELTQPPSVSVSPGQTASITCSGDSLGSYFVHWYQQKPGQSP VLVIYDDSNRPSGIPERFSGSNSGNTATLTISGTQAMDEADYY CSAFTHNSNVFGGGTKLTVL |
| 35 | NA sequence of MOR8457-15 light chain engineered V domain (MOR8457-15-VL) | AGCTACGAGCTGACCCAGCCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAACAGACCCAGCGGCATCC CCGAGAGATTCAGCGGCAGCAACAGCGGCAACACCGCCACCCT GACCATCAGCGGCACCCAGGCCATGGACGAGGCCGACTACTAC TGCAGCGCCTTCACCCACAACAGCAACGTGTTCGGCGGCGGCA CCAAGCTGACCGTGCTA |

-continued

| SEQ ID NO: | Description | Sequence |
|---|---|---|
| 36 | MOR8457-15 CDR-L3 | SAFTHNSNV |
| 37 | AA sequence of full length MOR8457-15 light chain with engineered V domain (MOR8457-15-LC) | SYELTQPPSVSVSPGQTASITCSGDSLGSYFVHWYQQKPGQSP VLVIYDDSNRPSGIPERFSGSNSGNTATLTISGTQAMDEADYY CSAFTHNSNVFGGGTKLTVLGQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| 38 | NA sequence of full length MOR8457-15 light chain with engineered V domain (MOR8457-15-LC) | AGCTACGAGCTGACCCAGCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAACAGACCCAGCGGCATCC CCGAGAGATTCAGCGGCAGCAACAGCGGCAACACCGCCACCCT GACCATCAGCGGCACCCAGGCCATGGACGAGGCCGACTACTAC TGCAGCGCCTTCACCCACAACAGCAACGTGTTCGGCGGCGGCA CCAAGCTGACCGTGCTAGGTCAGCCCAAGGCTGCCCCCTCGGT CACTCTGTTCCCGCCCTCCTCTGAGGAGCTTCAAGCCAACAAG GCCACACTGGTGTGTCTCATAAGTGACTTCTACCCGGGAGCCG TGACAGTGGCCTGGAAGGCAGATAGCAGCCCCGTCAAGGCGGG AGTGGAGACCACCACACCCTCCAAACAAAGCAACAACAAGTAC GCGGCCAGCAGCTATCTGAGCCTGACGCCTGAGCAGTGGAAGT CCCACAGAAGCTACAGCTGCCAGGTCACGCATGAAGGGAGCAC CGTGGAGAAGACAGTGGCCCCTACAGAATGTTCA |
| 39 | AA sequence of MOR8457-16 light chain V domain (MOR8457-16-VL) | SYELTQPPSVSVSPGQTASITCSGDSLGSYFVHWYQQKPGQSP VLVIYDDSKRPSGIPERFSGSNSGNTATLTISGTQAMDEADYY CSAFTHNSDVFGGGTKLTVL |
| 40 | NA sequence of MOR8457-16 light chain V domain (MOR8457-16-VL) | AGCTACGAGCTGACCCAGCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAAGAGACCCAGCGGCATCC CCGAGAGATTCAGCGGCAGCAACAGCGGCAACACCGCCACCCT GACCATCAGCGGCACCCAGGCCATGGACGAGGCCGACTACTAC TGCAGCGCCTTCACCCACAACAGCGACGTGTTCGGCGGCGGCA CCAAGCTGACCGTGCTA |
| 41 | MOR8457-16 CDR-L2 | DDSKRPS |
| 42 | AA sequence of full length MOR8457-16 light chain with engineered V domain (MOR8457-16-LC) | SYELTQPPSVSVSPGQTASITCSGDSLGSYFVHWYQQKPGQSP VLVIYDDSKRPSGIPERFSGSNSGNTATLTISGTQAMDEADYY CSAFTHNSDVFGGGTKLTVLGQPKAAPSVTLFPPSSEELQANK ATLVCLISDFYPGAVTVAWKADSSPVKAGVETTTPSKQSNNKY AASSYLSLTPEQWKSHRSYSCQVTHEGSTVEKTVAPTECS |
| 43 | NA sequence of full length MOR8457-16 light chain with engineered V domain (MOR8457-16-LC) | AGCTACGAGCTGACCCAGCCCCCAGCGTGAGCGTGTCCCCCG GCCAGACCGCCAGCATCACCTGCAGCGGCGACAGCCTGGGCAG CTACTTCGTACACTGGTACCAGCAGAAGCCCGGCCAGTCCCCC GTGCTGGTGATCTACGACGACAGCAAGAGACCCAGCGGCATCC CCGAGAGATTCAGCGGCAGCAACAGCGGCAACACCGCCACCCT GACCATCAGCGGCACCCAGGCCATGGACGAGGCCGACTACTAC TGCAGCGCCTTCACCCACAACAGCGACGTGTTCGGCGGCGGCA CCAAGCTGACCGTGCTAGGTCAGCCCAAGGCTGCCCCCTCGGT CACTCTGTTCCCGCCCTCCTCTGAGGAGCTTCAAGCCAACAAG GCCACACTGGTGTGTCTCATAAGTGACTTCTACCCGGGAGCCG TGACAGTGGCCTGGAAGGCAGATAGCAGCCCCGTCAAGGCGGG AGTGGAGACCACCACACCCTCCAAACAAAGCAACAACAAGTAC GCGGCCAGCAGCTATCTGAGCCTGACGCCTGAGCAGTGGAAGT CCCACAGAAGCTACAGCTGCCAGGTCACGCATGAAGGGAGCAC CGTGGAGAAGACAGTGGCCCCTACAGAATGTTCA |
| 44 | AA sequence of MOR8457-15/16 heavy chain engineered V domain (MOR8457-15-VH, and MOR8457-16-VH) | EVQLLQSGGGLVKPGGSLRLSCAASGFTFSSYAMSWVRQAPGK GLEWVSYISDDGSLKYYADSVKGRFTISRDNSKNTLYLQMNSL ARDTAVYYCARHPYWYGGQLDLWGQGTLVTVSS |
| 45 | NA sequence of MOR8457-15/16 heavy chain engineered V domain (MOR8457-15-VH, and MOR8457-16-VH) | GAGGTGCAGCTGCTGCAGAGCGGCGGCGGCCTGGTGAAGCCCG GCGGCAGCCTGAGACTGAGCTGCGCCGCCAGCGGCTTCACCTT ACGCAGCTACGCCATGAGCTGGGTGAGACAGGCCCCCGGCAAG GGCCTGGAGTGGGTGAGCTACATCAGCGACGACGGCAGCCTGA AGTACTACGCCGACAGCGTGAAGGGCAGATTCACCATCAGCAG AGACAACAGCAAGAACACCCTGTACCTGCAGATGAACAGCCTG |

| SEQ ID NO: | Description | Sequence |
|---|---|---|
| | | AGAGCCGAGGACACCGCCGTGTACTACTGCGCCAGACACCCCT ACTGGTACGGCGGCCAGCTGGACCTGTGGGGCCAGGGCACCCT GGTGACCGTGTCCTCAGC |
| 46 | AA MOR8457-15/16 hIgG1 full length heavy chain with engineered V domain and triple effector null mutant IgG1 constant domain (MOR8457-15-HC, and MOR8457-16-HC) | EVQLLQSGGGLVKPGGSLRLSCAASGFTFSSYAMSWVRQAPGK GLEWVSYISDDGSLKYYADSVKGRFTISRDNSKNTLYLQMNSL AREDTAVYYCARHPYWYGGQLDLWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPEAAGAPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPG |
| 47 | NA MOR8457-15/16 hIgG1 full length heavy chain with engineered V domain and triple effector null mutant IgG1 constant domain (MOR8457-15-HC, and MOR8457-16-HC) | GAGGTGCAGCTGCTGCAGAGCGGCGGCGGCCTGGTGAAGCCCG GCGGCAGCCTGAGACTGAGCTGCGCCGCCAGCGGCTTCACCTT ACGCAGCTACGCCATGAGCTGGGTGAGACAGGCCCCCGGCAAG GGCCTGGAGTGGGTGAGCTACATCAGCGACGACGGCAGCCTGA AGTACTACGCCGACAGCGTGAAGGGCAGATTCACCATCAGCAG AGACAACAGCAAGAACACCCTGTACCTGCAGATGAACAGCCTG AGAGCCGAGGACACCGCCGTGTACTACTGCGCCAGACACCCCT ACTGGTACGGCGGCCAGCTGGACCTGTGGGGCCAGGGCACCCT GGTGACCGTGTCCTCAGCGTCGACCAAGGGCCCATCGGTCTTC CCCCTGGCACCCTCCTCCAAGAGCACCTCTGGGGGCACAGCGG CCCTGGGCTGCCTGGTCAAGGACTACTTCCCCGAACCGGTGAC GGTGTCGTGGAACTCAGGCGCCCTGACCAGCGGCGTGCACACC TTCCCGGCTGTCCTACAGTCCTCAGGACTCTACTCCCTCAGCA GCGTGGTGACCGTGCCCTCCAGCAGCTTGGGCACCCAGACCTA CATCTGCAACGTGAATCACAAGCCCAGCAACACCAAGGTGGAC AAGAAAGTTGAGCCCAAATCTTGTGACAAAACTCACACATGCC CACCGTGCCCAGCACCTGAAGCGCTGGGGCACCGTCAGTCTT CCTCTTCCCCCCAAAACCCAAGGACACCCTCATGATCTCCCGG ACCCCTGAGGTCACATGCGTGGTGGTGGACGTGAGCCACGAAG ACCCTGAGGTCAAGTTCAACTGGTACGTGGACGGCGTGGAGGT GCATAATGCCAAGACAAAGCCGCGGGAGGAGCAGTACAACAGC ACGTACCGTGTGGTCAGCGTCCTCACCGTCCTGCACCAGGACT GGCTGAATGGCAAGGAGTACAAGTGCAAGGTCTCCAACAAAGC CCTCCCAGCCCCCATCGAGAAAACCATCTCCAAAGCCAAAGGG CAGCCCCGAGAACCACAGGTGTACACCCTGCCCCCATCCCGGG AGGAGATGACCAAGAACCAGGTCAGCCTGACCTGCCTGGTCAA AGGCTTCTATCCCAGCGACATCGCCGTGGAGTGGGAGAGCAAT GGGCAGCCGGAGAACAACTACAAGACCACGCCTCCCGTGCTGG ACTCCGACGGCTCCTTCTTCCTCTATAGCAAGCTCACCGTGGA CAAGAGCAGGTGGCAGCAGGGGAACGTCTTCTCATGCTCCGTG ATGCATGAGGCTCTGCACAACCACTACACGCAGAAGAGCCTCT CCCTGTCCCCCGGA |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated antibody, or antigen-binding fragment thereof, that specifically binds PDGF-B and comprises:
   a $V_H$ comprising the CDR-H1 amino acid sequence of SEQ ID NO:7, the CDR-H2 amino acid sequence of SEQ ID NO:8, and the CDR-H3 amino acid sequence of SEQ ID NO: 9; and
   a $V_L$ comprising the CDR-L1 amino acid sequence of SEQ ID NO:10, the CDR-L2 amino acid sequence of SEQ ID NO:11, and the CDR-L3 amino acid sequence of SEQ ID NO:12.

2. The antibody, or antigen-binding fragment thereof, of claim 1, wherein:
   the VL comprises the amino acid sequence of SEQ ID NO:4 and
   the VH comprises the amino acid sequence of SEQ ID NO:6.

3. The antibody of claim 2, wherein said antibody comprises a heavy chain comprising the sequence of SEQ ID NO:14, and a light chain comprising the amino acid sequence of SEQ ID NO:16.

4. The antibody, or antigen-binding fragment thereof, of claim 1 wherein said antibody specifically binds PDGF-B with a $K_D$ ranging from 2 pM to 15 pM, cross-competes with PDGFRβ for binding to PDGF-B, and inhibits an activity mediated by PDGF-B binding to PDGFRβ.

5. The antibody of claim 4, wherein said activity mediated by PDGF-B binding to PDGFRβ is at least one selected from the group consisting of phosphorylation of said PDGFRβ, induction of cell proliferation, induction of cell migration, and increase deposition of extracellular matrix.

6. A pharmaceutical composition comprising an antibody, or antigen-binding fragment thereof, according to claim 4, and a pharmaceutically acceptable carrier or excipient.

7. A pharmaceutical composition comprising an antibody, or antigen-binding fragment thereof, according to claim 1, and a pharmaceutically acceptable carrier or excipient.

* * * * *